US007955852B2

(12) United States Patent
Peled et al.

(10) Patent No.: US 7,955,852 B2
(45) Date of Patent: Jun. 7, 2011

(54) EXPANSION OF RENEWABLE STEM CELL POPULATIONS

(75) Inventors: Tony Peled, Mevaseret Zion (IL); Avi Treves, Mevaseret Zion (IL); Oren Rosen, Jerusalem (IL)

(73) Assignee: Gamida Cell Ltd., Jerusalem (IL)

( * ) Notice: Subject to any disclaimer, the term of this patent is extended or adjusted under 35 U.S.C. 154(b) by 654 days.

(21) Appl. No.: 10/774,843

(22) Filed: Feb. 9, 2004
(Under 37 CFR 1.47)

(65) Prior Publication Data
US 2005/0008624 A1 Jan. 13, 2005

Related U.S. Application Data

(63) Continuation of application No. PCT/IL03/00064, filed on Jan. 26, 2003.

(60) Provisional application No. 60/404,137, filed on Aug. 19, 2002, provisional application No. 60/376,183, filed on Apr. 30, 2002, provisional application No. 60/350,360, filed on Jan. 24, 2002.

(51) Int. Cl.
C12N 5/02 (2006.01)
C12N 5/07 (2006.01)
C12N 5/071 (2006.01)
(52) U.S. Cl. ......... 435/377; 435/325; 435/366; 435/384
(58) Field of Classification Search .................. 435/377, 435/325, 366, 384
See application file for complete search history.

(56) References Cited

U.S. PATENT DOCUMENTS

| | | |
|---|---|---|
| 3,687,808 A | 8/1972 | Merigan, Jr. et al. |
| 3,715,345 A | 2/1973 | Smith |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,863,008 A | 1/1975 | Grant |
| 3,867,517 A | 2/1975 | Ling |
| 3,876,623 A | 4/1975 | Jackson et al. |
| 3,879,262 A | 4/1975 | Schuurs et al. |
| 3,901,654 A | 8/1975 | Gross |
| 3,935,074 A | 1/1976 | Rubenstein et al. |
| 3,936,074 A | 2/1976 | Prinoth et al. |
| 3,984,533 A | 10/1976 | Uzgiris |
| 3,996,345 A | 12/1976 | Ullman et al. |
| 4,034,074 A | 7/1977 | Miles |
| 4,036,945 A | 7/1977 | Haber |
| 4,098,876 A | 7/1978 | Piasio et al. |
| 4,331,647 A | 5/1982 | Goldenberg |
| 4,469,863 A | 9/1984 | Ts'o et al. |
| 4,476,301 A | 10/1984 | Imbach et al. |
| 4,642,120 A | 2/1987 | Nevo et al. ............... 623/16 |
| 4,666,828 A | 5/1987 | Gusella |
| 4,683,202 A | 7/1987 | Mullis |
| 4,687,808 A | 8/1987 | Jarrett et al. |
| 4,801,531 A | 1/1989 | Frossard |
| 4,806,484 A | 2/1989 | Petrossian et al. |
| 4,816,567 A | 3/1989 | Cabilly et al. |
| 4,866,052 A | 9/1989 | Hider et al. |
| 4,868,116 A | 9/1989 | Morgan et al. |
| 4,879,219 A | 11/1989 | Wands et al. |
| 4,946,778 A | 8/1990 | Ladner et al. |
| 4,980,286 A | 12/1990 | Morgan et al. |
| 5,011,771 A | 4/1991 | Bellet et al. |
| 5,013,830 A | 5/1991 | Ohtsuka et al. |
| 5,023,243 A | 6/1991 | Tullis |
| 5,034,506 A | 7/1991 | Summerton et al. |
| 5,081,035 A | 1/1992 | Halberstadt et al. |
| 5,149,797 A | 9/1992 | Pederson et al. |
| 5,166,315 A | 11/1992 | Summerton et al. |
| 5,166,320 A | 11/1992 | Wu et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |

(Continued)

FOREIGN PATENT DOCUMENTS
AU 759522 8/1999
(Continued)

OTHER PUBLICATIONS

Yang et al., In vitro trans-differentiation of adult hepatic stem cells into pancreatic endocrine hormone-producing cells. Proc Natl Acad Sci U S A. Jun. 11, 2002;99(12):8078-83. Epub Jun. 4, 2002.* Rankin et al., Quantitative studies of inhibitors of ADP-ribosylation in vitro and in vivo. J Biol Chem. Mar. 15, 1989;264(8):4312-7.*
Banasik M,Specific inhibitors of poly(ADP-ribose) synthetase and mono(ADP-ribosyl)transferase.J Biol Chem. Jan. 25, 1992;267(3):1569-75.*
Gallacher L, et al., Isolation and characterization of human CD34(−)Lin(−) and CD34(+)Lin(−) hematopoietic stem cells using cell surface markers AC133 and CD7.Blood. May 1, 2000;95(9):2813-20.*
Genazzani et al., A Ca2+ release mechanism gated by the novel pyridine nucleotide, NAADPTrends in Pharmacological Sciences vol. 18, Issue 4, Jul. 1997, pp. 108-110.*
Guse, Cyclic ADP-ribose (cADPR) and nicotinic acid adenine dinucleotide phosphate (NAADP): novel regulators of Ca2+-signaling and cell function2002, Current Molecular Medicine, pp. 273-282.*

(Continued)

*Primary Examiner* — Maria Leavitt
(74) *Attorney, Agent, or Firm* — Mintz Levin Cohn Ferris Glovsky and Popeo, P.C.; Ivor R. Elrifi; Matthew Pavao

(57) ABSTRACT

Ex vivo and in vivo methods of expansion of renewable stem cells, expanded populations of renewable stem cells and their uses.

11 Claims, 17 Drawing Sheets

U.S. PATENT DOCUMENTS

| | | | |
|---|---|---|---|
| 5,272,057 A | 12/1993 | Smulson et al. | |
| 5,276,019 A | 1/1994 | Cohen et al. | |
| 5,278,302 A | 1/1994 | Caruthers et al. | |
| 5,281,521 A | 1/1994 | Trojanowski et al. | |
| 5,286,717 A | 2/1994 | Cohen et al. | |
| 5,320,963 A | 6/1994 | Knaack et al. | |
| 5,321,131 A | 6/1994 | Agrawal et al. | |
| 5,342,781 A | 8/1994 | Su | |
| 5,366,878 A | 11/1994 | Pedersen et al. | |
| 5,378,725 A | 1/1995 | Bonjouklian et al. | 514/453 |
| 5,399,676 A | 3/1995 | Froehler | |
| 5,403,711 A | 4/1995 | Walder et al. | |
| 5,405,938 A | 4/1995 | Summerton et al. | |
| 5,405,939 A | 4/1995 | Suhadolnik et al. | |
| 5,434,257 A | 7/1995 | Matteucci et al. | |
| 5,437,994 A | 8/1995 | Emerson et al. | |
| 5,453,496 A | 9/1995 | Caruthers et al. | |
| 5,455,233 A | 10/1995 | Spielvogel et al. | |
| 5,466,677 A | 11/1995 | Baxter et al. | |
| 5,470,967 A | 11/1995 | Huie et al. | |
| 5,476,925 A | 12/1995 | Letsinger et al. | |
| 5,480,906 A | 1/1996 | Creemer et al. | 514/453 |
| 5,486,359 A | 1/1996 | Caplan et al. | 424/93.7 |
| 5,489,677 A | 2/1996 | Sanghvi et al. | |
| 5,491,133 A | 2/1996 | Walder et al. | |
| 5,504,103 A | 4/1996 | Bonjouklian et al. | 514/453 |
| 5,519,126 A | 5/1996 | Hecht | |
| 5,536,821 A | 7/1996 | Agrawal et al. | |
| 5,539,082 A | 7/1996 | Nielsen et al. | |
| 5,541,306 A | 7/1996 | Agrawal et al. | |
| 5,541,307 A | 7/1996 | Cook et al. | |
| 5,545,806 A | 8/1996 | Lonberg et al. | |
| 5,545,807 A | 8/1996 | Surani et al. | |
| 5,550,111 A | 8/1996 | Suhadolnik et al. | |
| 5,561,225 A | 10/1996 | Maddry et al. | |
| 5,563,253 A | 10/1996 | Agrawal et al. | |
| 5,565,350 A | 10/1996 | Kmiec | |
| 5,569,825 A | 10/1996 | Lonberg et al. | |
| 5,571,799 A | 11/1996 | Tkachuk et al. | |
| 5,587,361 A | 12/1996 | Cook et al. | |
| 5,596,086 A | 1/1997 | Matteucci et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,612,211 A | 3/1997 | Wilson et al. | |
| 5,618,704 A | 4/1997 | Sanghvi et al. | |
| 5,623,065 A | 4/1997 | Cook et al. | |
| 5,623,070 A | 4/1997 | Cook et al. | |
| 5,625,050 A | 4/1997 | Beaton et al. | |
| 5,625,126 A | 4/1997 | Lonberg et al. | |
| 5,631,219 A | 5/1997 | Rosenthal et al. | |
| 5,633,360 A | 5/1997 | Bischofberger et al. | |
| 5,633,425 A | 5/1997 | Lonberg et al. | |
| 5,652,355 A | 7/1997 | Metelev et al. | |
| 5,652,356 A | 7/1997 | Agrawal | |
| 5,654,186 A | 8/1997 | Cerami et al. | 435/325 |
| 5,661,016 A | 8/1997 | Lonberg et al. | |
| 5,663,312 A | 9/1997 | Chaturvedula | |
| 5,674,750 A | 10/1997 | Kraus et al. | |
| 5,677,437 A | 10/1997 | Teng et al. | |
| 5,677,439 A | 10/1997 | Weis et al. | |
| 5,700,922 A | 12/1997 | Cook | |
| 5,712,154 A | 1/1998 | Mullon et al. | |
| 5,714,331 A | 2/1998 | Buchardt et al. | |
| 5,716,411 A | 2/1998 | Orgill et al. | 623/15 |
| 5,716,616 A | 2/1998 | Prockop et al. | 424/93.7 |
| 5,719,262 A | 2/1998 | Buchardt et al. | |
| 5,736,396 A | 4/1998 | Bruder et al. | 435/366 |
| 5,741,899 A | 4/1998 | Capon et al. | |
| 5,770,378 A | 6/1998 | Hwang et al. | |
| 5,770,580 A | 6/1998 | Ledley et al. | |
| 5,776,699 A | 7/1998 | Klein et al. | |
| 5,789,245 A | 8/1998 | Dubensky, Jr. et al. | |
| 5,789,543 A | 8/1998 | Ingham et al. | |
| 5,792,751 A | 8/1998 | Ledley et al. | |
| 5,814,482 A | 9/1998 | Dubensky, Jr. et al. | |
| 5,830,760 A | 11/1998 | Tsai et al. | 435/377 |
| 5,837,544 A | 11/1998 | Capon et al. | |
| 5,843,723 A | 12/1998 | Dubensky, Jr. et al. | |
| 5,844,079 A | 12/1998 | Ingham et al. | |
| 5,851,832 A | 12/1998 | Weiss et al. | |
| 5,851,984 A | 12/1998 | Matthews et al. | |
| 5,877,207 A | 3/1999 | Klein et al. | |
| 5,945,309 A | 8/1999 | Ni et al. | |
| 5,945,337 A * | 8/1999 | Brown | 435/389 |
| 5,952,345 A | 9/1999 | Klein et al. | |
| 5,958,954 A | 9/1999 | Klein et al. | |
| 5,990,329 A | 11/1999 | Klaus et al. | |
| 6,008,204 A | 12/1999 | Klein et al. | |
| 6,015,686 A | 1/2000 | Dubensky, Jr. et al. | |
| 6,015,694 A | 1/2000 | Dubensky, Jr. et al. | |
| 6,063,797 A | 5/2000 | Fesus et al. | |
| 6,077,947 A | 6/2000 | Capon et al. | |
| 6,090,810 A | 7/2000 | Klein et al. | |
| 6,117,850 A | 9/2000 | Patchen et al. | |
| 6,130,230 A | 10/2000 | Chambon et al. | |
| 6,133,309 A | 10/2000 | Bollag et al. | |
| 6,136,600 A | 10/2000 | Sato et al. | |
| 6,165,747 A | 12/2000 | Ingham et al. | |
| 6,218,128 B1 | 4/2001 | Klein et al. | |
| 6,228,848 B1 | 5/2001 | Klein et al. | |
| 6,232,291 B1 | 5/2001 | Ni et al. | |
| 6,261,786 B1 | 7/2001 | Marigo et al. | |
| 6,270,964 B1 | 8/2001 | Michnick et al. | |
| 6,271,363 B1 | 8/2001 | Ingham et al. | |
| 6,284,540 B1 | 9/2001 | Milbrandt et al. | |
| 6,294,330 B1 | 9/2001 | Michnick et al. | |
| 6,303,374 B1 | 10/2001 | Zhang et al. | |
| 6,306,575 B1 | 10/2001 | Thomas et al. | |
| 6,326,174 B1 | 12/2001 | Joyce et al. | |
| 6,326,198 B1 | 12/2001 | Emerson et al. | |
| 6,329,169 B1 | 12/2001 | Ni et al. | |
| 6,335,195 B1 | 1/2002 | Rodgers et al. | |
| 6,338,942 B2 | 1/2002 | Kraus et al. | |
| 6,342,219 B1 | 1/2002 | Thorpe et al. | |
| 6,342,221 B1 | 1/2002 | Thorpe et al. | |
| 6,342,372 B1 | 1/2002 | Dubensky, Jr. et al. | |
| 6,342,581 B1 | 1/2002 | Rosen et al. | |
| 6,372,210 B2 | 4/2002 | Brown | |
| 6,372,473 B1 | 4/2002 | Moore et al. | |
| 6,376,236 B1 | 4/2002 | Dubensky, Jr. et al. | |
| 6,384,192 B1 | 5/2002 | Ingham et al. | |
| 6,413,772 B1 * | 7/2002 | Block | 435/370 |
| 6,413,773 B1 | 7/2002 | Ptasznik et al. | 435/377 |
| 6,642,019 B1 | 11/2003 | Anderson et al. | |
| 6,645,489 B2 | 11/2003 | Pykett et al. | |
| 6,680,166 B1 | 1/2004 | Mullon et al. | |
| 6,887,704 B2 | 5/2005 | Peled et al. | |
| 6,962,698 B1 | 11/2005 | Peled et al. | |
| 7,169,605 B2 | 1/2007 | Peled et al. | 435/326 |
| 7,247,477 B2 | 7/2007 | Itskovitz-Eldor et al. | |
| 7,312,078 B2 | 12/2007 | Peled et al. | |
| 7,344,881 B2 | 3/2008 | Peled et al. | |
| 7,456,017 B2 * | 11/2008 | Kubota et al. | 435/370 |
| 2001/0014475 A1 | 8/2001 | Frondoza et al. | |
| 2002/0001826 A1 | 1/2002 | Wager et al. | |
| 2002/0090603 A1 | 7/2002 | Lipton et al. | |
| 2002/0114784 A1 | 8/2002 | Li et al. | 424/93.2 |
| 2002/0114789 A1 | 8/2002 | Peled et al. | |
| 2002/0145816 A1 | 10/2002 | Nickel et al. | |
| 2002/0146678 A1 | 10/2002 | Benvenisty | |
| 2002/0146816 A1 | 10/2002 | Vellinger et al. | |
| 2002/0159981 A1 | 10/2002 | Peled et al. | 424/93.7 |
| 2002/0182728 A1 | 12/2002 | Ramiya et al. | |
| 2003/0002363 A1 | 1/2003 | Le et al. | |
| 2003/0031665 A1 | 2/2003 | Dang et al. | |
| 2003/0113913 A1 | 6/2003 | Purton et al. | |
| 2003/0125410 A1 | 7/2003 | Keita et al. | |
| 2003/0149074 A1 | 8/2003 | Melese et al. | 514/312 |
| 2003/0215445 A1 | 11/2003 | Serrero | 424/145.1 |
| 2003/0235909 A1 | 12/2003 | Hariri et al. | |
| 2004/0076603 A1 | 4/2004 | Peled et al. | |
| 2004/0247574 A1 | 12/2004 | Christopherson, II et al. | |
| 2005/0008624 A1 | 1/2005 | Peled et al. | |
| 2005/0031595 A1 | 2/2005 | Peled et al. | |
| 2005/0054097 A1 * | 3/2005 | Peled et al. | 435/372 |
| 2005/0054103 A1 | 3/2005 | Peled et al. | |

| | | | |
|---|---|---|---|
| 2005/0069527 A1 | 3/2005 | Laughlin et al. | |
| 2005/0084961 A1 | 4/2005 | Hedrick et al. | |
| 2005/0095228 A1 | 5/2005 | Fraser et al. | |
| 2005/0118150 A1 | 6/2005 | Peled et al. | |
| 2005/0214262 A1 | 9/2005 | Peled et al. | |
| 2005/0220774 A1 | 10/2005 | Peled et al. | 424/93.21 |
| 2006/0171932 A1 | 8/2006 | Hendricks et al. | |
| 2006/0205071 A1 | 9/2006 | Hasson et al. | |
| 2007/0077652 A1 | 4/2007 | Peled et al. | |
| 2008/0279828 A1 | 11/2008 | Peled et al. | |
| 2009/0004158 A1 | 1/2009 | Peled et al. | |

FOREIGN PATENT DOCUMENTS

| | | |
|---|---|---|
| AU | 770896 | 4/2000 |
| AU | 2000277535 B2 | 3/2007 |
| EP | 0190048 | 8/1986 |
| EP | 0190048 A2 | 8/1986 |
| EP | 0 331 464 A2 | 9/1989 |
| EP | 1 332 673 A1 | 8/2003 |
| EP | 1 332 676 B1 | 8/2003 |
| JP | 07-504570 T | 5/1995 |
| WO | WO 89/02468 | 3/1989 |
| WO | WO 89/05345 | 6/1989 |
| WO | WO 89/07136 | 8/1989 |
| WO | WO 92/07573 | 5/1992 |
| WO | WO 92/11355 | 7/1992 |
| WO | WO 93/09220 | 5/1993 |
| WO | WO 93/18132 | 9/1993 |
| WO | WO 94/18991 | 9/1994 |
| WO | WO 95/14078 | 5/1995 |
| WO | WO 95/21911 | 8/1995 |
| WO | WO 95/24464 | 9/1995 |
| WO | WO 96/01108 | 1/1996 |
| WO | WO 96/40876 | 12/1996 |
| WO | WO 97/04707 | 2/1997 |
| WO | WO 97/31647 | 9/1997 |
| WO | WO 97/33978 | 9/1997 |
| WO | WO-9734999 A1 | 9/1997 |
| WO | WO 97/41209 | 11/1997 |
| WO | WO 97/41224 | 11/1997 |
| WO | WO 98/25634 | 6/1998 |
| WO | WO 99/07831 | 2/1999 |
| WO | WO 99/18885 | 4/1999 |
| WO | WO 99/40783 | 8/1999 |
| WO | WO 00/18885 | 4/2000 |
| WO | WO 00/30635 | 6/2000 |
| WO | WO 00/46349 | 8/2000 |
| WO | WO 00/66712 | 11/2000 |
| WO | WO 00/73421 | 12/2000 |
| WO | WO-0229012 A1 | 4/2002 |
| WO | WO 02/064755 | 8/2002 |
| WO | WO 02/080995 | 10/2002 |
| WO | WO 03/004626 | 1/2003 |
| WO | WO 03/062369 A2 | 7/2003 |
| WO | WO 03/062404 A1 | 7/2003 |
| WO | WO 03/072557 A1 | 9/2003 |
| WO | WO 03/078567 A2 | 9/2003 |
| WO | 2004/078917 A2 | 9/2004 |
| WO | WO 2004/016731 A2 | 9/2004 |
| WO | WO 2005/007073 | 1/2005 |
| WO | WO 2005/007799 | 1/2005 |
| WO | WO 2005/086845 * | 9/2005 |
| WO | WO 2006/030442 | 3/2006 |
| WO | WO 2007/063545 | 6/2007 |
| WO | WO 2008/056368 | 5/2008 |

OTHER PUBLICATIONS

Ngo, J. et al., "Computational Complexity, Protein Structure Prediction, and the Levinthal Paradox", 1994, The Protein Folding Problem and Tertiary Structure Prediction, Merz et al. (eds.), Birkhauser Boston: Boston, MA, pp. 433 and 492-495.*
Voet, Biochemistry John Wiley and Sons, 1990, pp. 126-128.*
Colon -Otero et al., Inhibition of hemopoietic growth factor-induced proliferation by adenosine diphosphate-ribosylation inhibitors, Blood. Sep. 1987;70(3):686-93.*
Munshi CB, et al., Evidence for a causal role of CD38 expression in granulocytic differentiation of human HL-60 cells J Biol Chem. Dec. 20, 2002;277(51):49453-8. Epub Oct. 16, 2002.*

Schwartz et al., Multipotent adult progenitor cells from bone marrow differentiate into functional hepatocyte-like cells J. Clin. Invest. 109(10): 1291-1302 (2002).*
Berardi et al. Blood, 89(10):3554-3564 (1997).
Brandt et al. Blood, 94(1):106-113 (1999).
Cakir-Kiefer et al. Biochem. J., 358:399-406 (2001).
Casal et al. Blood, 97(6):1625-1634 (2001).
Chen et al. Stroke, 32:1005-1011 (2001).
Chisi et al. Stem Cells, 15:455-460 (1997).
Defacque et al., Biochem. Biophys. Res. Commun., 220:315-322 (1996).
De Luca et al. Endocrinol., 141(1):346-353, abstract only (2000).
De Wynter et al. Stem Cells, 16:387-396 (1998).
Feldman Globes Online (2004).
Grande et al. J. Leukoc. Biol., 71:641-651 (2002).
Hamilton The Wall Street J. Online (2003).
Hammond et al. Exp. Hematol., 16:674-680 (1988).
Hida et al. Jpn. J. Pharmacol., 85:60-69 (2001).
Hirose et al. Exp. Cell Res., 221(2):294-300 abstract only (1995).
Hmama et al. J. Exp. Med ., 190(11):1583-1594 (1999).
Holleman "Chemical Hazard Information Profile Draft Report", abstract only (1982).
Huang et al. Exp. Biol. Med., 226(3):222-228 (2001).
Jiang et al. Proc. Natl. Acad. Sci. USA, 97(4):1749-1753 (2000).
Johnson et al. Bioorg. Med. Chem., 7(7):1321-1338 (1999).
Johnson et al. Blood, 99(3):746-753 (2002).
Kang et al. Exp. Cell Res., 256:545-554 (2000).
Kastner et al. Blood, 97(5):1314-1320, abstract only (2001).
Kishimoto et al. J. Biol. Chem., 273(25):15429-15434, abstract only (1998).
Lee et al. Leukemia, 10:1751-1757 (1996).
Matzner et al. Hum. Gene Ther., 12:1021-1033 (2001).
Mehta et al. Blood, 89(10):3607-3614, abstract only (1997).
Mehta et al. Leukemia and Lymphoma, 32(5/6):441-449 (1999).
Mills et al. Cell Growth Differ., 7(3):327-337, abstract only (1996).
Peled et al. Blood, 96(Part 1):776a-777a, abstract #3359 (2000).
Peled et al. Blood, 96(11-Part 1):773a, abstract #3343 (2000).
Ratajczak et al. Br. J. Hematol., 93:772-782 (1996).
Rusten et al. Blood, 87(5):1728-1736, abstract only (1996).
Schmetzer et al. Hematol., 2:11-19 (1997).
Sekhar et al. Hum. Gene Ther., 7:33-38 (1996).
Sergeant et al. J. Cell. Physiol., 163:477-485 (1995).
Shimakura et al. Stem Cells, 18:183-189 (2000).
Szilvassy et al. Blood, 98(7):2108-2115 (2001).
Todisco et al. Blood, 95(2)535-542, abstract only (2000).
Verlinden et al. J. Bone Mineral Res., 16(4):625-638 (2001).
Wendling et al. Proc. Natl. Acad. Sci. USA, 96(2):547-551 (1999).
Yin et al. Blood, 90(12):5002-5012 (1997).
Zocchi et al. FASEB J., 13(2):273-283, abstract only (1999).
Acsadi et al. "Human Dystrophin Expression in Mdx Mice After Intramuscular Injection of DNA Constructs", Nature, 352: 815-818, 1991.
Armentano et al. "Expression of Human Factor IX in Rabbit Hepatocytes by Retrovirus-Mediated Gene Transfer: Potential for Gene Therapy of Hemophilia B", Proc. Natl. Acad. Sci. USA, 87: 6141-6145, 1990.
Banno et al. "Anemia and Neutropenia in Eldery Patients Caused by Copper Deficiency for Long-Term Eternal Nutrition", Rinsho-Ketsueki, English abstract only, 35: 1276-1281, 1994.
Belovari et al. "Differentiation of Rat Neural Tissue in a Serum-Free Embryo Culture Model Followed by In Vivo Transplantation", Croatian Medical Journal, 42(6): 611-617, 2001. Abstract.
Berkner "Development of Adenovirus Vectors for the Expression of Heterologous Genes", BioTechniques, 6(7): 616-629, 1988.
Bi et al. "Effect of Lactoferrin on Proliferation and Differentiation of the Jurkat Human Lymphoblastic T Cell Line", Arch. Immunol. Ther. Exp., 45(4): 315-320, 1997. Abstract.
Bird et al. "Single-Chain Antigen-Binding Proteins", Science, 242: 423-426, 1988.
Boerner et al. "Production of Antigen-Specific Human Monoclonal Antibodies From In Vitro-Primed Human Splenocytes", The Journal of Immunology, 147(1): 86-95, 1991.

Briddell et al. "Purification of CD34+ Cells Is Essential for Optimal Ex Vivo Expansion of Umbilical Cord Blood Cells", Journal of Hematotherapy, 6: 145-150, 1997.

Brigham et al. "Rapid Communication: In Vivo Transfection of Murine Lungs With a Functioning Prokaryotic Gene Using a Liposome Vehicle", The American Journal of the Medical Sciences, 298(4): 278-281, 1989.

Brugger et al. "Ex Vivo Expansion of Enriched Peripheral Blood CD34+ Progenitor Cells by Stem Cell Factor, Interleukin-1β (IL-1β). IL-6, IL-3, Interferon-γ, and Erythropoietin", Blood, 81(10); 2579-2584, 1993.

Brugnera et al. "Cloning, Chromosomal Mapping and Characterization of the Human Metal-Regulatory Transcription Factor MTF-1", Nucleic Acids Research, 22(15): 3167-3173, 1994.

Buskin et al. "Identification of a Myocyte Nuclear Factor That Binds to the Muscle-Specific Enhancer of the Mouse Muscle Creatine Kinase Gene", Molecular and Cellular Biology, 9(6): 2627-2640, 1989.

Cepko "Overview of the Retrovirus Transduction System", Short Protocols in Molecular Biology, Unit 9.10-9.14: 9-41-9-57, 1984.

Chen et al. "Fibroblast Growth Factor (FGF) Signaling Through PI 3-Kinase and Akt/PKB is Required for Embryoid Body Differentiation", Oncogene, 19: 3750-3756, 2000. p. 3752-3755.

Chowdhury et al. "Long-Term Improvement of Hypercholesterolemia After Ex Vivo Gene Therapy in LDLR-Deficient Rabbits", Science, 254: 1802-1805, 1991.

Colter et al. "CD34+ Progenitor Cell Selection: Clinical Transplantation, Tumor Cell Purging, Gene Therapy, Ex Vivo Expansion, and Cord Blood Processing", Journal of Hematology, 5: 179-184, 1996.

Cristiano et al. "Hepatic Gene Therapy: Adenovirus Enhancement of Receptor-Mediated Gene Delivery and Expression in Primary Hepatocytes", Proc. Natl. Acad. Sci. USA, 90: 2122-2126, 1993.

Curiel et al. "Adenovirus Enhancement of Transferrin-Polylysine-Mediated Gene Delivery", Proc. Natl. Acad. Sci. USA, 88: 8850-8854, 1991.

Dabeva et al. "Transcription Factor and Liver-Specific mRNA Expression in Facultative Epithelial Progenitor Cells of Liver and Pancreas", American Journal of Pathology, 147: 1633-1648, 1995. Abstract.

Dahl et al. "Tranformation of Hematopoietic Cells by the Ski Oncoprotein Involves Repression of Retinoic Acid Receptor Signaling", Proc. Natl. Acad. Sci. USA, 95(19): 11187-11192, 1998.

Dai et al. "Gene Therapy Via Primary Myoblasts: Long-Term Expression of Factor IX Protein Following Transplantation In Vivo", Proc. Natl. Acad. Sci. USA, 89: 10892-10895, 1992.

Dalyot et al. "Adult and Neonatal Patterns of Human Globin Gene Expressioon Are Recapitulated in Liquid Cultures", Experimental Hematology, 20: 1141-1145, 1992.

Danos et al. "Safe and Efficient Generation of Recombinant Retroviruses With Amphotropic and Ecotropic Host Ranges", Proc. Natl. Acad. Sci. USA, 85: 6460-6464, 1988.

Datta et al. "Ionizing Radiation Activates Transcription of the EGR1 Gene Via CArG Elements", Proc. Natl. Acad. Sci. USA, 89: 10149-10153, 1992.

Dexter et al. "Conditions Controlling the Proliferation of Haemopoietic Stem Cells In Vitro", Journal of Cell Physiology, 91: 335-344, 1976.

Ebner et al. "Distinct Roles for PI3K in Proliferation and Survival of Oligodendrocyte Progenitor Cells", Journal of Neuroscience Research, 62: 336-345, 2000. p. 338-344.

Eglitis et al. "Gene Expression in Mice After High Efficiency Retroviral-Mediated Gene Transfer", Science, 230: 1395-1398, 1985.

Englisch et al. "Chemically Modified Oligonucleotides as Probes and Inhibitors", Angewandte Chemie (International Edition in English), 30(6): 613-629, 1991.

Ferry et al. "Retroviral-Mediated Gene Transfer Into Hepatocytes In Vivo", Proc. Natl. Acad. Sci. USA, 88: 8377-8381, 1991.

Fibach et al. "Growth of Human Normal Erythroid Progenitors in Liquid Culture: A Comparison With Colony Growth in Semisolid Culture", International Journal of Cell Cloning, 9: 57-64, 1991.

Fibach et al. "Normal Differentiation of Myeloid Leukemic Cells Induced by Differentiation-Indicing Protein", Nature, 237: 276-278, 1972.

Fibach et al. "Proliferation and Maturation of Human Erythroid Progenitors in Liquid Culture", Blood, 73(1): 100-103, 1989. Abstract.

Fibach et al. "Retinoic Acid Antagonist Inhibits CD38 antigen Expression on Human Hematopoietic Cells", Blood, 100(11): 172A & 44th Annual Meeting of the American Society of Hematology, 2002. Abstract.

Fibach et al. "The Two-Step Liquid Culture: A Novel Procedure for Studying Maturation of Human Normal and Pathological Erythroid Precursors", Stem Cells, 11(Supp1.1): 36-41, 1993. Abstract.

Filvaroff et al. "Functional Evidence for an Extracellular Calcium Receptor Mechanism Triggering Tyrosine Kinase Activation Associated With Mouse Keratinocyte Differentiation", The Journal of Biological Chemistry, 269(34): 21735-21740, 1994.

Fishwild et al. "High-Avidity Human IgGκ Monoclonal Antibodies From a Novel Strain of Minilocus Transgenic Mice", Nature Biotechnology, 14: 845-851, 1996.

Flores et al. "Akt-Mediated Survival of Oligodendrocytes Induced by Neuregulins", The Journal of Neuroscience, 20(20): 7622-7630, 2000. p. 7624-7629.

Flotte et al. "Expression of the Cystic Fibrosis Transmemebrane Conductance Regulators From a Novel Adeno-Associated Virus Promoter", The Journal of Biological Chemistry, 268(5): 3781-3790, 1993.

Flotte et al. "Gene Expression From Adeno-Associated Virus Vectors in Airways Epithelial Cells", Amercan Journal of Respiratory Cell and Molecular Biology, 7: 349-356, 1992.

Fosmire "Zinc Toxicity", American Journal of Clinical Nutrition, 51(2): 225-227, 1990. Abstract.

Gagnon et al. "Activation of Protein Kinase B and Induction of Adipogenesis by Insulin in 3T3-L1 Preadipocytes", Diabetes, 48: 691-698, 1999. p. 693-697.

Gould-Fogerite et al. "Chimerasome-Mediated Gene Transfer In Vitro and In Vivo", Gene, 84: 429-438, 1989.

Gur et al. "Toelrance Induction by Megadose Hematopoietic Progenitor Cells: Expansion of Veto Cells by Short-Term Culture of Purified Human CD34+ Cells", Blood, 99: 4174-4181, 2002.

Haj-Ahmad et al. "Development of a Helper-Independent Human Adenovirus Vector and Its Use in the Transfer of the Herpes Simplex Virus Thymidine Kinase Gene", Journal of Virology, 57(1): 267-274, 1986.

Hatayama et al. "Regulation of HSP70 Synthesis Induced by Cupric Sulfate and Zinc Sulfate in Thermotolerant HeLa Cells", Journal of Biochemistry, Tokyo, 114(4): 592-597, 1993. Abstract.

Haylock et al. "Ex-Vivo Expansion and Maturation of Peripheral Blood CD34+ Cells Into the Myeloid Lineage", Blood, 80(5): 1405-1412, 1992.

Hermonat et al. "Use of Adeno-Associated Virus as a Mammalian DNA Cloning Vector: Transduction of Neomycin Resistance Into Mammalian Tissue Culture Cells", Proc. Natl. Acad. Sci. USA, 81: 6466-6470, 1984.

Herz et al. "Adenovirus-Mediated Transfer of Low Density Lipoprotein Receptor Gene Acutely Accelerates Cholesterol Clearence in Normal Mice", Proc. Natl. Acad. Sci. USA, 90: 2812-2816, 1993.

Heuchel et al. "The Transcription Factor MTF-I is Essential for Basal and Heavy Metal-Induced Metallothionein Gene Expression", The EMBO Journal, 13(12): 2870-2875, 1994.

Hoffman et al. "Zinc-Induced Copper Deficiency", Gastroenterology, 94(2); 508-512, 1988.

Hoogenboom et al. "By-Passing Immunisation. Human Antibodies From Synthetic Repertoires of Germline $V_H$ Gene Segments Rearranged In Vitro", Journal of Molecular Biology, 227: 381-388, 1992.

Huber et al. "Retroviral-Mediated Gene Therapy for the Treatment of Hepatocellular Carcinoma: An Innovative Approach for Cancer Therapy", Proc. Natl. Acad. Sci. USA, 88: 8039-8043, 1991.

Hutvágner et al. "RNAi: Nature Abhors a Double-Strand", Current Opinion in Genetics & Development, 12: 225-232, 2002.

Hwu et al. "Functional and Molecular Characterization of Tumor-Infiltrating Lymphocytes Transduced With Tumor Necrosis Factor-α cDNA for the Gene Therapy of Cancer in Humans", The Journal of Immunology, 150(9): 4104-4115, 1993.

Inbar et al. "Localization of Antibody-Combining Sites Within the Variable Portions of Heavy and Light Chains", Proc. Natl. Acad. Sci. USA, 69(9): 2659-2662, 1972.

Itoh et al. "Inhibition of Urokinase Receptor (uPAR) Expression by RNA-Cleaving Catalytic DNA (DNAzyme) Containing Antisense uPAR", Molecular Therapy, 5(5/Part 2): S134, 2002.

Jones et al. "Replacing the Complementarity-Determining Regions in a Human Antibody With Those From a Mouse", Nature, 321: 522-525, 1986.

Kaufman et al. "Translational Efficency of Polycistronic mRNAs and Their Utilization to Express Heterologous Genes in Mammalian Cells", The EMBO Journal, 6(1): 187-193, 1987.

Kay et al. "Hepatic Gene Therapy: Persistent Expression of Human α1-Antitrypsin in Mice After Direct Gene Delivery In Vivo", Human Gene Therapy, 3: 641-647, 1992.

Khachigian "DNAzymes: Cutting a Path to a New Class of Therapeutics", Current Opinion in Molecular Therapeutics, 4(2): 119-121, 2002.

Kim "Differentiation and Identification of the Two Catalytic Metal Binding Sites in Bovine Lens Leucine Aminopeptidase by X-Ray Crystallography", Proc. Natl. Acad. Sci. USA, 90(11): 5006-5010, 1993.

Kizaki et al. Regulation of Manganese Superoxide Dismutase and Other Antioxidant Genes in Normal and Leukemic Hematopoietic Cells and Their Relationship to Cytotoxicity by Tumor Necrosis Factor, Blood, 82(4): 1142-1150, 1993.

Köehler et al. "Defining Optimum Conditions for the Ex Vivo Expansion of Human Umbilical Cord Blood Cells. Influences of Progenitor Enrichment, Interference With Feeder Layers, Early-Acting Cytokines and Agitation of Culture Vessels", Stem Cells, 17(1: 19-24, 1999.

Koizumi et al. "Large Scale Purification of Human Blood CD34+ Cells From Cryopreserved Peripheral Blood Stem Cells, Using a Nylon-Fiber Syringe System and Immunomagnetic Microspheres", Bone Marrow Transplantation, 26: 787-793, 2000.

Lapidot et al. "Cytokine Stimulation of Multilineage Hematopoiesis From Immature Human Cells Engrafted in SCID Mice", Science, 255: 1137-1141, 1992.

Larrick et al. "PCR Amplification of Antibody Genes", Methods: A Companion to Methods in Enzymology, 2(2): 106-110, 1991.

Lawlor et al. "Coordinate Control of Muscle Cell Survival by Distinct Insulin-Like Growth Factor Activated Signaling Pathways", The Journal of Cell Biology, 151(6): 1131-1140, 2000. p. 1133-1139.

Lemarchand et al. "Adenovirus-Mediated Transfer of a Recombinant Human α1-Antitrypsin cDNA to Human Endothelial Cells", Proc. Natl. Acad. Sci. USA, 89: 6482-6486, 1992.

Lewandowski et al. "Phosphatidylinositol 3-Kinases Are Involved in the All-Trans Retinoic Acid-Induced Upregulation of CD38 Antigen on Human Haematopoietic Cells", British Journal of Hematology, 118(2): 535-544, 2002. Fig.8.

Li et al. "Activation of Phosphatidylinositol-3 Kinase (PI-3K) and Extracellular Regulated Kinases (Erk ½) is Involved in Muscarinic Receptor-Mediated DNA Synthesis in Neural Progenitor Cells", The Journal of Neuroscience. 21(5): 1569-1579, 2001. p. 1572-1578.

Lonberg et al. "Antigen-Specific Human Antibodies From Mice Comprising Four Distinct Genetic Modifications", Nature, 368: 856-859, 1994.

Lonberg et al. "Human Antibodies From Transgenic Mice", International Review in Immunology, 13: 65-93, 1995.

Lutton et al. "Zinc Porphyrins: Potent Inhibitors of Hematopoieses in Animal and Human Bone Marrow", Proc. Natl. Acad. Sci. USA, 94: 1432-1436, 1997.

Mader et al. "A Steroid-Inducible Promoter for the Controlled Overexpression of Cloned Genes in Eukaryotic Cells", Proc. Natl. Acad. Sci. USA, 90: 5603-5607, 1993.

Manome et al. "Coinduction of C-Jun Gene Expression and Internucleosomal DNA Fragmentation by Ionizing Radiation", Biochemistry, 32: 10607-10613, 1993.

Mar et al. "A Conserved CATTCCT Motif is Required for Skeletal Muscle-Specific Activity of the Cardiac Troponin T Gene Promoter", Proc. Natl. Acad. Sci. USA, 85: 6404-6408, 1988.

Marks et al. "By-Passing Immunization. Human Antibodies From V-Gene Libraries Displayed on Phage", Journal of Molecular biology, 222: 581-597, 1991.

Marks et al. "By-Passing Immunization: Building High Affinity Human Antibodies by Chain Shuffling", Bio/Technology, 10: 779-783, 1992.

Martelli et al. "Transplants Across Human Leukocyte Antigen Barriers", Seminars in Hematology, 39(1): 48-56, 2002.

McLaughlin et al. "Adeno-Associated Virus General Transduction Vectors: Analysis of Proviral Structures", Journal of Virology, 62(6): 1963-1973, 1988.

McNiece et al. "Action of Interleukin-3, G-CSF on Highly Enriched Human Hematopoietic Preogenitor Cells: Synergistic Interaction of GM-CSF Plus G-CSF", Blood, 74: 110-114, 1989.

McNiece et al. "CD34+ Cell Selection From Frozen Cord Blood Products Using the Isolex 300i and CliniMACS CD34 Selection Devices", Journal of Hematotherapy, 7: 457-461, 1998.

Migliaccio et al. "Long-Term Generation of Colony-Forming Cells in Liquid Culture of CD34+ Cord Blood Cells in the Presence of Recombinant Human Stem Cell Factor", Blood, 79: 2620-2627, 1992.

Miller "Progress Toward Human Gene Therapy", Blood, The Journal of the American Society of Hematology, 76(2): 271-278, 1990.

Morier-Teissier et al. "Synthesis and Antitumor Properties of an Anthraquinone Bisubstituted by the Copper Chelating Peptide Gly-Gly-L-His", Journal of Medical Chemistry, 36: 2084-2090, 1993. Abstract.

Morrison "Success in Specification", Nature, 368(6474): 812-813, 1994.

Muench et al. "Interactions Among Colony-Stimulating Factors, IL-1β, IL-6, and Kit-Ligand in the Regulation of Primitive Murine Hematopoietic Cells", Experimental Hematology. 20: 339-349, 1992.

Muzyczka "Use of Adeno-Associated Virus as a General Transduction Vector for Mammalian Cells", Current Topics in Microbiology and Immunology, 158: 97-129, 1992.

Narita et al. "Cardiomycyte Differentiation by GATA-4-Deficient Embryonic Stem Cells", Development, 122(19): 3755-3764, 1996.

Neuberger "Generating High-Avidity Human Mabs in Mice", Nature Biotechnology, 14: 826, 1996.

Nicolau et al. "Liposomes as Carriers for In Vivo Gene Transfer and Expression", Methods in Enzymology, 149(Chap.16): 157-176, 1987.

Okazaki et al. "Characteristics and Partial Purification of a Novel Cytosolic, Magnesium-Independent, Neutral Sphingomyelinase Activated in the Early Signal Transduction of 1α,25-Dihydroxyvitamin D3-Induced HL-60 Cell Differentiation", The Journal of Biological Chemistry, 269(6): 4070-4077, 1994.

Oliveras et al. "Copper as an Essential Nutrient", Am. J. Clin. Nutr., 63:791S-796S, 1996.

Pack et al. "Improved Bivalent Miniantibodies, With Identical Avidity as Whole Antibodies, Produced by High Cell Density Fermentation of *Escherichia Coli*", Bio/Technology, 11: 1271-1277, 1993.

Percival et al. "Copper is Required to Maintain Cu/Zn-Superoxide Dismutase Activity During HL-60 Cell Differentiation", Proc. Soc. Exp. Biol. Med., 203: 78-83, 1993.

Petersen et al. "Hepatic Oval Cells Express the Hematopoietic Stem Cell Marker Thy-1 in the Rat", Hepatology, 27(2): 433-445, 1998.

Pickart et al. "Growth Modulating Plasma Tripeptide May Function by Facilitating Copper Uptake Into Cells", Nature, 288(18/25): 715-717, 1980. Abstract. p. 716, col. 2, Line1.

Porter "The Hydrolysis of Rabbit γ-Globulin and Antibodies With Crystalline Papain", Biochemical Journal, 73: 119-126, 1959.

Presta "Antibody Engineering", Current Opinion in Structural Biology, 2: 593-596, 1992.

Purdy et al. "Large Volume Ex Vivo Expansion of CD34+-Positive Hematopoietic Progenitor Cells for Transplantation", Journal of Hematotherapy, 4: 515-525, 1995.

Quantin et al. "Adenovirus as an Expression Vector in Muscle Cells In Vivo", Proc. Natl. Acad. Sci. USA, 89: 2581-2584, 1992.

Reeves et al. "High Zinc Concentrations in Culture Media Affect Copper Uptake and Transport in Differentiated Human Colon Adenocarcinoma Cells", Journal of Nutrition, 126(6): 1701-1712, 1996. Abstract.

Reid et al. "Interactions of Tumor Necrosis Factor With Granulocyte-Macrophage Colony-Stimulating Factor and Other Cytokines in the Regulation of Dendritic Cell Growth In Vitro From Early Bipotent CD34+ Progenitors in Human Bone Marrow", Journal of Immunology, 149(8): 2681-2688, 1992. Abstract. p. 2686, col. 1, 2nd §, p. 2682, col. 1, 2nd §.

Riechmann et al. "Reshaping Human Antibodies for Therapy", Nature, 332: 323-327, 1988.

Rosenfeld et al. "Adenovirus-Mediated Transfer of a Recombinant α1-Antitrypsin Gene to the Lung Epithelium In Vivo", Science, 252: 431-434, 1991.

Rosenfeld et al. "In Vivo Transfer of the Human Cystic Fibrosis Transmembrane Conductance Regulator Gene to the Airway Epithelium", Cell, 68: 143-155, 1992.

Rowley et al. "Isolation of CD34+ Cells From Blood Stem Cell Components Using the Baxter Isolex System", Bone Marrow Transplantation, 21: 1253-1262, 1998.

Sammons et al. "Mechanisms Mediating the Inhibitory Effect of All-Trans Retinoic Acid on Primitive Hematopoietic Stem Cells in Human Long-Term Bone Marrow Culture", Stem Cells, 18(3): 214-219, 2000.

Samulski et al. "Helper-Free Stocks of Recombinant Adeno-Associated Viruses: Normal Integration Does Not Require Viral Gene Expression", Journal of Virology, 63(9): 3822-3828, 1989.

Sato et al. "In Vitro Expansion of Human Peripheral Blood CD34+ Cells", Blood, 82(12): 3600-3609, 1993.

Sauve et al. "Mechanism-Based Inhibitors of CD38: A Mammalian Cyclic ADP-Ribose Synthetase", Biochemistry, 41(26): 8455-8463, 2002.

Schwartz et al. "In Vitro Myelopoiesis Stimulated by Rapid Medium Exchange and Supplementation With Hematopoietic Growth Factors", Blood, 78(12): 3155-3161, 1991.

Seed "An LFA-3 cDNA Encodes a Phospholipid-Linked Membrane Protein Homologous to its Receptor CD2", Nature, 329: 840-842, 1987.

Selden "Transfection Using DEAE-Dextran", Short Protocols in Molecular Biology, Unit 9.2: 9-9-9-11, 1984.

Selden et al. "Optimization of Transfection", Short Protocols in Molecular Biology, Unit 9.4: 262-263, 1984.

Slavin et al. "Donor Lymphocyte Infusion: The Use of Alloreactive and Tumor-Reactive Lymphocytes for Immunotherapy of Malignant and Nonmalignant Diseases in Conjunction With Allogeneic Stem Cell Transplantation", Journal of Hematotherapy & Stem Cell Research, 11: 265-276, 2002.

Slavin et al. "Treatment of Leukemia by Alloreactive Lymphocytes and Nonmyeloablative Stem Cell Transplantation", Journal of Clinical Immunology, 22(2): 64-69, 2002.

Spencer et al. "Controlling Signal Transduction With Synthetic Ligands", Science, 262: 1019-1024, 1993.

Takeshita et al. "Selective Stimulation by Ceramide of the Expression of the α Isoform of Retinoic Acid and Retinoid X Receptors in Osteoblastic Cells", Journal of Biological Chemistry, 275(41): 32220-32226, 2000.

Tratschin et al. "A Human Parvovirus, Adeno-Associated Virus, as a Eucaryotic Vector. Transient Expression and Encapsidation of the Procaryotic Gene for Chloramphenicol Acetyltransferase", Molecular and Cellular Biology, 4(10): 2072-2081, 1984.

Tratschin et al. "Adeno-Associated Virus Vector for High-Frequency Integration, Expression, and Rescue of Genes in Mammalian Cells", Molecular and Cellular Biology, 5(11): 3251-3260, 1985.

Tratschin et al. "Genetic Analysis of Adeno-Associated Virus: Properties of Deletion Mutants Constructed In Vitro and Evidence for an Adeno-Associated Virus Replication Function", Journal of Virology, 51(3): 611-619, 1984.

Tuba et al. "Synthesis and Structure—Activity Relationships of Neuromuscular Blocking Agents", Current Medicinal Chemistry, 9: 1507-1536, 2002.

Van Beusechem et al. "Long-Term Expression of human Adenosine Deaminase in Rhesus Monkeys Transplanted With Retrovirus-Infected Bone-Marrow Cells", Proc. Natl. Acad. Sci. USA, 89: 7640-7644, 1992.

Verfaillie "Can Human Hematopoietic Stem Cells Be Cultured Ex Vivo?", Stem Cells, 12(5): 466-476, 1994. Abstract.

Verfaillie "Direct Contact Between Human Primitive Hematopoietic Progenitors and Bone Marrow Stroma is Not Required for Long-Term In Vitro Hematopoiesis", Blood, 79(11): 2821-2826, 1992.

Verhoeyen et al. "Reshaping Human Antibodies: Grafting an Antilysozyme Activity", Science, 239: 1534-1536, 1988.

Wall et al. "Inhibition of the Intrinsic NAD+ Glycohydrolase Activity of CD38 by Carbocyclic NAD Analogues", Biochemical Journal, 335(3): 631-636, 1998.

Wang et al. "PH-Sensitive Immunoliposomes Mediate Target-Cell-Specific Delivery and Controlled Expression of a Foreign Gene in Mouse", Proc. Natl. Acad. Sci. USA, 84: 7851-7855, 1987.

Whitlow et al. "Single-Chain Fv Proteins and Their Fusion Proteins", Methods: A Companion to Methods in Enzymology, 2(2): 97-105, 1991.

Wilson et al. "Hepatocyte-Directed Gene Transfer In Vivo Leads to Transient Improvement of Hypercholesterolemia in Low Density Lipoprotein Receptor-Deficient Rabbits", The Journal of Biological Chemistry, 267(2): 963-967, 1992.

Wilson et al. "Retrovirus-Mediated Transduction of Adult Hepatocytes", Proc. Natl. Acad. Sci. USA, 85: 3014-3018, 1988.

Wolff et al. "Direct Gene Transfer Into Mouse Muscle In Vivo", Science, 247: 1465-1468, 1990.

Wondisford et al. "Cloning of the Human Thyrotropin β-Subunit Gene and Transient Expression of Biologically Active Human Thyrotropin After Gene Transfection", Molecular Endocrinology, 2: 32-39, 1988.

Wu et al. "Receptor-Mediated Gene Delivery and Expression In Vivo", The Journal of Biological Chemistry, 263(29): 14621-14624, 1988.

International Search Report for PCT/IL03/00064, mailed Oct. 17, 2006.

ACS, "Chelation Therapy", *American Cancer Society*, pp. 1-5 (2006).

Avital et al., "Isolation, Characterization, and Transplantation of Bone Marrow-Derived Hepatocyte Stem Cells", *Biochem. Biophy. Res. Comm.*, 288(1):156-164 (2001).

Burgada et al., "Synthesis of New Phosphonated Tripod Ligands as Putative New Therapeutic Agents in the Chelation Treatment of Metal Intoxications", *Euro. J. Org. Chem.*, pp. 349-352 (2001).

Charrier et al., "Normal Human Bone Marrow CD34+CD133+ Cells Contain Primitive Cells Able to Produce Different Categories of Colony-Forming Unit Megacaryocytes" in Vitro, *Exper. Hema.*, 30:1051-1060 (2002).

Coutinho et al., "Effects of Recombinant Human Granulocyte Colony-Stimulating Factor (CSF), Human Granulocyte Macrophage-CSF, and Gibbon Interleukin-3 on Hematopoiesis Human Long-Term Bone Marrow Culture", *Blood*, 75(11):2118-2129 (1990).

Fasouliotis et al., "Human Umbilical Cord Blood Banking and Transplantation: A State of Art", *Euro. J. Obstet. Gynec. Reprod. Bio.*, 90(1):13-25 (2000).

Ferrero et al., "The Metamorphosis of a Molecule: From Soluble Enzyme to the Leukocyte Receptor CD38", *J. Leuk. Bio.*, 65(2):151-161 (1999).

Fietz et al., "Culturing Human Umbilical Cord Blood: A Comparison of Mononuclear Vs CD34+ Selected Cells", *Bone Marrow Transplantation*, 39:11-23 (2007).

Gossler et al., "Transgenesis by Means of Blasocyst-Derived Embryonic Stem Cell Lines", *PNAS*, 83:9065-9069 (1986).

Hofmeister et al., "Ex Vivo Expansion of Umbilical Cord Blood Stem Cells for Transplantation: Growing Knowledge From the Hematopoietic Niche", *Bone Marrow Transplantation*, 39:11-23 (2007).

Jackson et al., "Regeneration of Ischemic Cardiac Muscle and Vascular Endothelium by Adult Stem Cells", *J. Clin. Invest.*, 107:1395-1402 (2001).

Keith et al., "Multicomponent Therapeutics for Networked Systems", *Nat. Rev.: Drug Disc.*, 4:1-8 (2005).

Kocher et al., "Neovascularization of Ischemic Myocardium by Human Bone-Marrow-Derived Angioblasts Prevents Cardiomyocyte Apoptosis, Reduces Remodeling and Improves Cardiac Function", *Nat. Med.*, 7(4):430-436 (2001).

Lam et al., "Preclinical Ex Vivo Expansion of Cord Blood Hematopoietic Stem and Progenitor Cells: Duration of Culture: the Media, Serum Supplements, and Growth Factors Used; and Engraftment in NOD/SCID Mice", *Transfusion*, 41(12):1567-1576 (2001) (Abstract).

Lianguzova et al., "PI3-Kinase Inhibitors LY294002 and Wortmannin Have Different Effects on Proliferation of Murine Embryonic Stem Cells", *Tsitologiia*, 48(7):560-568 (2006) (English Abstract Only).

Lovejoy et al., "Novel 'Hybrid' Iron Chelators Derived From Aroylhydrazones and Thiosemicarbazones Demonstrate Delective Antiproliferative Activity Against Tumor Cells", *Blood*, 100(2):666-676 (2002).

Mehta et al., "Human CD38, A Cell-Surface Protein With Multiple Functions", *J. FASEB*, 10(12):1408-1417 (1996).

Murray et al., Thrombopoietin, Flt3, and Kit Ligands Together Suppress Apoptosis of Human Mobilized CD34+ Cells and Recruit Primitive CD34+Thy-1+ Cells Into Rapid Divions', *Expert. Hemat.*, 27:1019-1028 (1999).

Orlic et al., "Mobilized Bone Marrow Cells Repair the Infarcted Heart, Improving Function and Survival", *PNAS*, 98(18):10344-10324 (2001).

Ostrakhovitch et al., "Copper Ions Strongly Activate the Phosphoinositide-3-Kinase/Akt Pathway Independent of the Generation of Reactive Oxygen Species", *Arch. Biochem. Biophy.*, 397(2):232-239 (2002).

Paling et al., "Regulation of Embryonic Stem Cell Self-Renewal by Phosphoinositide 3-Kinase-Dependent Signaling", *J. Bio. Chem.*, 279(46):48063-48070 (2004).

Peled et al., "Linear Polyamine Copper Chelator Tetraethylenepentamine Augments Long-Term Ex Vivo Expansion of Cord Blood-Derived CD34+ Cells and Increases Their Engraftment Potential in NOD/SCID Mice", *Exper. Hemat.*, 32:547-555 (2004).

Peters et al., "Long-Term Ex Vivo Expansion of Human Fetal Liver Primitive Haematopoietic Progenitor Cells in Stroma-Free Cultures", *Brit. J. Haemat.*, 119:792-802 (2002).

Wang et al., "In Vitro Culture of Umbilical Cord Blood MNC and CD34+ Selected Cells", *Sheng Wu Gong Cheng Xue Bao*, 18(3):343-347 (2002) (Abstract).

Wulf et al., "Somatic Stem Cell Plasticity: Current Evidence and Emerging Concepts", *Exp. Hemat.*, 29:1361-1370 (2001).

Bertagnolo et al., "Phosphoinositide 3-Kinase Activity Is Essential for All-*trans*-Retinoic Acid-induced Granulocytic Differentiation of HL-60 Cells'", *Cancer Res.*, 59:542-546 (1999).

Hayashi et al., "Changes in the Balance of Phosphoinositide 3-Kinase/Protein Kinase B (Akt) and the Mitogenactivated Protein Kinases (ERK/p38MAPK) Determine a Phenotype of Visceral and Vascular Smooth Muscle Cells", *J. Cell Biol.*, 145(4):727-740 (1999).

Howard et al., "Formation and Hydrolysis of Cyclic ADP-Ribose Catalyzed by Lymphocyte Antigen CD38", *Science*, 262(5136):1056-1059 (1993).

Lu et al., "Intravenous Administration of Human Umbilical Cord Blood Reduces Neurological Deficit in the Rat After Traumatic Brain Injury", *Cell Transplant.*, 11(3):275-281 (2002).

Marcinkowska, "Does the Universal 'Signal Transduction Pathway of Differentiation' Exist? Comparison of Different Cell Differentiation Experimental Models With Differentiation of HL-60 Cells in Response to 1,25-Dihydroxyvitamin D3", *Postepy Hig. Med. Dosw.*, 53(2):305-313 (1999) (Abstract only).

Orlic et al., "Bone Marrow Cells Regenerate Infarcted Myocardium", *Nature*, 410: 701-705 (2001).

Orlic et al., "Exogenous Hematopoietic Stem Cells Can Regenerate Infarcted Myocardium",*Circulation*, 102:2672 (2000) (Abstract only).

Australian Government, IP Australia Re.: Application No. 20042011623 Examination Report Dated Dec. 5, 2005.

Australian Government, IP Australia Re.: Application No. 2003208577 Examination Report Dated Feb. 11, 2008.

Australian Government, IP Australia Re.: Application No. 2004217699 Examination Report Dated Jun. 14, 2007.

Australian Government, IP Australia Re.: Application No. 2004201623 Examination Report Dated Oct. 25, 2005.

Australian Government, IP Australia Re.: Application No. 2005200679 Examination Report Dated Aug. 28, 2007.

Canadian Intellectual Property Office Re.: Application No. 2,320,073 Official Action Dated Jul. 4, 2008.

Canadian Intellectual Property Office Re.: Application No. 2,344,653 Official Action Dated Jul. 7, 2006.

Canadian Intellectual Property Office Re.: Application No. 2,344,653 Official Action Dated Dec. 17, 2007.

Canadian Intellectual Property Office Re.: Application No. 2,320,073 Official Action Dated Mar. 22, 2007.

Government of India, Patent Office Re.: Application No. 2544/CHENP/2005 Examination Report Dated Jun. 7, 2006.

Government of India, Patent Office Re.: Application No. 390/CHENP/05 Examination Report Dated Apr. 14, 2006.

Israeli Patent Office Re.: Application No. 163180 Office Action Dated Apr. 2, 2008.

Israeli Patent Office Re.: Application No. 170676 Office Action and English Translation Dated Dec. 9, 2008.

Israeli Patent Office Re.: Application No. 163991 Office Action Dated May 27, 2008.

Japanese Patent Office Re.: Application No. 2000-572333 English Translation of Notice of Reason for Rejection Dated Mar. 11, 2005.

Japanese Patent Office Re.: Application No. 2000-531059 English Translation of Notice of Reason for Rejection Dated Sep. 27, 2005.

Japanese Patent Office Re.: Application No. 2003-576562 English Translation of Notice of Reason for Rejection Dated Jan. 30, 2009.

US Patent and Trademark Office Re.: U.S. Appl. No. 10/508,244 Official Action Dated Jul. 3, 2007.

US Patent and Trademark Office Re.: U.S. Appl. No. 10/767,064 Official Action Dated Oct. 4, 2007.

US Patent and Trademark Office Re.: U.S. Appl. No. 10/767,064 Official Action Dated Feb. 5, 2008.

US Patent and Trademark Office Re.: U.S. Appl. No. 10/767,064 Office Action Dated Nov. 6, 2008.

US Patent and Trademark Office Re.: U.S. Appl. No. 10/508,244 Official Action Dated Mar. 10, 2008.

US Patent and Trademark Office Re.: U.S. Appl. No. 12/070,543 Official Action Dated Jan. 13, 2009.

US Patent and Trademark Office Re.: U.S. Appl. No. 10/767,064 Official Action Dated Jan. 18, 2007.

US Patent and Trademark Office Re.: U.S. Appl. No. 10/774,843 Official Action Dated Mar. 18, 2008.

US Patent and Trademark Office Re.: U.S. Appl. No. 10/795,215 Official Action Dated Feb. 19, 2009.

US Patent and Trademark Office Re.: U.S. Appl.No. 10/767,064 Official Action Dated Sep. 26, 2006.

US Patent and Trademark Office Re.: U.S. Appl. No. 10/508,244 Official Action Dated Oct. 31, 2008.

Response Dated Feb. 27, 2009 to US Patent and Trademark Office Official Action of Oct. 31, 2008 Re.: U.S. Appl. No. 10/508,244.

Aiuti et al. "The Chemokine SDF-1 is a Chemoattractant for Human CD34+ Hematopoietic Progenitor Cells and Provides a New Mechanism to Explain the Mobilization of CD34+ Progenitors to Peripheral Blood", Journal of Experimental Medicine, 185(1): 111-120, 1997.

Anderlini et al. "The Use of Mobilized Peripheral Blood Stem Cells From Normal Donors for Allografting", Stem Cells, 15: 9-17, 1997.

Aoki et al. "In Vivo Transfer Efficiency of Antisense Oligonucleotides Into the Myocardium Using HVJ-Liposome Method", Biochemical and Biophysical Research Communications, 231: 540-545, 1997.

Arriero et al. "Adult Skeletal Muscle Stem Cells Differentiate Into Endothelial Lineage and Ameliorate Renal Dysfunction After Acute Ischemia", American Journal of Physiology—Renal Physiology, 287: F621-F627, 2004.

Asahara et al., "Stem cell therapy and gene transfer for regeneration", *Gene Therapy*, 7:451-457 (2000).

Auger et al. "PDGF-Dependent Tyrosine Phosphorylation Stimulates Production of Novel Polyphosphoinositides in Intact Cells", Cell, 57: 167-175, 1989.

Baggiolini "Chemokines and Leukocyte Traffic", Nature, 392: 565-568, 1998.

Bhat-Nakshatri, et al., "Tumour necrosis factor and PI3-kinase control oestrogen receptor alpha protein level and its transrepression function", *Br. J. Cancer*, 90:853-859 (2004).

Bieback et al., "Critical Parameters for the Isolation of Mesenchymal Stem Cell from Umbilical Cord Blood", *Stem Cells*, 22:625-634 (2004).

Birkenkamp, et al., "An inhibitor of PI3-K differentially affects proliferation and IL-6 protein secretion in normal and leukemic myeloid cells depending on the stage of differentiation", *Exp. Hematol.*, 28:1239-1249 (2000).

Bohmer et al. "Fetal Cell Isolation From Maternal Blood Cultures by Flow Cytometric Hemoglobin Profiles", Fetal Diagnosis and Therapy, 17(2): 83-89, 2002.

Bongers et al. "Kinetics of Dipeptyl Peptidase IV Proteolysis of Growth Hormone-Releasing Factor and Analogs", Biochimica et Biophysica Acta, 1122: 147-153, 1992.

Brott et al. "Flow Cytometric Characterization of Perfused Human Bone Marrow Cultures: Identification of the Major Cell Lineages and Correlation With the CFU-GM Assay", Cytometry Part A, 53A: 22-27, 2003.

Broxmeyer "Regulation of Hematopoiesis by Chemokine Family Members", International Journal of Hematology, 74: 9-17, 2001.

Bryder et al. "Hematopoietic Stem Cells: the paradigmatic tissue-specific stem cell." Am J Pathol., 169(2):338-46, 2006.

Butt "Introduction to Chemical Reactor Theory", Reaction Kinetics and Reactor Design, Chap.4: 184-241, 1980.

Chen et al. "Differentiation of Rat Marrow Mesenchymal Stem Cells into Pancreatic Islet Beta-Cells", World Journal of Gastroeneterology, 19(20): 3016-3020, 2004.

Christopherson II et al. "Cell Surface Peptidase CD26/Dipeptidylpeptidase IV Regulates CXCL12/Stromal Cell-Derived Factor-1α-Mediated Chemotaxis of Human Cord Blood CD34+ Progenitor Cells", The Journal of Immunology, 169: 7000-7008, 2002.

Christopherson II et al. "Modulation of Hematopoietic Stem Cell Homing and Engraftment by CD26", Science, 305: 1000-1003, 2004.

Cole et al. "The EBV-Hybridoma Technique and its Application to Human Lung Cancer", Monoclonal Antibodies and Cancer Therapy, p. 77-96, 1985.

Collins et al. "Stirred Culture of Peripheral and Cord Blood Hematopoietice Cells Offers Advantages over Traditional Static Systems for Clinically Relevant Applications", Biotechnology and Bioengineering, 59(5): 534-543.

Corda et al. "Functional Aspects of Protein Mono-ADP-Ribosylation", The EMBO Journal, 22(9): 1953-1958, 2003.

Czauderna, et al., "Functional studies of the PI(3)-kinase signalling pathway employing synthetic and expressed siRNA.", *Nuc. Acid Res.*, 31(2):670-682 (2003).

Czyz et al. "Potential of Embryonic and Adult Stem Cell In Vitro", Biological Chemistry, 384: 1391-1409, 2003.

De La Cruz et al. "Do Protein Motifs Read the Histone Code?", BioEssays, 27.2: 164-175, 2005.

Donovan et al. "The End of the Beginning for Pluripotent Stem Cells", Nature, 414(6859): 92-97, 2001.

Dosil et al., "Mitogenic signalling and substrate specificity of the Flk2/Flt3 receptor tyrosine kinase in fibrobiasis and interleukin 3-dependent hematopoietic cells", *Mo. Cell Biol.*, 13(10):6572-6585 (1993). Abstract.

Ehring et al. "Expansion of HPCs From Cord Blood in a Novel 3D Matrix", Cytotherapy, 5(6): 490-499, 2003.

Ferrari et al. "Muscle Regeneration by Bone Marrow-Derived Myogenic Progenitors", Science, 279(5356): 1528-1530, 1998. Erratum in: Science, 281(5379): 923, 1998.

Forraz, et al., "AC133+ umbilical cord blood progenitors demonstrate rapid self-renewal and low apoptosis. ", *Br. J. Haematol.*, 119(2):516-524 (2002).

Fry, M. J., "Phosphoinositide 3-kinase signalling in breast cancer: how big a role might it play? ", *Breast Cancer Res.*, 3(5):304-312 (2001).

Gloeckner et al. "New Miniaturized Hollow-Fiber Bioreactor for In Vivo Like Cell Culture, Cell Expansion, and Production of Cell-Derived Products", Biotechnology Progresses, 17: 828-831, 2001.

Gluckman et al. "Hematopoietic Reconstitution in a Patient With Fanconi's Anemia by Means of Umbilical-Cord Blood From an HLA-Identical Sibling", The New England Journal of Medicine, 321(17): 1174-1178, 1989.

Haviernik et al., "Tissue inhibitor of matrix metalloproteinase-1 overexpression in M1 myeloblasts impairs IL-6-induced differentiation", *Oncogene,*, 23(57):9212-9219 (2004). Abstract.

Higashi et al., "Autologous Bone-Marrow Mononuclear Cell Implantation Improves Endothelium-Dependent Vasodilation in Patients With Limb Ischemia", *Circulation*, 109:1215-1218 (2004).

Hori et al. "Growth Inhibitors Promote Differentiation of Insulin-Producing Tissue From Embryonic Stem Cells", Proc. Natl. Acad. Sci. USA, 99(25): 16105-16110, 2002.

Hühn et al. "Molecular Analysis of CD26-Mediated Signal Transduction in T Cells", Immunology Letters, 72: 127-132, 2000.

Imai et al. "Selective Secretion of Chemoattractants for Haemapoietic Progenitor Cells by Bone Marrow 25Endothelial Cells: A Possible Role in Homing of Haemopoietic Progenitor Cells to Bone Marrow", British Journal of Haematology, 106: 905-911, 1999.

Imitola et al. "Directed Migration of Neural Stem Cells to Sites of CNS Injury by the Stroman Cell-Derived Factor 1α/CXC Chemokine Receptor 4 Pathway", Proc. Natl. Acad. Sci. USA, 101(52): 18117-18122, 2004.

Jelinek et al. "Novel Bioreactors for the Ex Vivo Cultivation of Hematopoietic Cells", English Life Science, 2(1): 15-18, 2002.

Kähne et al. "Dipetidyl Peptidase IV: A Cell Surface Peptidase Involved in Regulating T Cell Growth (Review)", International Journal of Molecular Medicine, 4: 3-15, 1999.

Kern et al., "Comparative Analysis of Mesenchymal stem cells from Bone Marrow, Umbilical Cord Blood, or Adipose Tissue", *Stem Cells*, 24:1294-1301 (2006).

Kitanaka, et al., "CD38 ligation in human B cell progenitors triggers tyrosine phosphorylation of CD19 and association of CD19 with lyn and phosphatidylinositol 3-kinase.", *J. Immunol.*, 159(1):184-192 (1997).

Kobari et al. "CD133+ cell selection is an alternative to CD34+ cell selection for ex vivo expansion of hematopoietic stem cells.", *J. Hematother Stem Cell Res.* 2001; 10(2):273-81.

Kronenwett et al. "Oligodeoxyribonucleotide Uptake in Primary Human Hematopoietic Cells is Enhanced by Cationic Lipids and Depends on the Hematopoietic Cell Subset", Blood, 91(3): 852-862, 1998.

Ku et al. "Committing Embryonic Stem Cells to Early Endocrine Pancreas In Vitro", Stem Cells, 22: 1205-1217, 2004.

Lambeir et al. "Kinetic Investigation of Chemokine Truncation by CD26/DipeptidylPeptidase IV Reveals a Striking Selectivity Within the Chemokine Family", The Journal of Biological Chemistry, 276(32): 29839-29845, 2001.

Lavigne et al. "Enhanced Antisense Inhibition of Human Immunodeficiency Virus Type 1 in Cell Cultures by DLS Delivery System", Biochemical and Biophysical Research Communications, 237: 566-571, 1997.

Lee et al. "Clonal Expansion of Adult Rat Hepatic Stem Cell Lines by Suppression of Asymetric Cell Kinetics (SACK)", Biotechnology and Bioengineering, 83: 760-771, 2003.

Lee et al. "Repair of Ischemic Heart Disease With Novel Bone Marrow-Derived Multipotent Stem Cells", Cell Cycle, 4(7): 861-864, 2005.

Luft "Making Sense Out of Antisense Oligodeoxynucleotide Delivery: Getting There is Half the Fun". J. Mol. Med, p. 75-76. 1998.

Lupi et al. "Endogenous ADP-Ribosylation of the G Protein β Subunit Prevents the Inhibition of Type 1 Adenylyl Cyclase", The Journal of Biological Chemistry, 275(13): 9418-9424, 2000.

Ma, et al., "Inhibition of phosphatidylinositol 3-kinase causes apoptosis in retinoic acid differentiated h1-60 leukemia cells.", *Cell Cycle*, 3(1):67-70 (2004).

Matuoka et al. "A Positive Role of Phosphatidylinositol 3-Kinase in Aging Phenotype Expression in Cultured Human Diploid Fibroblasts", Arch. Gerontol. Geriatry, 36:203-219, 2003.

McGrath et al. "Embryonic Expression and Function of the Chemokine SDF-1 and its Receptor, CXCR4", Developmental Biology, 213: 442-456, 1999.

McNiece et al., "Ex vivo Expansion of Cord Blood Mononuclear Cells on Mesenchymal Stem Cells", *Cytotherapy*, 6(4):311-317 (2004).

Meissner et al. "Development of a Fixed Bed Bioreactor for the Expansion of Human Hematopoietic Progenitor Cells", Cytotechnology, 30: 227-234, 1999.

Merck & Co. "The Merck Index, An Encyclopedia of Chemicals, Drugs and Biologicals", 10th Ed.(3742): 549, 1983.

Miraglia et al. "A Novel Five-Transmembrane Hematopoietic Stem Cell Antigen : Isolation, Characterization, and Molecular Cloning", Blood, 90(12): 5013-5021, 1997.

Mood, et al., "Contribution of JNK, Mek, Mos and PI-3K signaling to GVBD in Xenopus oocytes.", *Cell. Signalling*, 16:631-642 (2004).

Mulloy et al. "Maintaining the self-renewal and differentiation potential of human CD34+ hematopoietic cells using a single genetic element." Blood, 102(13):4369-76, 2003.

Murry et al., "Haematopoietic Stem Cells Do Not Transdifferentiate Into Cardiac Myocytes in Myocardial Infarcts", *Nature*, 428:664-668 (2004).

Nagaya et al. "Intravenous Administration of Mesenchymal Stem Cells Improves Cardiac Functions in Rats With Acute Myocardial Infarction Through Angiogenesis and Myogenesis", American Journal of Physiology—Heart Circulation Physiology, 287: H2670-H2676, 2004.

Ohishi et al. "Delta-1 Enhances Marrow and Thymus Repopulating Ability of Human CD34+CD38-Cord Blood Cells", The Journal of Clinical Investigation, 110(8): 1165-1174, 2002.

Okuno et al. "Differential regulation of the human and murine CD34 genes in hematopoietic stem cells." Proc Natl Acad Sci U S A., 99(9):6246-51, 2002.

Orlic et al. "Transplanted Adult Bone Marrow Cells Repair Myocardial Infarcts in Mice", Annals of the New York Academy of Sciences, 938: 221-230, 2001. Abstract.

Park, et al., "Phosphatidylinositol 3-kinase regulates PMA-induced differentiation and superoxide production in HL-60 cells.", *Immunopharmacol. Immunotoxicol.*, 24(2):211-226 (2002).

Pei et al. "Bioreactors Mediate the Effectiveness of Tissue Engineering Scaffolds", The FASEB Journal, 16: 1691-1694, 2002.

Peled et al., "Chelatable Cellular Copper Modulates Differentiation and Self-Renewal of Cord Blood-Derived Hematopoietic Progenitor Cells", *Exp Hematol*, 33:1092-1100 (2005).

Peled et al. "Dependence of Human Stem Cell Engraftment and Repopulation of NOD/SCID Mice on CXCR4", Science, 283: 845-848, 1999.

Peled et al. "Copper chelators enable long term CFU and CD34+ cells expansions in cultures initiated with the entire mononuclear cell (MNC) fraction.", Blood, 100 (11), 2002. Abstract # 4076.

Pera MF. 2001. Human pluripotent stem cells: a progress report. Curr Opin Gen Devel 11:595-599.

Petzer et al., "Self-Renewal of Primitive Human Hematopoietic Cells (Long-Term-Culture-Initiating Cells) in vitro and Their Expansion in Defined Medium", *Proc Natl Acad Sci USA*, 93:1470-1474 (1996).

Porter et al. "Graft-Versus-Leukemia Effect of Allogeneic Bone Marrow Transplantation and Donor Mononuclear Cell Infusions", Cancer Treatment & Research, 77: 57-85, 1997. Abstract.

Prockop et al. "Isolation and Characterization of Rapidly Self-Renewing Stem Cells From Cultures of Human Marrow Stromal Cells", Cytotherapy, 3(5): 393-396, 2001.

Purton et al. "All-Trans Retinoic Acid Facilitates Oncoretrovirus-Mediated Transduction of Hematopoietic Repopulating Stem Cells", J. Hematother. Stem Cell Res., 10(8): 815-825, 2001. Abstract.

Rajur et al. "Covalent Protein-Oligoneucleotide Conjugates for Efficient Delivery of Antisense Molecules", Bioconjugate Chemistry, 8(6): 935-940, 1997.

Ratajczak MZ et al., "Hunt for pluripotent stem cell—regenerative medicine search for almighty cell.", J Autoimmun 30: 151-162, 2008.

Reya, T., "Regulation of Hematopoietic Stem Cell Self-Renewal", *Rec Prog Horm Res*, 58:283-295 (2003).

Reyes et al. "Origin of Endothelial Progenitors in Human Postnatal Bone Marrow", Journal of Clinical Investigation, 109: 337-346, 2002.

Roach et al. "Methods for the Isolation and Maintenance of Murine Embryonic Stem Cells", Methods in Molecular Biology—Embryonic Stem Cells: Methods and Protocols, 185: 1-16, 2002.

Roberts. "Mesenchymal Stem Cells", Vox Sanguinis, 87(Suppl. 2): s38-s41, 2004.

Robinson et al., "Superior Ex vivo Cord Blood Expansion Following Co-Culture With Bone Marrow-Derived Mesenchymal Stem Cells", *Bone Marrow Transplant.*, 37:359-366 (2006).

Rubinstein et al. "Processing and Cryopreservation of Placental/Umbilical Cord Blood for Unrelated Bone Marrow Reconstitution", Proc. Natl. Acad. Sci. USA, 92: 10119-10122, 1995.

Ryu et al. "Adenosine Triphosphate Induces Proliferation of Human Neural Stem Cells: Role of Calcium and P70 Ribosomal Protein S6 Kinase", Journal of Neuroscience Research, 72: 352-362, 2003.

Santoro et al. "A General Purpose RNA-Cleaving DNA Enzyme", Proc. Natl. Acad. Sci. USA, 94: 4262-4266, 1997.

Shioda et al. "Anti-HIV-1 and Chemotactic Activities of Human Stromal Cell-Derived Factor 1β(SDF-1α) and SDF-1β Are Abolished by CD26/Dipeptidyl Peptidase IV-Mediated Cleavage", Proc. Natl. Acad. Sci. USA, 95: 6331-6336, 1998.

Simmons et al. "Identification of Stromal Cell Precursors in Human Bone Marrow by a Novel Monoclonal Antibody, STRO-1", Blood, 78(1): 55-62, 1991.

Smith "Embryo-Derived Stem Cells: of Mice and Men", Annual Reviews of Cell and Developmental Biology, 17: 435-462, 2001.

Smith "The World According to PARP", Trends in Biochemical Sciences, 26(3): 174-179, 2001.

Struyf et al. "Natural Truncation of RANTES Abolishes Signaling Through the CC Chemokine Receptors CCR1 and CCR3, Impairs Its Chemotactic Potency and Generates a CC Chemokine Inhibitor", European Journal Immunology, 28: 1262-1271, 1998.

Sylvester et al. "Stem Cells: Review and Update", Archives of Surgery, 139: 93-99, 2004.

Tateishi-Yuyama et al., "Therapeutic angiogenesis for patients with limb ischaemia by autologous transplantation of bone-marrow cells: a pilot study and a randomised controlled trial", *The Lancet*, 360:427-435 (2002).

Tögel et al. "Administered Mesenchymal Stem Cells Protect Against Ischemic Acute Renal Failure Through Differentiation-Independent Mechanisms", American Journal of Physiology—Renal Physiology, 289: F31-F42, 2005.

Trounson "The Derivation and Potential Use of Human Embryonic Stem Cells", Reproduction, Fertility and Development, 13: 523-532, 2001.

Tse et al. "Angiogenesis in Ischaemic Myocardium by Intramyocardial Autologous Bone Marrow Mononuclear Cell Implantation", Lancet, 361: 47-49, 2003.

Turnpenny L et al., "Evaluating human embryonic germ cells: concord and conflict as pluripotent stem cells.", Stem Cells 24: 212-220, 2006.

Uchida et al. "Direct Isolation of Human Central Nervous System Stem Cells", Proc. Natl. Acad. Sci. USA, 97(26): 14720-14725, 2000.

Ueda et al. "ADP-Ribosylation", Annual Reviews of Biochemistry, 54: 73-100, 1985.

Vanham et al. "Decreased Expression of the Memory Marker CD26 on Both CD4+ and CD8+ T Lymphocytes of HIV-Infected Subjects", Journal of Acquired Immune Deficiency Syndromes, 6: 749-757, 1993.

Virág et al. "The Therapeutic Potential of Poly(ADP-Ribose) Polymerase Inhbititors", Pharmacological Reviews, 54(3): 375-429, 2002.

Vlahos, et al., "A specific inhibitor of phosphatidylinositol 3-kinase, 2-(4-morpholinyl)-8-phenyl-4H-1-benzopyran-4-one (LY294002).", *J. Biol. Chem.*, 269(7):5241-5248 (1994).

Wagers et al., "Little Evidence for Developmental Plasticity of Adult Hematopoietic Stem Cells", Science, 297(5590):2256-2259 (2002). Abstract.

Walton et al. "Prediction of Antisense Oligonucleotide Binding Affinity to a Structured RNA Target", Biotechnology and Bioengineering, 65(1): 1-9, 1999.

Xia et al. "Surface Fucosylation of Human Cord Blood Cells Augments Binding to P-Selectin and E-Selectin and Enhances Engraftment in Bone Marrow", Blood, 104(10): 3091-3096, 2004.

Yau et al. "Endogenous Mono-ADP-Ribosylation Mediates Smooth Muscle Cell Proliferation and Migration Via Protein Kinase Induction of C-Fos Expression", European Journal of Biochemistry, 270:101-110, 2003.

Ylä-Herttuala et al., "Gene transfer as a tool to induce therapeutic vascular growth", *Nature Medicine*, 9(6): 694-701 (2003).

Yoon et al., "Clonally Expanded Novel Multipotent Stem Cells From Human Bone Marrow Regenerate Myocardium After Myocardial Infarction", *J. Clin. Invest.*, 115(2):326-338 (2005).

Zenith "Zenith and US Robotics, A Complete Network Solution for Data Modem Communications Over One-Way Cable Plants", Zenith Network Systems Data Business Unit.

Audhya et al. "Tripeptide Structure of Bursin, A Selective B-Cell-Differentiating Hormone of the Bursa of Fabricius ", Science, 231(4741): 997-999, Feb. 28, 1986.

Guse "Cyclic ADP-Ribose (cADPR) and Nicotinic Acid Adenine Dinucleotide Phospahte (NAADP): Novel Regulators of Ca2+-Signaling and Cell Function", Current Molecular Medicine, 2(3): 273-282, 2002.

Hariharan "The Analysis of Microarray Data", Pharmacogenomics, 4(4): 477-497, 2003.

Lee et al. "Data Mining in Genomics", Clinics in Laboratory Medicine, 28(1): 145-viii, Mar. 2008.

Canadian Intellectual Property Office Re.: Application No. 2,479,679 Requisition by the Examiner Dated Jul. 15, 2009.

Canadian Intellectual Property Office Re.: Application No. 2,474,344 Requisition by the Examiner Dated Jul. 16, 2009.

Canadian Intellectual Property Office Re.: Application No. 2,474,344 Summary of Requisition by the Examiner Dated Sep. 30, 2009.

European Patent Office Re.: Application No. 03003275.9 Communication Pursuant to Article 94(3) EPC Dated Oct. 12, 2009.

European Patent Office Re.: Application No. 99906799.4 Communication Pursuant to Article 94(3) EPC Dated Oct. 12, 2009.

European Patent Office Re.: Application No. 99906799.4 Response Dated Dec. 2, 2009 to Communication Pursuant to Article 94(3) EPC of Oct. 12, 2009.

Japanese Patent Office Re.: Application No. 2006-507579 Translation of Notice of Reason for Rejection Dated Oct. 23, 2009.

Israeli Patent Office Re.: Application No. 163180 Office Action Dated Apr. 2, 2008.

Israeli Patent Office Re.: Application No. 163991 Office Action Dated May 27, 2008.

US Patent and Trademark Office Re.: U.S. Appl. No. 10/508,244 Official Action Dated Mar. 10, 2008.

US Patent and Trademark Office Re.: U.S. Appl. No. 10/508,244 Official Action Dated Sep. 4, 2009.

US Patent and Trademark Office Re.: U.S. Appl. No. 12/154,058 Official Action Dated Aug. 12, 2009.

US Patent and Trademark Office Re.: U.S. Appl. No. 10/767,064 Official Action Dated Sep. 26, 2006.

US Patent and Trademark Office Re.: U.S. Appl. No. 10/767,064 Official Action Dated Jan. 18, 2007.

US Patent and Trademark Office Re.: U.S. Appl. No. 10/767,064 Official Action Dated Nov. 6, 2008.

US Patent and Trademark Office Re.: U.S. Appl. No. 10/774,843 Official Action Dated Mar. 18, 2008.

US Patent and Trademark Office Re.: U.S. Appl. No. 10/774,843 Official Action Dated Sep. 21, 2009.

US Patent and Trademark Office Re.: U.S. Appl. No. 12/070,543 Notice of Allowance Dated Sep. 15, 2009.

US Patent and Trademark Office Re.: U.S. Appl. No. 10/795,215 Official Action Dated Sep. 4, 2009.

US Patent and Trademark Office Re.: U.S. Appl. No. 10/795,215 Official Action Dated Feb. 19, 2009.

European Search Report and the European Search Opinion Dated Jun. 8, 2010 From the European Patent Office Re. Application No. 10003540.1.

Ferguson et al. "The Effect of Different Culture Media, Glucose, Pyridine Nucleotides and Adenosine on the Activity of 11§-Hydroxysteroid Dehydrogenase in Rat Leydig Cells", Molecular and Cellular Endocrinology, XP007913033, 158(1-2): 37-44, Dec. 20, 1999.

Van Dijk et al. "Stem Cell Factor Induces Phosphatidylinositol 3'-Kinase-Dependent Lyn/Tec/Dok-1 complex Formation in Hematopoietic Cells", Hematopoiesis, 96(10): 3406-3413, 2000.

American Cyanamid "Thiotepa", Product Identification Sheet, American Cyanamid Co Lederle Laboratories Div., EM Science, p. 6505-6507, Jul. 31, 1990.

Murray et al., "Modulation of Murine Lymphocyte and Macrophage Proliferation by Parenteral Zinc", *Clinical and Experimental Immunology*, 53(3):744-749 (1983) (Abstract), p. 748, § 2-3.

Murry et al., "Haematopoietic Stem Cells Do Not Transdifferentiate Into Cardiac Myocytes in Myocardial Infarcts", *Nature*, 428:664-668 (2004).

Rosenfeld et al., "In Vivo Transfer of the Human Cystic Fibrosis Transmembrane Conductance Regulator Gene to the Airway Epithelium", *Cell*, 68:143-155 (1992).

Wu et al., "High Efficiency Electroporation of Human Umbilical Cord Blood CD34+ Hematopoietic Precursor Cells", *Stem Cells*, 19:492-499 (2001).

Tong et al., "The Effects of Copper Deficiency on Human Lymphoid and Myeloid Cells: An In Vitro Model", *British Journal of Nutrition*, XP009008949, 75:97-108 (1996).

Moore et al., "Expression of CD43 on Murine and Human Pluripotent Hematopoietic Stem Cells" *J. Immunol,*, 153(11):4978-4987 (1994).

Zhao et al., "Murine Hematopoietic Stem Cell Characterization and Its Regulation in BM Transplantation" Blood, 96:3016-3022 (2000).

Kumagai et al., "Ligation of CD38 suppresses human B lymphopoiesis", *J. Exp. Med.*, 181(3):1101-1110 (1995).

Ramsfjell et al., "Distinct requirements for optimal growth and in vitro expansion of human CD34$^+$CD38$^-$ bone marrow long-term culture-initiating cells (LTC-IC), extended LTC-IC, and murine in vivo long-term reconstituting stem cells", *Blood*, 94(12):4093-4102 (1999).

Silvennoinen et al., "CD38 Signal transduction in human B cell precursors", *J. Immunol.*, 156(1):100-107 (1996).

Todisco et al., "CD38 ligation inhibits normal and leukemic myelopoiesis", *Blood*, 95(2):535-542 (2000).

Supplementary European Search Report for EP 03 70 6871, mailed Jan. 15, 2007.

Alter, B. P., *Exper.l Hematol.*, 7(5):200-209 (1979).

Bae, et al., *J. Nurt. Biochem.*, 5:457-461 (1994).

Bae, et al., *J. Nutr.*, 123(6):997-1002 (1993).

Baum, et al., *Proc. Natl. Acad. Sci. USA*, 89:2804-2808 (1992).

Bernhard, et al., *Cancer Res.*, 55:1099-1104 (1995).

Bhatia, et al., *Proc. Natl. Acad. Sci. USA*, 94:5320-5325 (1997).

Blau, et al., *Blood*, 81(1): 227-233 (1993).

Borthwick, et al., *J. Lab. Clin. Med.*, 95(4):575-580 (1980).

Brazelton, et al., *Science*, 290:1775-1779 (2000).

Breitman, et al., *Proc. Natl. Acad. Sci. USA*, 77(5):2936-2940 (1980).

Brugger, et al., *N. Engl. J. Med.*, 333(5):283-287 (1995).

Cable, et al., *Hepatol.*, 26(6):1444-1457 (1997).

Caliaro, et al., *Int. J. Cancer*, 56:743-748 (1994).

ChemMaster Safety Data Sheet, pp. 1-4 (1999).

Cicuttini, et al., *Blood*, 80(1):102-112 (1992).

Cote, et al., *Blood*, 100(7):2586-2596 (2002).

De Bruyn, et al., *Stem Cells*, 13:281-288(1995).

Douer, et al., *Leukemia*, 14(5):874-861 (2000).
Drayson, et al., *Exp. Cell Res.*, 266(1):126-134 (2001).
Dubois, et al., *J. Pediatr. Gastroenterol. Nutr.*, 10:77-81 (1990).
Duncan, et al., *Mol. Med. Today*, 3(12):554-561 (1997).
Eipers, et al., *Blood*, 86(10):3754-3762 (1995).
Emerson, S. G., *Blood*, 87(8):3082-3088 (1996).
Ferbeyre, G., *Leukemia*, 16:1918-1926 (2002).
Fisch, et al., *Eur. J. Immunol.*, 26:505-600 (1996).
Freedman, et al., *Nat. Med.*, 2(1):46-51 (1996).
Freshney, R. I., "Culture of Animal Cell, A Manual of Basic Technique", John Wiley & Sons, Third Edition, pp. 309-311 and 327-328.
Grenda, et al., *Blood*, 100(9):3221-3228 (2002).
Heslop, et al., *Nat. Med.*, 2(5):551-555 (1996).
Hino, et al., *Biochem. Biophys. Res. Commun.*, 256(1):184-191 (1999).
Hirase, et al., *Ascta Haematol.*, 87(4):195-197 (1992).
Hottinger et al., *Eur. J. Neurosci.*, 9:1548-1551 (1997).
Kapil, et al., *Blood*, 89(10):3607-3614 (1997).
Kawa, et al., *Pigment Cell Res.*, 13(suppl. 8):73-80 (2000).
Kohroki, et al., *Leukemia Res.*, 22(5):405-412 (1998).
Koller, et al.,*Blood*, 82(2):378-384 (1993).
Krause, et al., *Cell*, 105:369-377 (2001).
Labrecque, et al., *Blood*, 92(2):607-615 (1998).
Lagasse, et al., *Nat. Med.*, 6(11):1229-1234 (2000).
Lange, et al., *Leukemia*, 10(6):943-945 (1996).
Lassila, et al., *Cell. lmmunol.*, 122(2):319-328 (1989).
Lau, et al., *J. Biol. Chem.*, 249(18):5878-5884 (1974).
Lebkowski, et al., *Blood Cells*, 20:404-410 (1994).
Leslie, el al., *Blood*, 92(12):4798-4807 (1998).
Madlambayan, et al., *J. Hematother. Stem Cell Res.*, 10:481-492 (2001).
Mezey, et al., *Science*, 290:1779-1782 (2000).
Miller, et al., *Proc. Natl. Acad. Sci. USA*, 94:13648-13653 (1997).
Moore, et al., *Blood Cells*, 20:468-481 (1994).
Morimoto, et al., *Biochem. Int.*, 28(2):313-321 (1992).
Morosetti, et al., *Blood*, 87(10):4399-4403 (1996).
Morrison, et al., *Immunity*, 1:661-673 (1994).
Morrison, et al., *Development*, 124:1929-1939 (1997).
Mueller, et al., *Blood*, 100(3):998-1007 (2002).
Munshi, et al., *J. Biol. Chem.*, 277(51):49453-49458 (2002).
Muramatsu, et al., Biochem. Biophys. Res. Commun., 285(4):891-896 (2001).
Murray, et al., *Clin. Exp. Immunol.*, 53:744-749 (1983).
Osawa, et al., *Science*, 273:242-245 (1996).
Palmiter, R. D.,*Proc. Natl. Acad. Sci. USA*, 91(4):1219-1223 (1994).
Peled, et al., *Brit. J. Hematol.*, 116:655-661 (2002).
Peled, et al., Blood, Abstract #2551 only, 40th Annual Meeting of American Society of Hematology, Miami, FL, 92(10 Suppl. 1 part 1-2):618A-619A(1998).
Percival, S. S., *Am. J. Clin. Nutr.*, 67(suppl):1064S-1068S (1998).
Percival, S. S., Nutr. Rev., 53(3):59-66 (1995).
Percival, et al., *J. Nutr.*, 122(12):2424-2429 (1992).
Perrottl, et al., *Mol. Cell. Biol.*, 15(11):6075-6087 (1995).
Petersen, et al., *Science*, 284:1168-1170 (1999).
Petti, et al., *Blood*, 100(3):1065-1067 (2002).
Petzer, et al., *J. Exp. Med.*, 183:2551-2558 (1996).
Placibello, et al., *Blood*, 89(8):2644-2653 (1997).
Podesta, et al., *FASEB J.*, 14:680-690 (2000).

Podesta, et al., *FASEB J.*, 17:310-312 (2003).
Prottl, et al., *Cancer Res.*, 56:1210-1213 (1996).
Puccetti, et al., *Cancer Res.*, 62:7050-7058 (2002).
Punzel, et al., *Leukemia*, 13(1):92-97 (1999).
Purton, et al., *Blood*, 94(2):483-495 (1999).
Purton, et al., *Blood*, 95(2):470-477 (2000).
Rosenberg, et al., *J. Nat. Cancer Inst.*, 85(8):622-632 (1993).
Ross, et al., *Analytical Chem.*, 41(13):1900-1902 (1969).
Sandstrom, et al., *Blood*, 86(3):958-970 (1995).
Schechter, et al., *Mol. Basis Blood Dis.*, 179-218 (1987).
Shimizu, et al., Pediatr Int., 41:419-422 (1999).
Sieff, et al., *Blood*, 60(3):703-713 (1982).
Siena, et al., *Exper. Hematol.*, 23:1463-1471 (1995).
Sigurdsson, et al., *J. Biol. Chem.*, 278(47):46199-46202 (2003).
Simon, et al.. *Am. J. Hematol.*, 28(3):181-183 (1988).
Sprangrude, et al., *Science*, 241:58-62 (1988).
Suda, et al., *No To Hattatsu*, English Abstract Only, 25(5):429-434 (1993).
Tashiro-Itoh, et al., *Liver*, 17(6):300-306 (1997).
Tateno, et al., *Am. J. Pathol.*, 148(2):383-392 (1996).
Tetraethylene Pentamine DOD Hazardous Material Information; 6810-00F017710 (1991).
TheMerk Index, Merc & Co., Inc., USA, Tenth Edition, p. 3742 (1983).
Thiotepa Product Identification Sheet THIOTEPA; EM Science, 6505-01-047-3872 (1990).
Trientine (Systemic), MEDLINEplus Drug Information.
Triethylenetetramine Product Identification Sheet; TETA, TX1235; EM Science, 6810-00N052879 (1991).
Ueno, et al., *Leukemia Res.*, 22(6):517-525 (1998).
Van Epps, et al., *Blood Cells.*, 20:411-423 (1994).
Vilensky et al., *Ann. Emerg. Med.*, 41:378-383 (2003).
Wasa, et al., *J. Parente. Enteral Nutr.*, 18(3):190-192 (1994).
Weissmann, I. L., *Science*, 287:1442-1446 (2000).
Wick, et al., *ALTEX*, English Abstract only, 14(2):51-56 (1997).
Williams, et al., *Blood*, 87(5):1687-1691 (1996).
Zidar, et al., *Am. J. Hematol.*, 3:177-185 (1977).
Zimmerman, et al., *J. Hematother.*, 5:247-253 (1996).
Zon, L., *Blood*, 86(8):2876-2891 (1995).
Fraser et al., "Expansion In Vitro of Retrovirally Marked Totipotent Hematopoietic Stem Cells", Blood, 76(6):1071-1078 (1990).
Lumelsky et al., "Differentiation of Embryonic Stem Cells to Insulin-Secreting Structures Similar to Pancreatic Islets", *Science*, 292(5520):1389-1394 (2001).
Otonkoski et al., "Differentiation and Maturation of Porcine Fetal Islet Cells In Vitro and After Transplantation", *Transplantation*, 68(11):1674-1683 (1999).
Otonkoski et al., "Nicotinamide Is A Potent Inducer of Endocrine Differentiation in Cultured Human Fetal Pancreatic Cells", *Journal of Clinical Investigation*, 92(3):1459-1466 (1993).
Sakai et al., "Enhanced In Vitro Maturation of Fetal Mouse Liver Cells With Oncostatin M, Nicotinamide, and Dimethyl Sulfoxide", *Cell Transplantation*, 11(5):435-441 (2002).
Zulewski et al., "Multipotent Nestin-Positive Stem Cells Isolated From Adult Pancreatic Islets Differntiate Ex Vivo Into Pancreatic Endocrine, Exocrine, and Hepatic Phenotypes", *Diabetes*, 50(3):521-533 (2001).

* cited by examiner

CD34+/38−
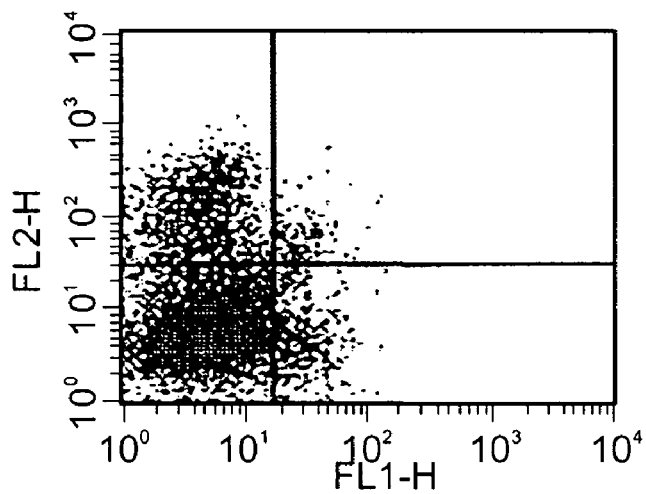
X Parameter:FL1-
Y Parameter:FL2-
| Quad | % Gated |
|---|---|
| UL | 17.14 |
| UR | 1.80 |
| LL | 75.27 |
| LR | 5.79 |
CD34+/Lin−
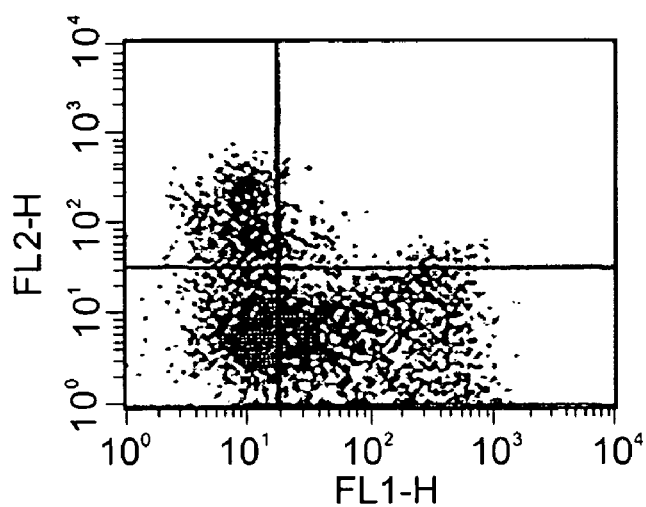
X Parameter:FL1-
Y Parameter:FL2-
| Quad | % Gated |
|---|---|
| UL | 15.58 |
| UR | 3.18 |
| LL | 30.18 |
| LR | 51.06 |
Fig. 1b

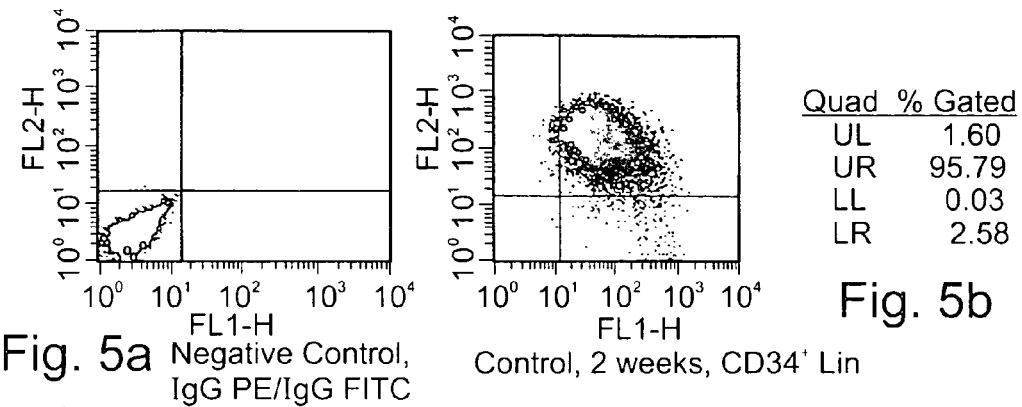
Fig. 5a Negative Control, IgG PE/IgG FITC
Fig. 5b Control, 2 weeks, CD34$^+$ Lin$^-$
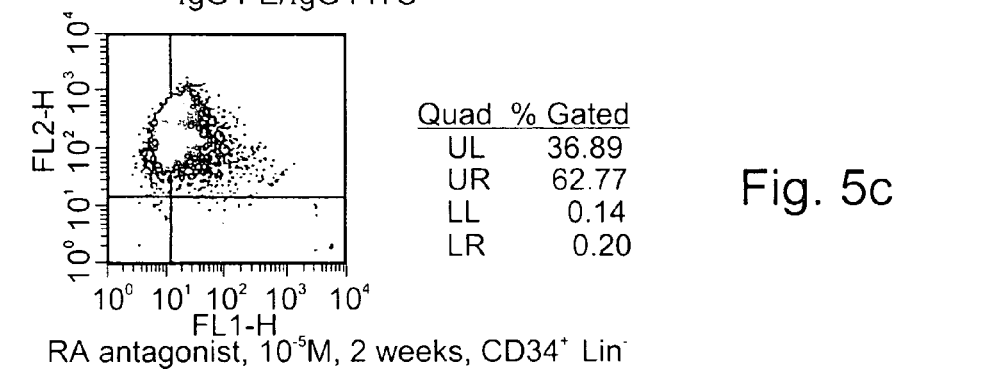
Fig. 5c RA antagonist, $10^{-5}$M, 2 weeks, CD34$^+$ Lin$^-$
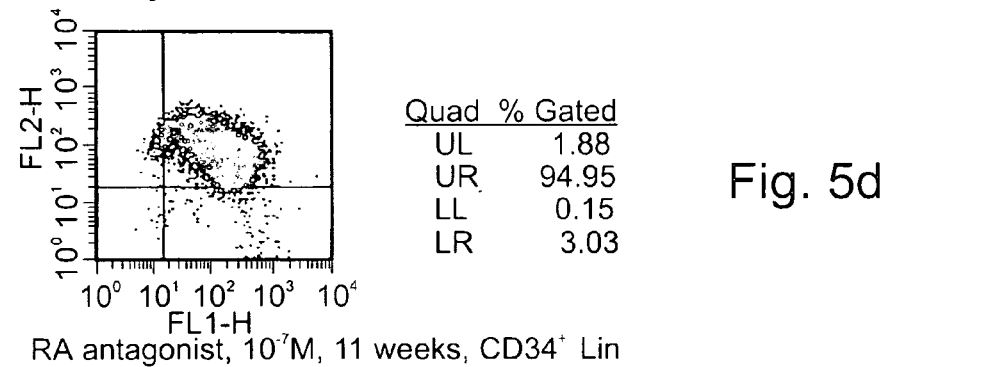
Fig. 5d RA antagonist, $10^{-7}$M, 11 weeks, CD34$^+$ Lin$^-$
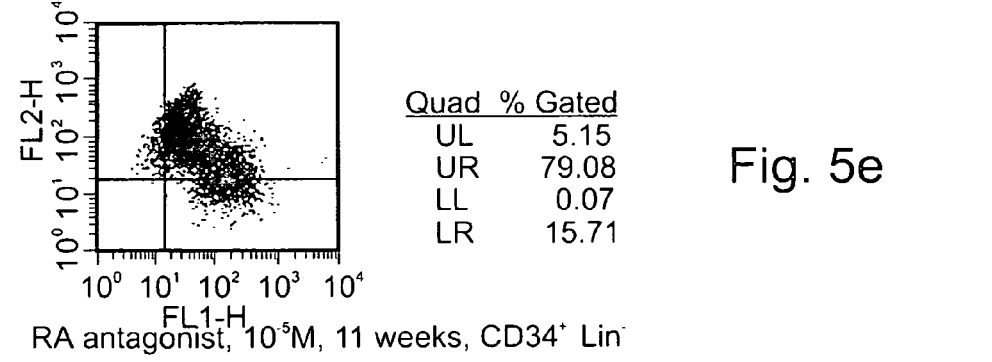
Fig. 5e RA antagonist, $10^{-5}$M, 11 weeks, CD34$^+$ Lin$^-$

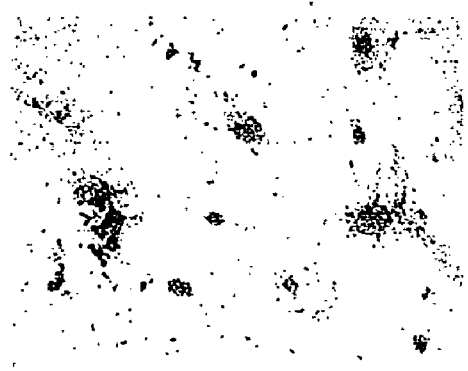 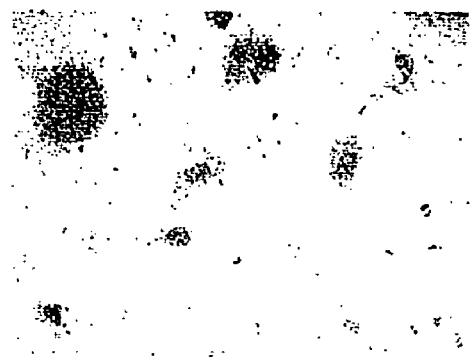
Fig. 8a　　　　　Fig. 8b
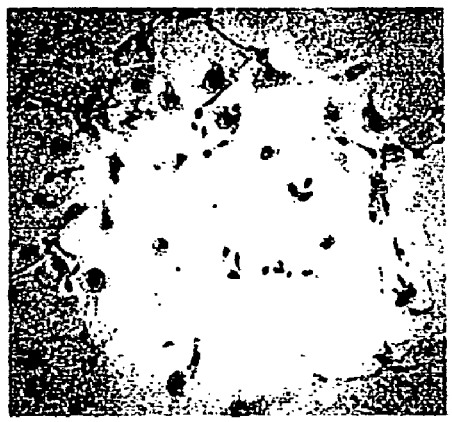 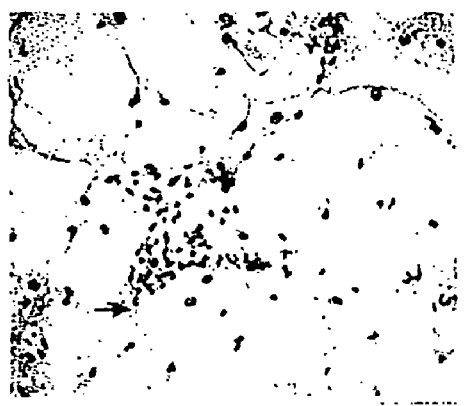
Fig. 9a　　　　　Fig.9b
Fig. 9c

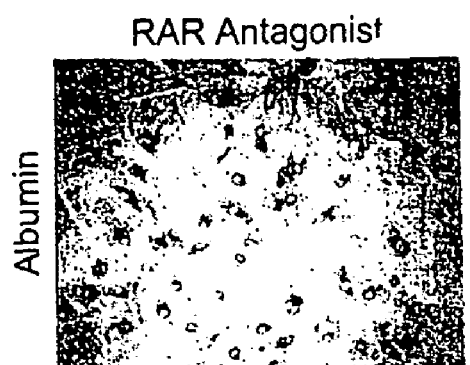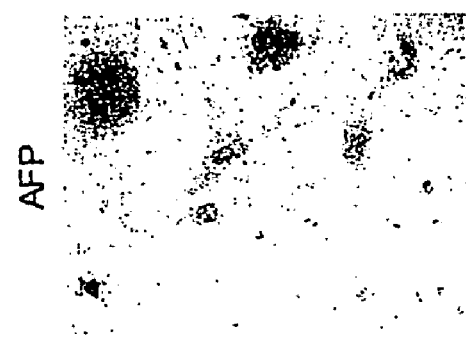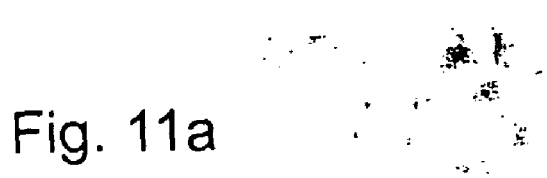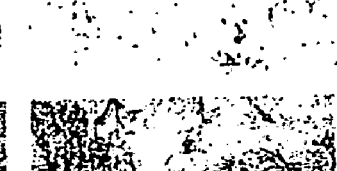

3 weeks-(34/Lin FACS analysis)
Control-cytokines only
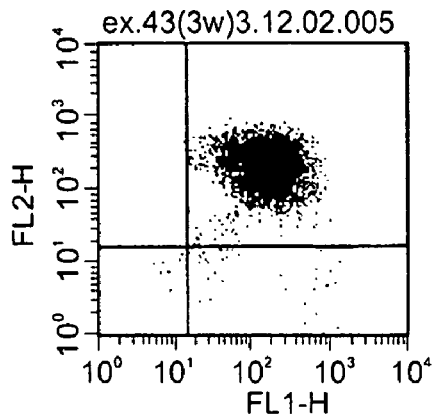
File:ex.43(3w)3.12.02.005
SampleID:
X Parameter:FL1-H(Log)
Y Parameter:FL2-H(Log)
| Quad | % Gated |
|---|---|
| UL | 0.04 |
| UR | 98.99 |
| LL | 0.22 |
| LR | 0.75 |
RAR antagonist 10-7M
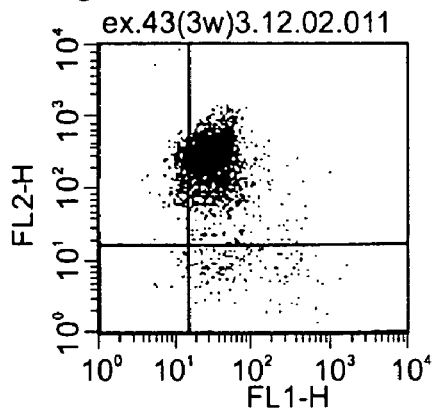
File:ex.43(3w)3.12.02.011
SampleID:
X Parameter:FL1-H(Log)
Y Parameter:FL2-H(Log)
| Quad | % Gated |
|---|---|
| UL | 8.19 |
| UR | 85.41 |
| LL | 0.44 |
| LR | 5.96 |
RAR+RXR antagonist 10-7M
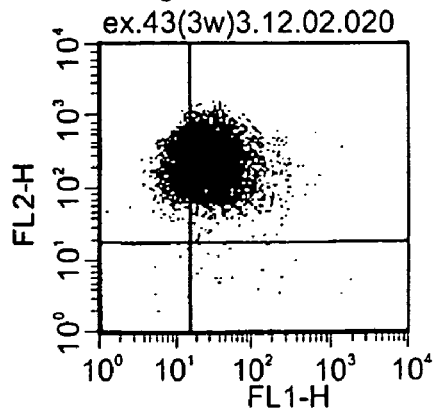
File:ex.43(3w)3.12.02.020
SampleID:
X Parameter:FL1-H(Log)
Y Parameter:FL2-H(Log)
| Quad | % Gated |
|---|---|
| UL | 19.75 |
| UR | 79.79 |
| LL | 0.09 |
| LR | 0.37 |
Fig. 12a

5 weeks-(34/Lin FACS analysis)
*Control( only cytokines) -The number of cells was not sufficient for FACS analysis.
RAR antagonist 10-7M
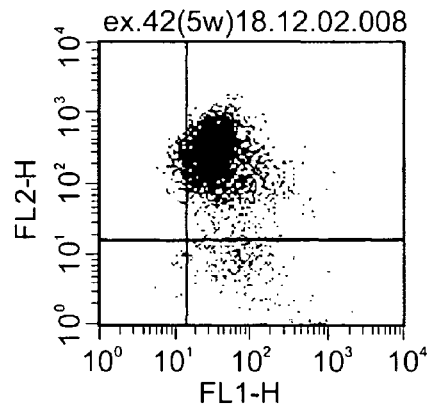
File:ex.42(5w)18.12.02.008
Sample ID:
X Parameter:FL1-H(Log)
Y Parameter:FL2-H(Log)
| Quad | % Gated |
|---|---|
| UL | 3.19 |
| UR | 91.04 |
| LL | 0.39 |
| LR | 5.37 |
RAR+RXR antagonist 10-7M
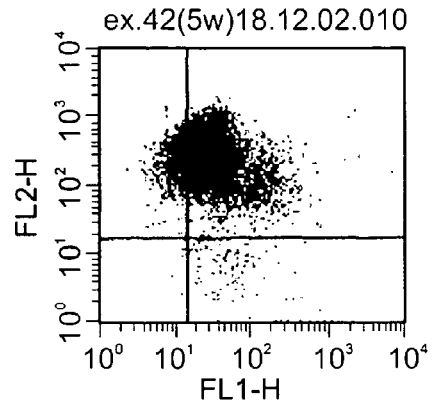
File:ex.42(5w)18.12.02.010
Sample ID:
X Parameter:FL1-H(Log)
Y Parameter:FL2-H(Log)
| Quad | % Gated |
|---|---|
| UL | 17.38 |
| UR | 81.18 |
| LL | 0.08 |
| LR | 1.36 |
Fig. 12b

FACS analysis
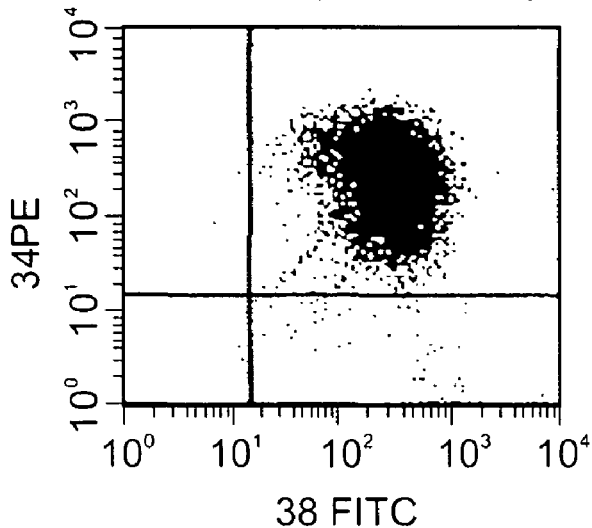
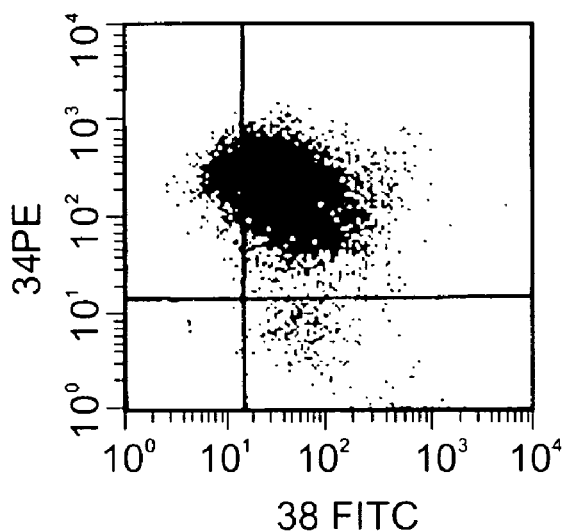
Fig. 18a

FACS analysis: CD34/Lin
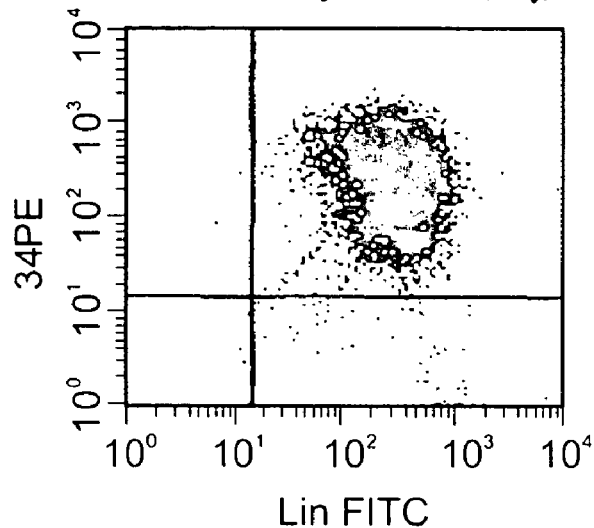
Control-cytokines only
| Quad | % Gated |
|---|---|
| UL | 0.02 |
| UR | 99.08 |
| LL | 0.05 |
| LR | 0.85 |
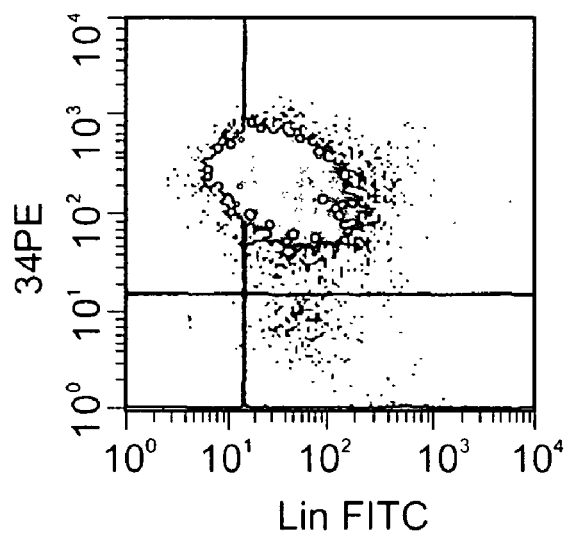
Nicotinamide 5 mM
| Quad | % Gated |
|---|---|
| UL | 16.58 |
| UR | 80.08 |
| LL | 0.05 |
| LR | 3.29 |
Fig. 18b

FACS analysis: 34/HLA-DR+38
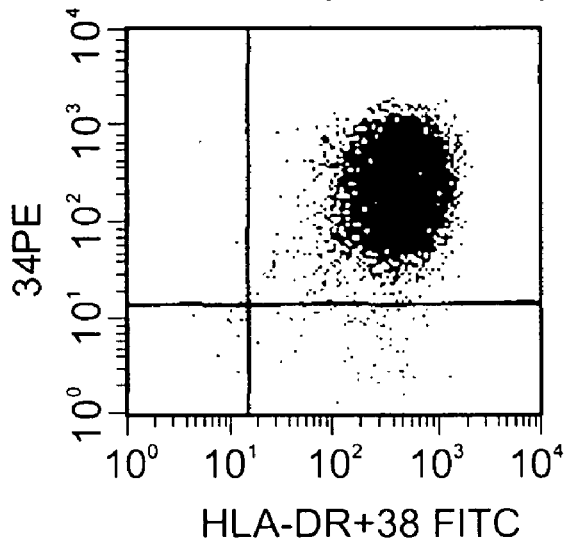
Control-cytokines only
| Quad | % Gated |
|------|---------|
| UL   | 0.02    |
| UR   | 99.02   |
| LL   | 0.12    |
| LR   | 0.84    |
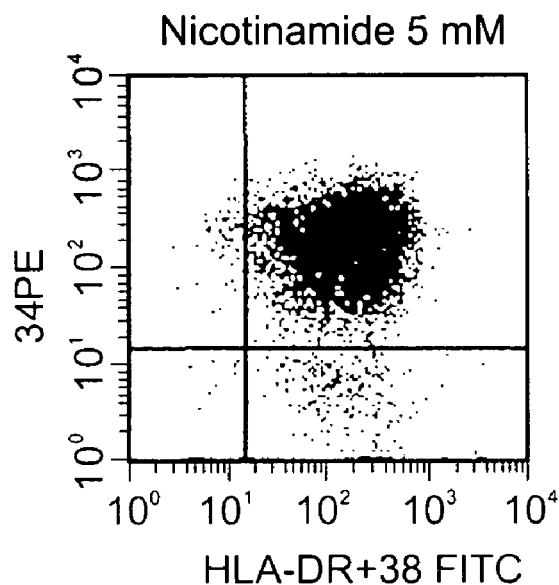
Nicotinamide 5 mM
| Quad | % Gated |
|------|---------|
| UL   | 1.02    |
| UR   | 95.43   |
| LL   | 0.16    |
| LR   | 3.39    |
Fig. 18c

EXPANSION OF RENEWABLE STEM CELL POPULATIONS

RELATED APPLICATIONS

This continuation application claims the benefit of, and priority to, under 35 USC §365(c) to PCT/IL03/00064 filed Jan. 26, 2003, which claims priority from Israel Patent Application IL152904 filed Nov. 17, 2002.

Israel Patent Application IL152904 claims the benefit of U.S. Patent Application 60/404,137 filed Aug. 19, 2002, U.S. Patent Application 60/376,183 filed Apr. 30, 2002, and U.S. Patent Application 60/350,360 filed Jan. 24, 2002. The contents of these applications are incorporated herein by reference in their entireties.

FIELD AND BACKGROUND OF THE INVENTION

The present invention relates to methods of expansion of renewable stem cells, to expanded populations of renewable stem cells and to their uses. In particular, the present invention relates to methods of reducing the expression and/or activity of CD38. In one embodiment, ex-vivo and/or in-vivo stem cell expansion is achieved according to the present invention by downregulation of retinoic acid receptor (RAR), retinoid X receptor (RXR), and/or Vitamin D receptor (VDR) signaling, either at the protein level via RAR, RXR and/or VDR antagonists or at the expression level via genetic engineering techniques, such as small interfering RNA (siRNA) techniques. In another embodiment, ex-vivo and/or in-vivo stem cell expansion is achieved according to the present invention by downregulation of CD38 either at the protein level via CD38 inhibitors, such as, for example, nicotinamide, or at the expression level via genetic engineering techniques, such as small interfering RNA (siRNA) techniques. The present invention further relates to therapeutic applications in which these methods and/or the expanded stem cells populations obtained thereby are utilized.

An increasing need for ex-vivo cultures of hematopoietic and non-hematopoietic stem cells has arisen, in particular for purposes such as stem cell expansion and retroviral-mediated gene transduction. Methods for generating ex-vivo cultures of stem cells to date, however, result in a rapid decline in stem cell population activity, further resulting in a markedly impaired self renewal potential and diminished transplantability of the cultured cell populations. The need to improve such methods is obvious. Additionally, applications in gene therapy using retroviral vectors necessitate the use of proliferating hematopoietic stem cells, yet require that these cells remain undifferentiated while in culture, in order to maintain long-term expression of the transduced gene. Thus, the ability to maintain ex-vivo cultures of hematopoietic and non-hematopoietic stem cell populations with long-term, self-renewal capacity is of critical importance for a wide array of medical therapeutic applications.

Presently, expansion of renewable stem cells have been achieved either by growing the stem cells over a feeder layer of fibroblast cells, or by growing the cells in the presence of the early acting cytokines thrombopoietin (TPO), interleukin-6 (IL-6), an FLT-3 ligand and stem cell factor (SCF) (Madlambayan G J et al (2001) J Hemather Stem Cell Res 10: 481, Punzel M et al (1999) Leukemia 13: 92, and Lange W et al (1996) Leukemia 10: 943). While expanding stem cells over a feeder layer results in vast, substantially endless cell expansion, expanding stem cells without a feeder layer, in the presence of the early acting cytokines, results in an elevated degree of differentiation (see controls described in the Examples section and Leslie N R et al (Blood (1998) 92: 4798), Petzer A L et al (1996) J Exp Med Jun 183: 2551, Kawa Y et al (2000) Pigment Cell Res 8: 73).

In any case, using present day technology, stem cells cannot be expanded unless first substantially enriched or isolated to homogeneity.

The art presently fails to teach an efficient method for expansion of renewable stem cells without a feeder layer.

CD38 is a member of an emerging family of cytosolic and membrane-bound enzymes whose substrate is nicotinamide adenine dinucleotide (NAD), a coenzyme ubiquitously distributed in nature. In human, CD38 is a 45 kDa type H transmembrane glycoprotein. Recently, it has been demonstrated that CD38 is a multifunctional enzyme that exerts both $NAD^+$ glycohydrolase activity and ADP-ribosyl cyclase activity and is thus able to produce nicotinamide, ADP-ribose (ADPR), cyclic-ADPR (cADPR) and nicotinic acid adenine dinucleotide phosphate (NAADP) from its substrates (Howard et al., 1993 Science 252:1056-1059; Lee et al., 1999 Biol. Chem. 380;785-793). The soluble domain of human CD38 catalyzes the conversion of $NAD^+$ to cyclic ADP-ribose and to ADP-ribose via a common covalent intermediate (Sauve, A. A., Deng, H. T., Angelletti, R. H., and Schramm, V. L. (2000) *J. Am. Chem. Soc.* 122, 7855-7859).

However, it was further found that CD38 is not characterized only by multi enzymatic activity but is further able to mobilize calcium, to transduce signals and to adhere to hyaluronan and to other ligands. Interaction with CD38 on various leukocyte subpopulation has profound though diverse effects on their life-span (Funaro A, Malavasi F *J Biol Regul Homeost Agents* 1999 January-March;13(1):54-61 Human CD38, a surface receptor, an enzyme, an adhesion molecule and not a simple marker).

CD38 is widely expressed in both hematopoietic and non hematopoietically-derived cells. Homologues of CD38 have also been found to be expressed in mammalian stromal cells (Bst-1) and in cells isolated from the invertebrate Aplysia californica (Prasad G S, 1996, nature Structural Biol 3:957-964).

Two of the metabolites produced by CD38, cADPR and NAADP, have been shown to induce the release of intracellular calcium in cells isolated from tissues of plants, invertebrates and mammals, suggesting that these metabolites may be global regulators of calcium responses (Lee et al., 1999 Biol. Chem. 380;785-793). Both cADPR and NAADP are known to induce calcium release from calcium stores that are distinct from those controlled by $Ip^3$ receptors (Clapper, D L et al., 1987, J. Biological Chem. 262:9561-9568).

Hence, CD38, being the best-characterized mammalian ADP-ribosyl cyclase, is postulated to be an important source of cyclic ADP-ribose in vivo.

Nucleoplasmic calcium ions ($Ca^{+2}$) influence highly important nuclear functions such as gene transcription, apoptosis, DNA repair, topoisomerase activation and polymerase unfolding. Although both inositol trisphosphate receptors and ryanodine receptors, which are types of $Ca^{+2}$ channel, are present in the nuclear membrane, their role in the homeostasis of nuclear $Ca^{+2}$ is still unclear.

It was found that CD38/ADP-ribosyl cyclase has its catalytic site within the nucleoplasm and hence it catalyses the intranuclear cyclization of $NAD^+$, to produce nucleoplasmic cADPR. The latter activates ryanodine receptors of the inner nuclear membrane to trigger nucleoplasmic $Ca^{+2}$ release (Adebanjo O A et al. *Nat Cell Biol* 1999 November;1(7):409-14 A new function for CD38/ADP-ribosyl cyclase in nuclear Ca2+ homeostasis).

It was further found that agonists of ryanodine receptors sensitize cADPR-mediated calcium release and antagonists of ryanodine receptors block cADPR-dependent calcium release (Galione A et al., 1991, Science 253:143-146). Thus, it has been proposed that cADPR is likely to regulate calcium responses in tissues such as muscle and pancreas, where ryanodine receptors are expressed (Day et al., 2000 Parasitol 120:417-422; Silva et al., 1998, Biochem. Pharmacol 56:997-1003). It has been also shown that in mammalian smooth muscle cells, the calcium release in response to acetylcholine can be blocked not only with ryanodine receptor antagonists, but also with specific antagonists of cADPR such as $8-NH_2$-cADPR or 8-Br-cADPR (Guse, A H, 1999, Cell. Signal. 11:309-316). These findings, as well as others, indicate that ryanodine receptor agonists/antagonists such as cADPR can regulate calcium responses in cells isolated from diverse species.

As is discussed hereinabove, self-renewal of hemopoietic stem and progenitor cells (HPC), both in vivo and in vitro, is limited by cell differentiation. Differentiation in the hematopoietic system involves, among other changes, altered expression of surface antigens (Sieff C, Bicknell D, Caine G, Robinson J, Lam G, Greaves M F (1982) Changes in cell surface antigen expression during hematopoietic differentiation. *Blood* 60:703). In normal human, most of the hematopoietic pluripotent stem cells and the lineage committed progenitor cells are CD34+. The majority of cells are CD34+ CD38+, with a minority of cells (<10%) being CD34+ CD38−. The CD34+CD38− phenotype appears to identify the most immature hematopoietic cells, which are capable of self-renewal and multilineage differentiation. The CD34+ CD38− cell fraction contains more long-term culture initiating cells (LTC-IC) pre-CFU and exhibits longer maintenance of their phenotype and delayed proliferative response to cytokines as compared with CD34+CD38+cells. CD34+ CD38− can give rise to lymphoid and myeloid cells in vitro and have an enhanced capacity to repopulate SCID mice (Bhatia M, Wang JCY, Kapp U, Bonnet D, Dick J E (1997) Purification of primitive human hematopoietic cells capable of repopulating immune-deficient mice. *Proc Natl Acad Sci USA* 94:5320). Moreover, in patients who received autologous blood cell transplantation, the number of CD34+CD38− cells infused correlated positively with the speed of hematopoietic recovery. In line with these functional features, CD34+CD38− cells have been shown to have detectable levels of telomerase.

Recently, it has been reported that granulocytic differentiation of human HL-60 cells (a committed cell line) can be induced by retinoic acid and is accompanied by a massive expression of CD38. Concomitant with CD38 expression was the accumulation of cADPR, and both time courses preceded the onset of differentiation, suggesting a causal role for CD38. Consistently, treatment of HL-60 cells with a permeant inhibitor of CD38, nicotinamide, inhibited both the CD38 activity and differentiation. More specific blockage of CD38 expression was achieved by using morpholino antisense oligonucleotides targeting its mRNA, which produced a corresponding inhibition of differentiation as well (Munshi C B, Graeff R, Lee H C, *J Biol Chem* 2002 Dec. 20;277(51): 49453-8).

In view of the findings described above with respect to the effect of CD38 on cADPR and ryanodine signal transduction pathways and hence on cell expansion and differentiation, the present inventors have envisioned that by modulating the expression and/or the activity of CD38, the expansion and differentiation of stem cells could be controlled. In particular, it was hypothesized that by reducing the expression and/or the activity of CD38, using agents that downregulate the expression of CD38 or inhibit the activity thereof, expansion of renewable stem cells, devoid of differentiation, would be achievable.

Nicotinamide (NA) is a water-soluble derivative of vitamin B, whose physiological active forms are nicotinamide adenine dinucleotide (NAD+/NADH) and nicotinamide adenine dinucleotide phosphate (NADP+/NADPH). The physiological active forms of NA serve as coenzyme in a variety of important metabolic reactions. Nicotinamide is further known to inhibit the enzymatic activity of CD38, to thereby affect the cADPR signal transduction pathway, a feature which is demonstrated, for example, in the studies described hereinabove (see, for example, Munshi C B, Graeff R, Lee H C, *J Biol Chem* 2002 Dec. 20;277(51):49453-8).

Hence, while conceiving the present invention, it was hypothesized that nicotinamide, as well as other agents known to inhibit the enzymatic activity of CD38, can be utilized for expanding stem cell populations while inhibiting the differentiation of the stem cells. It was further hypothesized that other small molecules, which are capable of interfering, directly or indirectly, with the expression of CD38 can be similarly used.

Retinoic acid (RA), the natural acidic derivative of Vitamin A (retinol) is an important regulator of embryonic development and it also influences the growth and differentiation of a wide variety of adult cell types. The biological effects of RA are generally mediated through their interaction with specific ligand-activated nuclear transcription factors, their cognate RA receptors (RARs). Receptors of the retinoic acid family comprise RARS, RXRs, Vitamin D receptors (VDRs), thyroid hormone receptors (THRs) and others. When activated by specific ligands these receptors behave as transcription factors, controlling gene expression during embryonic and adult development. The RAR and RXR families of receptors uniquely exhibit modular structures harboring distinct DNA-binding and ligand-binding domains. These receptors probably mediate their biological effects by binding to regulatory elements (e.g., retinoic acid response elements, or RAREs) as RAR-RXR heterodimers that are present in the promoters of their specific target genes (1, 2, 3).

Retinoid receptors thus behave as ligand-dependent transcriptional regulators, repressing transcription in the absence of ligand and activating transcription in its presence. These divergent effects on transcription are mediated through the recruitment of co-regulators: un-liganded receptors bind corepressors (NCOR and SMRT) that are found within a complex exhibiting histone deacetylase (HDAC) activity, whereas liganded receptors recruit co-activators with histone acetylase activity (HATs). Chromatin remodeling may also be required, suggesting a hierarchy of promoter structure modifications in RA target genes carried out by multiple co-regulatory complexes.

The first retinoic acid receptor identified, designated RAR-alpha, modulates transcription of specific target genes in a manner which is ligand-dependent, as subsequently shown for many of the members of the steroid/thyroid hormone intracellular receptor superfamily. The endogenous low-molecular-weight ligand, upon which the transcription-modulating activity of RAR-alpha depends, is all-trans-retinoic acid. Retinoic acid receptor-mediated changes in gene expression result in characteristic alterations in cellular phenotype, affecting multiple tissues. Additional RAR-alpha related genes have been identified, designated RAR-beta and RAR-gamma, and exhibit a high level of homology to RAR-alpha and each other (4, 5). The ligand-binding region of the three RAR subtype receptors has a primary amino acid sequence divergence of less than 15%.

Similarly, additional members of the steroid/thyroid receptor superfamily responsive to retinoic acid have been identified (6), and have been designated as the retinoid X receptor (RXR) family. Like the RARs, the RXRs are also known to comprise at least three subtypes or isoforms, namely RXR-alpha, RXR-beta, and RXR-gamma, with corresponding unique patterns of expression (7).

Although both the RARs and RXRs bind the ligand all-trans-retinoic acid in vivo, the receptors differ in several important aspects. First, the RARs and RXRs significantly differ in their primary structure, especially regarding their ligand binding domains (e.g., alpha domains exhibit a mere 27% shared amino acid identity). These structural differences manifest in their differing relative degrees of responsiveness to various Vitamin A metabolites and synthetic retinoids. Additionally, tissue distribution patterns are distinctly different for RARs and RXRs. RARs and RXRs exhibit different target gene specificity. One example is regarding the cellular retinal binding protein type II (CRBPII) and apolipoprotein AI proteins that confer responsiveness to RXR, but not RAR. Furthermore, RAR has also been shown to repress RXR-mediated activation through the CRBPII RXR response element (8). These data indicate that the two separate retinoic acid responsive pathways are not simply redundant, but instead manifest a complex interplay.

Vitamin D (VitD) is an additional potent activator of one of the receptors belonging to the retinoid receptor superfamily. The nuclear hormone 1 alpha, 25-dihydroxyvitamin D (3) (1 alpha, 25 (OH) (2) D (3)) binds its cognate receptor (VDR) and acts as a transcription factor when in combined contact with the retinoid X receptor (RXR), coactivator proteins, and specific DNA binding sites (VDREs). Ligand-mediated conformational changes of the VDR comprise the molecular switch controlling nuclear 1 alpha, 25 (OH) (2) D (3), signaling events.

Cell-specific VDR antagonists reveal the exquisite control and regulation of the pleiotropic 1 alpha, 25 (OH) (2) D (3) endocrine system, with consequences in maintenance of calcium homeostasis, bone mineralization and other cellular functions. Antagonists to VitD were shown to act via the same mechanism: they selectively stabilize an antagonistic conformation of the ligand-binding domain of the VDR within VDR-RXR-VDRE complexes, inhibiting the interaction of the VDR with coactivator proteins and induction of transactivation. Interestingly, cells treated with VitD antagonists contain VDR-RXR heterodimers in different conformations as compared to cells stimulated with VitD agonists (16).

Retinoic acid and VitD can cooperatively stimulate transcriptional events involving a common DNA binding site or hormone response element (HRE). Conversely, VDR/RXR heterodimers have been found to bind without defined polarity and in a transcriptionally unproductive manner to certain RA response elements, and under these circumstances Vitamin D inhibits the response to RA. Although competition for binding to DNA may contribute to this inhibitory response, titration of common coactivators by VDR also appears to be involved in this trans-repression. Therefore, the regulation of the transcriptional response to RA and VitD is dependent upon a complex combinatory pattern of interaction among the different receptors, co-activators (17) and their binding to the appropriate DNA binding sites.

In parallel to their function as transcriptional regulators, retinoid receptors such as RAR and RXR play important roles in regulating the growth and differentiation of a variety of cell-types, as well (18). RAR agonists such as all-trans-retinoic acid (ATRA) are predominantly known for their effects in inducing cell-differentiation, as seen in experiments utilizing malignant cancer cells and embryonic stem cells (19), where potent induction of terminal differentiation was evident. Cell differentiation is not an exclusive result, however, as RA has been shown to exhibit different effects on cultured hematopoietic cells, depending on their maturational state (20). While retinoids accelerated the growth and differentiation of granulocyte progenitors in cytokine-stimulated cultures of purified $CD34^+$ cells, use of stem cells produced an opposite effect (42). Retinoid treatment has also been shown to inhibit differentiation of pre-adipose cells (43).

Whereas the RAR antagonist AGN 193109 exerted a positive effect on the differentiation of hematopoietic stem cells (41) the RAR agonist 4-[4-(4-ethylphenyl)dimethyl-chromen-yl]ethynyl}-benzoic acid] functions in an opposing manner. Conversely, RAR antagonists have been shown to prevent granulocytic differentiation in experiments utilizing the promyelocytic cell line, HL-60 (41). Similarly, creation of myeloid cell lines defective in signaling through their retinoid receptors do not undergo granulocytic differentiation in the presence of G-CSF (22), and retinoid-deficient tissues acquire a pre-malignant phenotype, and a concomitant loss of differentiation (29, 30). Malignant cell lines derived from various carcinomas exhibit diminished expression of retinoic acid receptor mRNA, implying that the loss of expression may be an important event in tumorogenesis (33, 34, 35, 36, 37). Furthermore, disruption of retinoic acid receptor activity, as evidenced in knock-out mouse models disrupted for the RAR gene, display an in vitro block to granulocytic differentiation (38, 39).

However, other studies using a similar approach have resulted in the development of hematopoietic cell lines (23). The hematopoietic stem and early progenitor cells are characterized by their surface expression of the surface antigen marker known as $CD34^+$, and exclusion of expression of the surface lineage antigen markers, $Lin^-$. Experiments utilizing several leukemia cell lines revealed that retinoic acid receptor mediated signaling results in the induction of expression of the differentiation marker CD38 cell surface antigen whereas antagonists to RAR abolished CD38 antigen up-regulation (24, 25).

Therefore, to date, the data are conflicting as to definitive roles for VitD and RA in induction of myelomonocytic and promyelocytic cell differentiation, or prevention of these processes. Although some previous studies with inactivation of RAR, RXR and VDR using antagonists, antisense technology or transduction methods with truncated receptors, yielded inhibited granulocytic and monocytic differentiation, these studies were conducted using leukemia cell lines that are blocked at the myeloblast or promyelocytic stage of differentiation (19, 22, 64). As stated above, isolation procedures for hematopoietic and other stem cells result in small populations of cells that are difficult to expand in ex-vivo cultures. Current culture methods enable large-scale expansion of progenitor and differentiated cell populations, but provide minimal amplification of the stem cell component. Applications and uses of stem cell populations for cell replacement therapy, in-vivo tissue regeneration, ex-vivo tissue formation and gene therapy, necessitate the acquirement of large numbers of these cell populations.

There is thus a widely recognized need for, and it would be highly advantageous to have, a method of propagating large numbers of stem cells in an ex-vivo setting. Methods enabling ex-vivo expansion of stem cell compartments yielding large numbers of these cell populations will therefore pioneer feasible stem cell therapies for human treatment, with a clear and direct impact on the treatment of an infinite number of pathologies and diseases.

Some pathological and medically induced conditions are characterized by a low number of in-vivo self or transplanted renewable stem cells, in which conditions, it will be advantageous to have an agent which can induce stem cell expansion in-vivo.

SUMMARY OF THE INVENTION

The present invention discloses the use of various molecules for interfering with CD38 expression and/or activity, thereby inducing ex-vivo and/or in-vivo expansion of stem cell populations, resulting, when applied, for example, to hematopoietic stem cells, in large numbers of undifferentiated CD34$^+$/Lin$^-$ (CD33, CD14, CD15, CD4, etc.), as well as CD34$^+$/CD38$^-$ cells, especially CD34$^+_{dim}$/Lin$^-$ cells.

This novel and versatile technology may be used for ex-vivo and in-vivo expansion of stem cells, of hematopoietic and other origins, maintaining their self-renewal potential for any in-vivo or ex-vivo application which requires large numbers of stem cell populations.

While reducing the present invention to practice, it was unexpectedly found that nicotinamide, a well-known CD38 inhibitor, represses the process of differentiation of stem cells and stimulates and prolongs the phase of active cell proliferation and expansion of the cells ex-vivo. It was further unexpectedly found that a series of chemical agents, retinoic acid receptor antagonists of the RAR and RXR superfamilies, and Vitamin D receptor antagonists, which have been shown to affect CD38 expression, also repress the process of differentiation of stem cells and stimulates and prolongs, for up to 16-18 weeks, the phase of active cell proliferation and expansion ex-vivo.

These unexpected effects were surprisingly obtained when the source of cells was CD34$^+$ enriched hematopoietic cells (stem and early progenitor cells) and, most surprisingly, when the source of cells included the entire fraction of mononuclear blood cells (whole fraction of white blood cells, which includes stem, progenitor and committed cells).

Equally unexpected was the finding that primary hepatocyte cultures incubated with the antagonists described above revealed an increase in the proportion of cells producing α-fetoprotein, hence signaling the proliferation of early hepatocytes. Supplementation of hepatocyte cultures with growth factors alone was not sufficient to stimulate proliferation of early hepatocyte populations, though growth factor supplemented RAR antagonist treated cultures responded similarly to unsupplemented RAR antagonist treated cultures. Furthermore, first passage of growth factor supplemented RAR antagonist treated cultures revealed the presence of a large proportion of oval cells, indicative of hepatocyte progenitor cells, while supplemented untreated cultures did not result in evidence of oval cell populations, hence following second passage revealed dramatically reduced numbers of hepatocytes. Thus only the presence of the RAR antagonist is sufficient to stimulate hepatocyte cell expansion.

This newly discovered effect of the nicotinamide as well as of the receptor antagonists of the RAR, RXR and VDR superfamilies, was used for maximizing the ex-vivo expansion of various types of cells as is further detailed hereinunder.

It is one object of the present invention to provide a method of ex-vivo expanding a population of stem cells, while at the same time substantially inhibiting ex-vivo differentiation of the stem cells.

It is another object of the present invention to provide a method of in-vivo expanding a population of stem cells, while at the same time substantially inhibiting in-vivo differentiation of the stem cells, thereby inducing in-vivo renewal of the stem cells.

It is yet another object of the present invention to use the expanded stem cells in different applications, including, but not limited to, post expansion cis-differentiation, post expansion trans-differentiation, post expansion genetic modulation, post expansion transplantations, post expansion implantations, adoptive immunotherapy and the like.

It is hence another more specific object of the present invention to provide a method of hematopoietic cells transplantation or implantation.

It is still another more specific object of the present invention to provide a method of genetically modifying stem cells with an exogene.

It is yet another object of the present invention to provide a method of adoptive immunotherapy.

It is an additional object of the present invention to provide a method of mobilization of bone marrow stem cells into the peripheral blood of a donor for harvesting the cells.

It is still an additional object of the present invention to provide a method of preservation of stem cells.

It is a further object of the present invention to provide stem cell collection bags.

It is still a further object of the present invention to provide assays of determining whether a specific retinoic acid receptor antagonist is suitable for inducing ex-vivo and/or in-vivo stem cell expansion.

It is still a further object of the present invention to provide assays of determining whether a specific retinoid X receptor antagonist is suitable for inducing ex-vivo and/or in-vivo stem cell expansion.

It is still a further object of the present invention to provide assays of determining whether a specific Vitamin D receptor antagonist is suitable for inducing ex-vivo and/or in-vivo stem cell expansion.

It is still a further object of the present invention to provide assays of determining whether specific signaling through retinoic acid receptors is suitable for inducing ex-vivo and/or in-vivo stem cell expansion.

It is still a further object of the present invention to provide assays of determining whether specific signaling through retinoid X receptors is suitable for inducing ex-vivo and/or in-vivo stem cell expansion.

It is still a further object of the present invention to provide assays of determining whether signaling specific through Vitamin D receptors is suitable for inducing ex-vivo and/or in-vivo stem cell expansion.

According to one aspect of the present invention, there is provided an assay of determining whether a retinoic acid receptor antagonist, a retinoid X receptor antagonist or a Vitamin D receptor antagonist is an effective cell expansion agent. The assay comprising culturing a population of stem cells or cells of a substantially non-differentiated cell line, in the presence of the retinoic acid receptor antagonist, the retinoid X receptor antagonist or the Vitamin D receptor antagonist and monitoring expansion of the cells, wherein if increased expansion and decreased differentiation occurs, as compared to non-treated cells, the retinoic acid receptor antagonist, the retinoid X receptor antagonist or the Vitamin D receptor antagonist is an effective cell expansion agent. Preferably, culturing the population of stem cells or cells of a substantially non-differentiated cell line is performed in a presence of an effective amount of a cytokine, preferably, an early acting cytokine. This assay can be used, by one ordinarily skilled in the art, to determine which of the antagonists listed below is most efficient for the purpose of implementing the various methods, preparations and articles-of-manufacture of the present invention which are further described hereinafter.

According to another aspect of the present invention there is provided a method of ex-vivo expanding a population of stem cells, while at the same time, substantially inhibiting differentiation of the stem cells ex-vivo.

In one embodiment, the method comprises providing the stem cells with ex-vivo culture conditions for ex-vivo cell proliferation and, at the same time, for reducing the activity and/or expression of CD38, thereby expanding the population of stem cells while at the same time, substantially inhibiting differentiation of the stem cells ex-vivo.

In another embodiment the method comprises providing the stem cells with ex-vivo culture conditions for ex-vivo cell proliferation and, at the same time, for reducing a capacity of the stem cells in responding to retinoic acid, retinoids and/or Vitamin D, thereby expanding the population of stem cells while at the same time, substantially inhibiting differentiation of the stem cells ex-vivo.

In still another embodiment the method comprises providing the stem cells with ex-vivo culture conditions for ex-vivo cell proliferation and, at the same time, for reducing a capacity of the stem cells in responding to signaling pathways involving the retinoic acid receptor, retinoid-X receptor and/or Vitamin D receptor, thereby expanding the population of stem cells while at the same time, substantially inhibiting differentiation of the stem cells ex-vivo.

In yet another embodiment, the method comprises providing the stem cells with ex-vivo culture conditions for ex-vivo cell proliferation and, at the same time, with nicotinamide, a nicotinamide analog, a nicotinamide or a nicotinamide analog derivative or a nicotinamide or a nicotinamide analog metabolite, thereby expanding the population of stem cells while at the same time, substantially inhibiting differentiation of the stem cells ex-vivo.

According to another aspect of the present invention there is provided a method of in-vivo expanding a population of stem cells, while at the same time, substantially inhibiting differentiation of the stem cells in-vivo.

In one embodiment, the method comprises administering to a subject in need thereof a therapeutically effective amount of an agent, the agent serves for reducing an expression and/or activity of CD38.

In another embodiment, the method comprises administering to a subject in need thereof a therapeutically effective amount of an agent, the agent serves for reducing a capacity of the stem cells in responding to retinoic acid, retinoids and/or Vitamin D.

In still another embodiment, the method comprises administering to a subject in need thereof a therapeutically effective amount of an agent, the agent serves for reducing a capacity of the stem cells in responding to signaling pathways involving the retinoic acid receptor, retinoid-X receptor and/or Vitamin D receptor.

In yet another the method comprises administering to a subject in need thereof a therapeutically effective amount of an agent selected from the group consisting of nicotinamide, a nicotinamide analog, a nicotinamide or a nicotinamide analog derivative and a nicotinamide or a nicotinamide analog metabolite.

According to yet another aspect of the present invention there is provided a method of ex-vivo expanding a population of hematopoietic renewable stem cells ex-vivo.

In one embodiment, the method comprises obtaining adult or neonatal umbilical cord whole white blood cells or whole bone marrow cells sample and providing the cells in the sample with ex-vivo culture conditions for stem cells ex-vivo cell proliferation and, at the same time, for reducing the expression and/or activity of CD38, thereby expanding a population of a renewable stem cells in the sample.

In another embodiment, the method comprises obtaining adult or neonatal umbilical cord whole white blood cells or whole bone marrow cells sample and providing the cells in the sample with ex-vivo culture conditions for stem cells ex-vivo cell proliferation and, at the same time, for reducing a capacity of the stem cells in responding to retinoic acid, retinoids and/or Vitamin D, thereby expanding a population of a renewable stem cells in the sample.

In still another embodiment, the method comprises obtaining adult or neonatal umbilical cord whole white blood cells or whole bone marrow cells sample and providing the cells in the sample with ex-vivo culture conditions for stem cells ex-vivo cell proliferation and, at the same time, for reducing a capacity of the stem cells in responding to signaling pathways involving the retinoic acid receptor, the retinoid X receptor and/or the Vitamin D receptor, thereby expanding a population of a renewable stem cells in the sample.

In yet another embodiment, the method comprises obtaining adult or neonatal umbilical cord whole white blood cells or whole bone marrow cells sample and providing the cells in the sample with ex-vivo culture conditions for stem cells ex-vivo cell proliferation and, at the same time, with nicotinamide, a nicotinamide analog, a nicotinamide or a nicotinamide analog derivative or a nicotinamide or a nicotinamide analog metabolite, thereby expanding a population of a renewable stem cells in the sample.

Further according to an aspect of the present invention, there is provided a method of genetically modifying stem cells with an exogene.

In one embodiment, the method comprises (a) obtaining stem cells to be genetically modified; (b) providing the stem cells with ex-vivo culture conditions for cell proliferation and, at the same time, for reducing the expression and/or activity of CD38, while at the same time, substantially inhibiting differentiation of the stem cells ex-vivo; and (c) genetically modifying the stem cells with the exogene.

In another embodiment, the method comprises (a) obtaining stem cells to be genetically modified; (b) providing the stem cells with ex-vivo culture conditions for cell proliferation and, at the same time, for reducing a capacity of the stem cells in responding to retinoic acid, retinoids and/or Vitamin D, thereby expanding a population of the stem cells, while at the same time, substantially inhibiting differentiation of the stem cells ex-vivo; and (c) genetically modifying the stem cells with the exogene.

In still another embodiment, the method comprises (a) obtaining stem cells to be genetically modified; (b) providing the stem cells with ex-vivo culture conditions for cell proliferation and, at the same time, for reducing a capacity of the stem cells in responding to signaling pathways involving the retinoic acid receptor and/or the retinoid X receptor and/or the Vitamin D receptor, thereby expanding a population of the stem cells, while at the same time, substantially inhibiting differentiation of the stem cells ex-vivo; and (c) genetically modifying the stem cells with the exogene.

In yet another embodiment, the method comprises (a) obtaining stem cells to be genetically modified; (b) providing the stem cells with ex-vivo culture conditions for cell proliferation and with nicotinamide, a nicotinamide analog, a nicotinamide or a nicotinamide analog derivative or a nicotinamide or a nicotinamide analog metabolite, thereby expanding a population of the stem cells, while at the same time, substantially inhibiting differentiation of the stem cells ex-vivo; and (c) genetically modifying the stem cells with the exogene.

In a preferred embodiment, genetically modifying the cells is effected by a vector, which comprises the exogene, which vector is, for example, a viral vector or a nucleic acid vector.

According to still another aspect of the present invention there are provided transplantable hematopoietic cell preparations.

In one embodiment, a transplantable hematopoietic cell preparation of the present invention comprises an expanded population of hematopoietic stem cells propagated ex-vivo in the presence of an effective amount of an agent, the agent reducing an expression and/or activity of CD38, while at the same time, substantially inhibiting differentiation of the stem cells; and a pharmaceutically acceptable carrier.

In another embodiment, a transplantable hematopoietic cell preparation of the present invention comprise an expanded population of hematopoietic stem cells propagated ex-vivo in the presence of an effective amount of an agent, the agent reducing a capacity of the stem cells in responding to retinoic acid, retinoids and/or Vitamin D, while at the same time, substantially inhibiting differentiation of the stem cells; and a pharmaceutically acceptable carrier.

In still another embodiment, a transplantable hematopoietic cell preparation of the present invention comprises an expanded population of hematopoietic stem cells propagated ex-vivo in the presence of an effective amount of an agent, the agent reducing a capacity of the stem cells in responding to retinoic acid receptor, retinoid X receptor and/or Vitamin D receptor signaling, while at the same time, substantially inhibiting differentiation of the stem cells; and a pharmaceutically acceptable carrier.

In yet another embodiment, a transplantable hematopoietic cell preparation of the present invention comprises an expanded population of hematopoietic stem cells propagated ex-vivo in the presence of an effective amount of an agent selected from the group consisting of nicotinamide, a nicotinamide analog, a nicotinamide or a nicotinamide analog derivative and a nicotinamide or a nicotinamide analog metabolite, while at the same time, substantially inhibiting differentiation of the stem cells; and a pharmaceutically acceptable carrier.

Further according to an aspect of the present invention there is provided an ex-vivo expanded population of hematopoietic stem cells, comprising a plurality of cells characterized by 3-20% of the cells being reselectable for CD34$^+$ cells, of which at least 40% of cells are CD34$^+_{dim}$, wherein, in the reselectable CD34$^+$ cells, a majority of cells which are Lin$^-$ are also CD34$^+_{dim}$ cells. In one embodiment, the hematopoietic stem cells are derived from a source selected from the group consisting of bone marrow, peripheral blood and neonatal umbilical cord blood. In another embodiment, the population of cells has a single genetic background. In yet another embodiment, the ex-vivo expanded population of hematopoietic stem cells comprises at least N cells derived from a single donor, wherein N equals the average number of CD34$^+$ cells derived from one sample of neonatal umbilical cord blood, bone marrow, or peripheral blood multiplied by 1,000. Cell surface expression of the CD34 and/or Lin markers can be determined, for example, via FACS analysis or immunohistological staining techniques. A self renewal potential of the stem cells can be determined by long term colony formation (LTC-CFUc) or by in vivo engraftment in a SCID-Hu mouse model.

According to a further aspect of the present invention there is provided a method of preserving stem cells comprising handling the stem cell in at least one of the steps selected from the group consisting of harvest, isolation and storage, in a presence of an effective amount of a retinoic acid receptor antagonist, a retinoid X receptor antagonist and/or a Vitamin D receptor antagonist. Alternatively, the method comprises handling the stem cell in at least one of the steps selected from the group consisting of harvest, isolation and storage, in a presence of an effective amount of nicotinamide, a nicotinamide analog, a nicotinamide or a nicotinamide analog derivative or a nicotinamide or a nicotinamide analog metabolite.

According to still a further aspect of the present invention there is provided a cells collection/culturing bag supplemented with an effective amount of a retinoic acid receptor antagonist, a retinoid X receptor antagonist and/or a Vitamin D receptor antagonist, which substantially inhibits cell differentiation, or with an effective amount of nicotinamide, a nicotinamide analog, a nicotinamide or a nicotinamide analog derivative and a nicotinamide or a nicotinamide analog metabolite, which substantially inhibits cell differentiation as well; and a cells separation and/or washing buffer supplemented with an effective amount of a retinoic acid receptor antagonist, a retinoid X receptor antagonist and/or a Vitamin D receptor antagonist, which substantially inhibits cell differentiation, or with an effective amount of nicotinamide, a nicotinamide analog, a nicotinamide or a nicotinamide analog derivative and a nicotinamide or a nicotinamide analog metabolite, which substantially inhibits cell differentiation as well.

According to another aspect of the present invention there is provided a method of hematopoietic cells transplantation or implantation.

In one embodiment, the method comprises (a) obtaining hematopoietic stem cells to be transplanted from a donor; (b) providing the stem cells with ex-vivo culture conditions for cell proliferation and, at the same time, for reducing an expression and/or activity of CD38, thereby expanding the population of the stem cells, while at the same time, substantially inhibiting differentiation of the stem cells ex-vivo; and (c) transplanting or implanting the stem cells to a recipient.

In another embodiment, the method comprises (a) obtaining hematopoietic stem cells to be transplanted from a donor; (b) providing the stem cells with ex-vivo culture conditions for cell proliferation and, at the same time, for reducing a capacity of the stem cells in responding to retinoic acid, retinoids and/or Vitamin D, thereby expanding the population of the stem cells, while at the same time, substantially inhibiting differentiation of the stem cells ex-vivo; and (c) transplanting or implanting the stem cells to a recipient.

In still another embodiment the method comprises (a) obtaining hematopoietic stem cells to be transplanted from a donor; (b) providing the stem cells with ex-vivo culture conditions for cell proliferation and, at the same time, for reducing a capacity of the stem cells in responding to signaling pathways involving the retinoic acid receptor, the retinoid X receptor and/or the Vitamin D receptor, thereby expanding the population of the stem cells, while at the same time, substantially inhibiting differentiation of the stem cells ex-vivo; and (c) transplanting or implanting the stem cells to a recipient.

In yet another embodiment the method comprises (a) obtaining hematopoietic stem cells to be transplanted from a donor; (b) providing the stem cells with ex-vivo culture conditions for cell proliferation and with nicotinamide, a nicotinamide analog, a nicotinamide or a nicotinamide analog derivative or a nicotinamide or a nicotinamide analog metabolite, thereby expanding the population of the stem cells, while at the same time, substantially inhibiting differentiation of the stem cells ex-vivo; and (c) transplanting or implanting the stem cells to a recipient.

The donor and the recipient can be a single individual or different individuals, for example, allogeneic individuals.

According to yet another aspect of the present invention there is provided a method of adoptive immunotherapy.

In one embodiment the method comprises (a) obtaining hematopoietic stem cells from a recipient; (b) providing the stem cells with ex-vivo culture conditions for cell proliferation and, at the same time, for reducing an expression and/or activity of CD38, thereby expanding a population of the stem cells, while at the same time, substantially inhibiting differentiation of the stem cells; and (c) transplanting the stem cells to the recipient.

In another embodiment the method comprises (a) obtaining hematopoietic stem cells from a recipient; (b) providing the stem cells with ex-vivo culture conditions for cell proliferation and, at the same time, for reducing a capacity of the stem cells in responding to retinoic acid, retinoids and/or Vitamin D, thereby expanding a population of the stem cells, while at the same time, substantially inhibiting differentiation of the stem cells; and (c) transplanting the stem cells to the recipient.

In still another embodiment the method comprises (a) obtaining hematopoietic stem cells from a recipient; (b) providing the stem cells with ex-vivo culture conditions for cell proliferation and, at the same time, for reducing a capacity of the stem cells in responding to signaling pathways involving the retinoic acid receptor and/or the retinoid X receptor and/or the Vitamin D receptor, thereby expanding a population of the stem cells, while at the same time, substantially inhibiting differentiation of the stem cells; and (c) transplanting the stem cells to the recipient.

In yet another embodiment the method comprises (a) obtaining hematopoietic stem cells from a recipient; (b) providing the stem cells with ex-vivo culture conditions for cell proliferation and with nicotinamide, a nicotinamide analog, a nicotinamide or a nicotinamide analog derivative or a nicotinamide or a nicotinamide analog metabolite, thereby expanding a population of the stem cells, while at the same time, substantially inhibiting differentiation of the stem cells; and (c) transplanting the stem cells to the recipient.

According to yet another aspect of the present invention there is provided a method of mobilization of bone marrow stem cells into the peripheral blood of a donor for harvesting the cells.

In one embodiment the method comprises (a) administering an effective amount of an agent to the donor for reducing an expression and/or activity of CD38, thereby expanding a population of the stem cells, while at the same time, substantially inhibiting differentiation of the stem cells; and (b) harvesting the cells by leukophoresis.

In another embodiment the method comprises (a) administering an effective amount of an agent to the donor for reducing a capacity of the stem cells in responding to retinoic acid, retinoids and/or Vitamin D, thereby expanding a population of the stem cells, while at the same time, substantially inhibiting differentiation of the stem cells; and (b) harvesting the cells by leukophoresis.

In still another embodiment the method comprises (a) administering an effective amount of an agent to the donor for reducing a capacity of the stem cells in responding to signaling pathways involving the retinoic acid receptor and/or the retinoid X receptor and/or the Vitamin D receptor, thereby expanding a population of the stem cells, while at the same time, substantially inhibiting differentiation of the stem cells; and (b) harvesting the cells by leukophoresis.

In yet another embodiment the method comprises (a) administering to the donor an effective amount of an selected from the group consisting of nicotinamide, a nicotinamide analog, a nicotinamide or a nicotinamide analog derivative and a nicotinamide or a nicotinamide analog metabolite, thereby expanding a population of the stem cells, while at the same time, substantially inhibiting differentiation of the stem cells; and (b) harvesting the cells by leukophoresis.

Preferably, the methods of mobilization of stem cells further comprising administering to the donor at least one cytokine, preferably at least one early cytokine.

According to further features in preferred embodiments of the invention described below, reducing the expression and/or activity of CD38 is effected by an agent that downregulates CD38 expression.

According to still further features in the described preferred embodiments the agent that downregulates CD38 expression is selected from the group consisting of a retinoic acid receptor antagonist, a retinoid X receptor antagonist and a Vitamin D receptor antagonist. Alternatively, this agent is an antagonist for reducing a capacity of the stem cells in responding to retinoic acid, retinoid and/or Vitamin D.

According to still further features in the described preferred embodiments the agent that downregulates CD38 expression is a polynucleotide.

According to still further features in the described preferred embodiments the agent that downregulates CD38 expression the polynucleotide encodes an anti CD38, an anti retinoic acid receptor, an anti retinoid X receptor or an anti Vitamin D receptor antibody or intracellular antibody.

According to still further features in the described preferred embodiments the agent that downregulates CD38 expression the polynucleotide is a small interfering polynucleotide molecule directed to cause intracellular CD38, retinoic acid receptor, retinoid X receptor or Vitamin D receptor mRNA degradation.

According to still further features in the described preferred embodiments the agent that downregulates CD38 expression the small interfering polynucleotide molecule is selected from the group consisting of an RNAi molecule, an anti-sense molecule, a rybozyme molecule and a DNAzyme molecule.

According to further features in preferred embodiments of the invention described below, reducing the expression and/or activity of CD38 is effected by an agent that inhibits CD38 activity. The agent can be, for example, nicotinamide, a nicotinamide analog, a nicotinamide or a nicotinamide analog derivative or a nicotinamide or a nicotinamide analog metabolite.

The nicotinamide analog is preferably selected from the group consisting of benzamide, nicotinethioamide, nicotinic acid and α-amino-3-indolepropionic acid.

According to further features in preferred embodiments of the invention described below, providing the stem cells with the conditions for ex-vivo cell proliferation comprises providing the cells with nutrients and with cytokines.

According to still further features in the described preferred embodiments the cytokines are early acting cytokines.

According to still further features in the described preferred embodiments the early acting cytokines are selected from the group comprising stem cell factor, FLT3 ligand, interleukin-1, interleukin-2, interleukin-3, interleukin-6, interleukin-10, interleukin-12, tumor necrosis factor-α and thrombopoietin.

According to still further features in the described preferred embodiments the cytokines are late acting cytokines.

According to still further features in the described preferred embodiments the late acting cytokines are selected from the group comprising granulocyte colony stimulating factor, granulocyte/macrophage colony stimulating factor, erythropoietin, FGF, EGF, NGF, VEGF, LIF, Hepatocyte growth factor and macrophage colony stimulating factor.

According to still further features in the described preferred embodiments the stem cells are selected from the group consisting of embryonic stem cells and adult stem cells.

According to still further features in the described preferred embodiments the stem cells are hematopoietic stem cells.

According to still further features in the described preferred embodiments the stem cells are derived from a source selected from the group consisting of bone marrow, peripheral blood and neonatal umbilical cord blood.

According to still further features in the described preferred embodiments the stem cells that undergo expansion are mixed (e.g., not separated from, not enriched) with committed cells.

According to still further features in the described preferred embodiments the stem cells are enriched for hematopoietic CD34$^+$ cells.

According to still further features in the described preferred embodiments the hematopoietic cells are characterized by an absence, or significantly diminished expression of cell surface antigens CD38, CD3, CD61, CD19, CD33, CD14, CD15 or CD4.

According to still further features in the described preferred embodiments reducing the capacity of the stem cells in responding to signaling pathways is reversible, e.g., inherently reversible.

According to still further features in the described preferred embodiments reducing the capacity of the stem cells in responding to the above antagonists and/or signaling pathways of the above receptors is by ex-vivo culturing the stem cells in a presence of an effective amount of at least one retinoic acid receptor antagonist, at least one retinoid X receptor antagonist and/or at least one Vitamin D receptor antagonist, preferably, for a time period of 0.1-50%, preferably, 0.1-25%, more preferably, 0.1-15%, of an entire ex-vivo culturing period of the stem cells.

According to still further features in the described preferred embodiments, the retinoic acid receptor antagonist is selected from the group consisting of:
AGN 194310; AGN 193109; 3-(4-Methoxy-phenylsulfanyl)-3-methyl-butyric acid; 6-Methoxy-2,2-dimethvl-thiochroman-4-one,2,2-Dimethyl-4-oxo -thiochroman-6-yltrifluoromethane-sulfonate; Ethyl 4-((2,2 dimethyl-4-oxo-thiochroman-6-yl)ethynyl)-benzoate; Ethyl 4-((2,2-dimethy 14-triflouromethanensulfonyloxy-(2H)-thiochromen-6-yl) ethynyl)-benzoate(41); Thiochromen-6-yl]-ethynyl]-benzoate(yl); (p-[(E)-2-[3'4'-Dihydro -4,4'-dimethyl-7'-(heptyloxy)-2'H-benzothiopyran-6'yl]propenyl]benzoic acid 1'1'-dioxide; 2E,4E,6E-[7-(3,5-Di-t-butyl-4-n-butoxyphenyl)-3-methyl]-octa-2,4,6-trienoic acid; 2E,4E,6E-[7-(3,5-Di-t-butyl-4-n-propoxyphenyl)-3-methyl]-octa-2,4,6-trienoic acid; 2E,4E,6E-[7-(3,5-Di-t-butyl-4-n-pentoxyphenyl)-3-methyl]-octa-2,4,6-trienoic acid; 2E,4E,6E-[7-(3,5-Di-t -butyl-4-n-hexoxyphenyl)-3-methyl]-octa-2,4,6-trienoic acid; 2E,4E,6E-[7-(3,5-Di-t-butyl-4-n-heptoxyphenyl)-3-methyl]-octa-2,4,6-trienoic acid; 2E,4E,6E-[7-(3,5-Di-t-butyl-4-n-octoxyphenyl)-3-methyl]-octa-2,4,6-trienoic acid; (2E, 4E,6E)-7-[3-t-butyl-5-(1-phenyl-vinyl)-phenyl]-3-methyl-octa-2,4,6-trienoic acid; 2E,4E,6E-[7-(3,5-Di-t-butyl-4-{[4, 5-.sup.3H.sub.2]-n-pentoxy}phenyl)-3-methyl]-octa-2,4,6-trienoic acid; (2E,4E)-(1RS,2RS)-5-[2-(3,5-di-tert.butyl-2-ethoxy-phenyl)-cyclopropyl]-3-methyl-penta-2,4-dienoic acid ethyl ester; (2E,4E)-(1 RS,2RS)-5-[2-(3,5-di-tert.butyl-2-ethoxy-phenyl)-cyclopropyl]-3-methyl-penta-2,4-dienoic acid; (2E,4E)-(1RS,2RS)-5-[2-(3,5-di -tert.butyl-2-butoxyphenyl)-cyclopropyl]-3-methyl-penta-2,4-dienoic acid; (2E, 4E,6Z)-7-[3,5-di-tert.butyl-2-ethoxyphenyl]3-methyl-2,4,6-octatrienoic acid; (2E,4E,6Z)-7-[3,5-di-tert.butyl-2-butyloxyphenyl]-3-methyl-2,4,6-octatrienoic acid; 4-(5,6,7, 8-tetrahydro-5,5,8,8-tetramethyl-2-naphthalene-carboxamido) benzoic acid; (2E,4E)-3-methyl-5-[(1S,2S)-2-(5,5,8,8-tetramethyl-5,6,7,8-tetrahydro-naphthalen-2-yl)-cyclopropyl]-penta-2,4-dienoic acid; p-[(E)-2-[3',4'-Dihydro-4',4'-dimethyl-7'-(heptyloxy)-2'H-1-benzothiopyran-6'-yl]propenyl]benzoic acid; 1',1'-dioxide, 4-(7,7,10,10-Tetramethyl-1-pyridin-3-ylmethyl-4,5,7,8,9, 10-hexahydro-1H-naphto[2,3-g]indol-3-yl)-benzoic acid; (2E,4E,6Z)-7-[3,5-di-tert.butyl-2-methoxyphenyl]-3-methyl-2,4,6-octatrienoic acid; (2E,4E,6Z)-7-[3,5-di-tert.butyl-2-ethoxyphenyl]-3-methyl-2,4,6-octatrienoic acid; (2E,4E, 6Z)-7-[3,5-di-tert.butyl-2-hexyloxyphenyl]-3-methyl-2,4,6-octatrienoic acid; (2E,4E,6Z)-7-[3,5-di-tert.butyl-2-octyloxyphenyl]-3-methyl-2,4,6-octatrienoic acid; and (2E, 4E)-(1RS,2RS)-5-[2-(3,5-di-tert-butyl-2-butoxy-phenyl)-cyclopropyl]-3-methyl-penta-2,4-dienoic acid (2E,4E,6Z)-7-(3-n-propoxy-5,6,7,8-tetrahydro-5,5,8,8-tetramethylnaphthalene-2-yl)-3-methylocta-2,4,6-trienoic acid, 4-(5H-2,3(2,5 dimethyl-2,5-hexano)-5-n-propyldibenzo[b,e][1,4]diazepin-11-yl)benzoic acid, 4-(5H-2,3-(2,5-dimethyl-2,5-hexano)-5methyl-8-nitrodibenzo[b,e][1, 4]diazepin-11-yl)benzoic acid, 4-{[4-(4-Ethylphenyl)2,2-dimethyl-(2H)-thiochromen-6-yl]ethynyl}benzoic acid, 4-[4-2methyl-1,2-dicarba-closo-dodecaboran-1-yl-phenyl-carbamoyl]benzoic acid, 4-[4,5,7,8,9,10-hexahydro-7,7,10, 10-tetramethyl-1-(3-pyridylmethyl)-anthra[1,2-b]pyrrol-3-yl]benzoic acid, (3-pyridylmethyl)-]5-thiaanthra[2,1-b] pyrrol-3-yl)benzoic acid, and (3-pyridylmethyl)-anthra[2 ml-d]pyrazol-3-yl]benzoic acid.

According to still further features in the described preferred embodiments, the retinoid X receptor antagonist is selected from the group consisting of:
LGN100572, LGN100574, 1-(3-hydroxy-5,6,7,8-tetrahydro-5,5,8,8-tetramethylnaphthalene-2-yl)ethanone, 1-(3-propoxy-5,6,7,8-tetrahydro-5,5,8,8-tetramethylnaphthalene-2-yl)ethanone, 3-(3-propoxy-5,6,7,8-tetrahydro-5,5,8,8-tetramethylnaphthalene-2-yl)but-2-enenitrile, 3-(3-propoxy-5,6,7,8-tetrahydro-5,5,8,8-tetramethylnaphthalene-2-yl)but-2-enal, (2E,4E,6E)-7-3[-propoxy-5,6,7,8-tetrahydro 5,5,8,8-tetramethyl-2-naphthalene-2-yl]-3-methylocta-2,4,6-trienoic acid, 4-[3,5,5,8,8-pentamethyl-5,6,7,8-tetrahydro-2-naphthyl)carbonyl]benzoic acid, 4-[1-(3,5,5,8,8-pentamethyl-5,6,7,8-tetrahydro-2-naphthyl)ethenyl]benzoic acid, 4-[1(3,5,5,8,8-pentamethyl-5,6,7,8-tetrahydro-2-naphthyl)cyclopropyl]benzoic acid, 4-[1-(3,5,5,8,8-pentamethyl-5,6,7,8-tetrahydro-2-naphthyl)ethenyl]benzenete trazole, 2-[1-(5,5,8,8-tetramethyl-5,6,7,8-tetrahydro-2-naphthyl) ethenyl]pyridine-5-carboxylic acid, 2-[1-(3,5,5,8,8-pentamethyl-5,6,7,8-tetrahydro-2-naphthyl)ethyl]pyridine-5-carboxylic acid, ethyl-2-[1-(3,5,5,8,8-pentamethyl-5,6,7,8-tetrahydro -2-naphthyl)ethenyl]pyridine-5-carboxylate, 5-[1-3,5,5,8,8-pentamethyl -5,6,7,8-tetrahydro-2-naphthyl) ethenyl]pyridine-2-carboxylic acid, 2-[1-(3,5,5,8,8-pentamethyl-5,6,7,8-tetrahydro-2-naphthyl)cyclopropyl]pyridine-5-carboxylic acid, methyl 2-[1-(3,5,5,8,8-pentamethyl-5,6,7, 8-tetrahydro-2-naphthyl)cyclopropyl]pyridine-5-carboxylate, 4-[1-(3,5,5,8,8-pentamethyl-5,6,7,8- tetrahydro-2-naphthyl)ethenyl]-N-(4-hydroxyphenyl)
benzamide, 2-[1(3,5,5,8,8-Pentamethyl-5,6,7,8-tetrahydro-2-naphthyl)ethenyl]pyridine-5-carboxylic acid, 2-[1-(3,5,5,8,8-Pentamethyl-5,6,7,8-tetrahydro-2-naphthyl)cyclopropyl]pyridine-5-carboxylic acid, 4-[(3,5,5,8,8-pentamethyl-5,6,7,8-tetrahydro-2-naphthyl)carbonyl]benzoic acid butyloxime, 4-[(3,5,5,8,8-pentamethyl-5,6,7,8-tetrahydro-2-naphthyl)carbonyl]benzoic acid propyloxime, 4-[(3,5,5,8,8-pentamethyl-5,6,7,8-terrahydro-2-naphthyl)carbonyl]benzoic acid cyanoimine, 4-[(3,5,5,8,8-pentamethyl-5,6,7,8-tetrahydro-2-naphthyl)carbonyl]benzoic acid allyloxime, 4-[(3,5,5,8,8-pentamethyl-5,6,7,8-tetrahydro-2-naphthyl)carbonyl]benzoic acid 4-(3-methylbut-2-enoic acid)oxime, and 4-[(3,5,5,8,8-pentamethyl-5,6,7,8-tetrahydro-2-naphthyl)carbonyl]benzoic acid 1-aminoethyloxime (2E,4E,6Z)-7-(3-n-propoxy-5,6,7,8-tetrahydro-5,5,8,8-tetramethylnaphthalene-2-yl)-3-methylocta-2,4,6-trienoic acid, and 4-(5H-2,3(2,5 dimethyl-2,5-hexano)-5-n-propyldibenzo[b,e] [1,4]diazepin-11-yl)benzoic acid, and 4-(5H-2,3-(2,5-dimethyl-2,5-hexano)-5methyl-8-nitrodibenzo[b,e][1,4]diazepin-11-yl)benzoic acid.

According to still further features in the described preferred embodiments, the Vitamin D receptor antagonist is selected from the group consisting of: 1 alpha, 25-(OH)-D3-26,23 lactone; 1 alpha, 25-dihydroxyvitamin D (3); the 25-carboxylic ester ZK159222; (23S)-25-dehydro-1 alpha-OH-D (3); (23R)-25-dehydro-1 alpha-OH-D (3); 1 beta, 25 (OH)$_2$ D$_3$; 1 beta, 25(OH)$_2$-3-epi-D$_3$; (23S) 25-dehydro-1 alpha(OH) D3-26,23-lactone; (23R) 25-dehydro-1 alpha (OH)D3-26,23-lactone and Butyl-(5Z,7E,22E-(1S,7E,22E-(1S,3R,24R)-1,3,24-trihydroxy-26,27-cyclo-9,10-secocholesta-5,7,10(19),22-tetraene-25-carboxylate).

The present invention successfully addresses the shortcomings of the presently known configurations by providing a method of propagating cells, yet delaying their differentiation by interference with CD38 expression and/or activity, or with retinoic acid, retinoid X and/or Vitamin D receptor signaling.

The present invention further successfully addresses the shortcomings of the presently known configurations by enabling, for the first time, expansion of renewable stem cells in the presence of committed cells, so as to obtain an expanded population of renewable stem cells, albeit their origin from a mixed population of cells, in which they constitute a fraction of a percent.

Additional features and advantages of the methods cell preparations and articles of manufacture according to the present invention will become apparent to the skilled artisan by reading the following descriptions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1B is a FACS analysis plot showing RAR antagonist ($10^{-5}$ M) treated culture cell surface marker expression with a similar level of expression of the CD34 antigen, but an almost complete abrogation of the CD38 and lineage-related antigen expression, as compared to controls.

FIG. 5A is a FACS analysis plot of the negative control showing no background staining.

FIG. 5B is a FACS analysis plot of the positive control of reselected cell cultures showing ample CD34$^+$ cell surface staining.

FIG. 5C is a FACS analysis plot of the RAR antagonist treated cultures 2 weeks post reselection showing a marked leftward shift in profile, consistent with a less differentiated state.

FIG. 5D is a FACS analysis plot of the RAR antagonist treated cultures ($10^{-7}$) 11 weeks post reselection showing ample CD34+ cell surface staining, and a profile consistent with a more differentiated state.

FIG. 5E is a FACS analysis plot of the RAR antagonist treated cultures ($10^{-5}$) 11 weeks post reselection showing a marked leftward shift in profile, consistent with a less differentiated state.

FIG. 8A is a photomicrograph of three weeks old primary hepatocyte cultures isolated from mice. Hepatocytes were probed for expression of α-fetoprotein (AFP) and counterstained with hematoxylin. Moderate AFP staining is evident (red-brown precipitate).

FIG. 8B is a photomicrograph of three week old primary hepatocyte cultures isolated from mice. Hepatocytes were incubated in the presence of $10^{-5}$ M retinoic acid receptor antagonist (AGN 194310) and were similarly probed for AFP expression and counterstained with hematoxylin. AGN 194310-treated hepatocytes revealed a marked increase in AFP expression, as compared to controls.

FIG. 9A is a photomicrograph of giemsa stained, three week old, primary murine hepatocyte cultures revealing cell morphology. Few oval cells were noted in this sample (thick arrow), in contrast to numerous hepatocytes with typical morphology (narrow arrow)

FIG. 9B is a photomicrograph of giemsa stained, primary hepatocyte cultures incubated in the presence of $10^{-5}$ M retinoic acid receptor antagonist (AGN 194310). Antagonist treated cells showed a marked increase in oval cell population (arrow).

FIG. 9C is a photomicrograph of giemsa stained, primary hepatocyte cultures incubated in the presence of $10^{-5}$ M retinoic acid receptor antagonist (AGN 194310) followed by trypsinization and replating, at a ratio of 1:2, in a culture medium devoid of cytokines. These cultures similarly revealed characteristic hepatocyte morphology FIG. 10A is a photomicrograph of three weeks old primary hepatocyte cultures isolated from mice, and supplemented with EGF (20 ng/ml) and HGF (20 ng/ml). Hepatocytes were treated with RAR antagonist AGN 194310 at $10^-$ M to $10^{-7}$ M, probed for expression of albumin and counterstained with hematoxylin. There is no appreciable background staining. Indicated that the cells expanded in cultures supplemented with the antagonist are hepatocytes by nature.

FIG. 10B is a photomicrograph of three weeks old primary hepatocyte control cultures isolated from mice, similarly supplemented with EGF and HGF and probed for albumin expression. Negligible background staining is evident here as well.

FIG. 10C is a photomicrograph of three weeks old primary hepatocyte RAR antagonist treated cultures isolated from mice, similarly supplemented with EGF and HGF and probed for α-fetoprotein expression. Significant strong AFP staining is evident (red-brown precipitate), indicating expansion of progenitor cells.

FIG. 10D is a photomicrograph of three weeks old primary hepatocyte control cultures isolated from mice, similarly supplemented with EGF and HGF and probed for α-fetoprotein expression. Negligible staining is evident indicating a more differentiated cellular phenotype. All figures were photographed at 10×/0.3 magnification.

FIG. 11A is a photomicrograph of first passage heaptocyte control cultures isolated from mice and supplemented with EGF and HGF, split 1:2 following 2 weeks in culture and cultured for an additional week prior to probing for albumin expression, as above. Numerous typical hepatocytes (small arrow) are evident.

FIG. 11B is a photomicrograph of first passage RAR antagonist AGN 194310 ($10^{-5}$-$10^{-7}$ M) treated heaptocyte cultures isolated from mice cultured as in A and probed for albumin expression. Typical hepatocyte morphology (small arrow) is evident in this frame as well.

FIG. 11C is a photomicrograph of first passage RAR antagonist treated hepatocyte cultures, cultured and probed as in B. Numerous characteristic oval cells are evident (large arrow) in the field. Magnification—20×/0.5.

FIG. 11D is a photomicrograph is a lower magnification of FIG. 11C, revealing numerous islets of oval cells in the RAR antagonist treated cultures, consistent with a less-differentiated phenotype.

FIG. 11E is a photomicrograph of second passage heaptocyte control cultures isolated from mice and supplemented with EGF and HGF, split 1:2 following 2 weeks in culture, cultured for an additional week prior to 1:4 split, and following a final additional 4 day culture, probing for albumin expression, as above. Few hepatocytes are evident.

FIG. 11F is a photomicrograph of similarly isolated and cultured second passage heaptocyte cultures treated with RAR antagonist AGN 194310 ($10^{-5}$ M to $10^{-7}$ M). Significantly greater numbers of hepatocytes are evident in the cultures as compared to controls. Magnification—20×/0.5.

FIG. 12A is a plot presenting the FACS analysis of cultures treated with cytokines only (control), RAR antagonist AGN 194310 ($10^{-7}$ M) and a combination of RAR antagonist ($10^{-7}$ M) and RXR antagonist, 3 weeks post reselection. A marked leftward shift in profile of the combined, RAR and RXR antagonists, treatment, consistent with a less differentiated state, as compared with the untreated control and the RAR antagonist treatment is demonstrated.

FIG. 12B is a plot presenting a FACS analysis of cultures treated with cytokines only (control), RAR antagonist AGN 194310 ($10^{-7}$ M), RXR antagonist LGN 100754 ($10^{-7}$ M) and a combination of RAR and RXR antagonists ($10^{-7}$ M), 5 weeks post reselection. A marked leftward shift in profile of the combined, RAR and RXR antagonists, treatment, consistent with a less differentiated state, as compared with the RAR antagonist treatment is demonstrated.

FIG. 18a is a dot plot presenting a FACS analysis of re-selected CD34+ cells from a 3 weeks culture treated with cytokines, with or without 5 mM nicotinamide. The CD34+/CD38− cells are shown in the upper left part of the plot, demonstrating a marked increase of CD34+/CD38− cells in the nicotinamide treated culture.

FIG. 18b is a dot plot presenting a FACS analysis of re-selected CD34+ cells from a 3 weeks culture treated with cytokines, with or without 5 mM nicotinamide, 3 weeks post reselection. The CD34+/Lin− cells are shown in the upper left part of the plot, demonstrating a marked increase of CD34+/Lin− cells in the nicotinamide treated culture.

FIG. 18c is a dot plot presenting a FACS analysis of re-selected CD34+ cells from a 3 weeks culture treated with cytokines, with or without 5 mM nicotinamide, 3 weeks post reselection. The CD34+/(HLA-DR38)− cells are shown in the upper left part of the plot, demonstrating a marked increase of CD34+/+/(HLA-DR38)− cells in the nicotinamide treated culture.

DESCRIPTION OF THE PREFERRED EMBODIMENTS

Figure 1A:
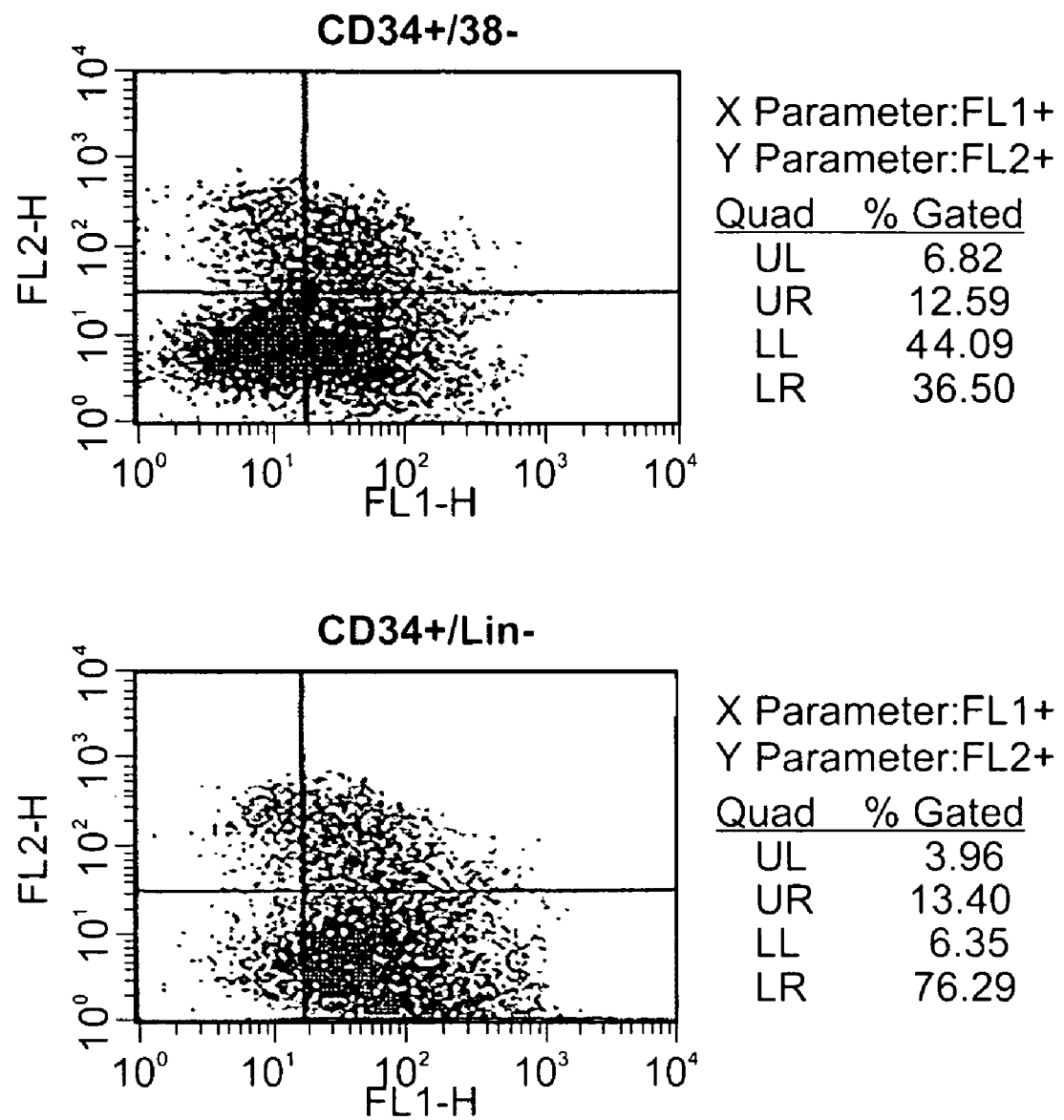
FIG. 1A is a FACS analysis plot showing control cell surface marker expression with liberal expression of CD34, CD38 and lineage-related antigens.

The present invention is of methods of expanding a population of stem cells, while at the same time, substantially inhibiting differentiation of the cells ex-vivo and/or in-vivo. In one embodiment, the invention facilitates the efficient use as a therapeutic ex-vivo cultured cell preparation, which includes an expanded, large population of renewable stem cells, in which differentiation was inhibited while cell expansion was propagated. Specifically in this respect, the present invention can be used to provide ex-vivo expanded populations of stem cells, which can be used for applications in hematopoietic cell transplantations, and in generation of stem cells suitable for genetic manipulations, which may be used for cellular gene therapy. Additional applications may include, but are not limited to, adoptive immunotherapy, treatments for multiple diseases, such as, for example, β-hemoglobinopathia, implantation of stem cells in an in vivo cis-differentiation and trans-differentiation settings, and ex vivo tissue engineering in cis-differentiation and trans-differentiation settings. The present invention further relates to expanded stem cell preparations and to articles-of-manufacture for preparing same.

The present invention discloses the use of various molecules (also referred to herein as agents), for interfering with CD38 expression and/or activity, thereby inducing ex-vivo expansion of stem cell populations, resulting, when applied, for example, to hematopoietic stem cells, in large numbers of undifferentiated CD34+/Lin− (CD33, CD14, CD15, CD4, etc.), as well as CD34+/CD38− cells, especially CD34+$_{dim}$/Lin− cells. This novel and versatile technology may be used for ex-vivo and/or in-vivo expansion of stem cells, of hematopoietic and other origins, maintaining their self-renewal potential for any in-vivo or ex-vivo application which requires a large population of stem cells.

While reducing the present invention to practice, it was unexpectedly found that a series of molecules that are capable of interfering with CD38 expression and/or activity, repress the process of differentiation of stem cells and stimulates and prolongs, for up to 16-18 weeks, the phase of active cell proliferation and expansion ex-vivo. Following about 16-18 weeks of expansion, the cells begin to differentiate; hence, the effect of these molecules is reversible. In other words, treating the cells ex-vivo as herein described does not result in the cells transforming into a cell line.

This unexpected effect was surprisingly obtained when the source of cells was CD34+ enriched hematopoietic cells (stem and early progenitor cells) and, most surprisingly, also when the source of cells included the entire fraction of mononuclear blood cells (whole fraction of white blood cells, which includes stem, progenitor and committed cells) were used. As is described in the Background section, presently there is no disclosed technology by which to expand non-enriched stem cells.

Furthermore primary hepatocyte cultures incubated with agents such as retinoic acid receptor antagonists of the RAR and RXR super families, revealed an increase in the proportion of cells producing α-fetoprotein, hence inducing the proliferation of early hepatocyte populations. Antagonist-treated hepatocyte cultures grown without cytokines persisted for at least 3 weeks in culture, a finding in stark contrast to previous data indicating an almost impossibility in growing primary hepatocytes for extended periods of time in culture, especially in the absence of cytokines (Wick M, et al. ALTEX. 1997; 14(2): 51-56; Hino H, et al. Biochem Biophys Res Commun. 1999 Mar. 5;256(1): 184-91; and Tateno C, and Yoshizato K. Am J Pathol. 1996; 148(2): 383-92). Supplementation with growth factors alone was insufficient to stimulate hepatocyte proliferation, only RAR antagonist treatment of hepatocyte cultures resulted in the proliferation of early hepatocyte populations and in their persistence in culture, evident even following first and second passages.

This newly discovered effect of the molecules useable in context of the present invention was used for maximizing the ex-vivo expansion of various types of cells as is further detailed hereinunder and exemplified in the Examples section that follows.

The principles and operation of the present invention may be better understood with reference to the drawings and accompanying descriptions and examples.

Before explaining at least one embodiment of the invention in detail, it is to be understood that the invention is not limited in its application to the details of construction and the arrangement of the components set forth in the following description or illustrated in the Examples section. The invention is capable of other embodiments or of being practiced or carried out in various ways. Also, it is to be understood that the phraseology and terminology employed herein is for the purpose of description and should not be regarded as limiting.

CD38 is a member of an emerging family of cytosolic and membrane-bound enzymes whose substrate is nicotinamide adenine dinucleotide (NAD). Two of the metabolites produced by CD38, cADPR and NAADP, have been shown to induce the release of intracellular calcium in cells isolated from tissues of plants, invertebrates and mammals, suggesting that these metabolites may be global regulators of calcium responses (Lee et al., 1999 Biol. Chem. 380;785-793).

Recently, it has been reported that granulocytic differentiation of the human committed cell line HL-60 cells can be induced by retinoic acid and is accompanied by a massive expression of CD38. Concomitant with CD38 expression was the accumulation of cADPR, and both time courses preceded the onset of differentiation, suggesting a causal role for CD38. Consistently, treatment of HL-60 cells with a permeant inhibitor of CD38, nicotinamide, inhibited both the CD38 activity and differentiation. More specific blockage of CD38 expression was achieved by using morpholino antisense oligonucleotides targeting its mRNA, which produced a corresponding inhibition of differentiation as well (Munshi C B, Graeff R, Lee H C, *J Biol Chem* 2002 Dec. 20;277(51): 49453-8).

Other studies have shown an opposite effect of CD38 signaling on progenitor cell differentiation. Short term treatment of human progenitor cells with cADPR mediated a significant increase in colony size and colony output, implying a direct correlation between CD38 signaling and ex-vivo stem cell expansion (Podesta (2000) FASEB J. 14:680-690). In a more recent study reported by the same group, the effects of cADPR on engraftment of hemopoietic stem cells into irradiated NOD/SCID mice were addressed (Podesta (2002) FASEB J. December 3 epub ahead of print). In this study a dual effect of cADPR on human hemopoietic progenitors was demonstrated in vivo, essentially, enhanced proliferation of committed progenitors responsible for improvement of short-term engraftment; and expansion of human stem cells with increased long-term human engraftment into secondary recipients. Hence, these results suggest the use of cADPR to achieve long-term expansion of human stem cells.

Thus, the prior art studies conducted on human stem cells, thus far, teach the use of cADPR, a product resulting from CD38 catalysis, for ex-vivo or in-vivo expansion of human stem cells.

While reducing the present invention to practice, the present inventors have suprisingly uncovered that inhibition of CD38 activity or expression results in ex-vivo expansion of human stem cells and, at the same time, in limited differentiation of the cells.

Evidently, the prior art described above teaches away from the present invention.

Retinoid receptors such as RAR, RXR and VDR and their agonists, such as Vitamin A and it's active metabolites and Vitamin D and it's active metabolites are involved in the regulation of gene expression pathways associated with cell proliferation and differentiation.

Vitamin D, which was shown to be a differentiation inducer of myelomonocytic cells, transduces its signals via induction of hetrodimerization of the RXR-VDR retinoid receptors (28), whereas RAR-RXR or RXR-RXR hetrodimerization is essential for retinoids inducing granulocytic differentiation.

It was shown that the retinoids are essential for the maintenance of normal differentiation in many tissues. For example, in the epithelial system (29), retinoid-deficient tissues acquire a pre-malignant phenotype, which is characterized by enhanced mitotic activity and loss of differentiation (30). The RAR-β gene is expressed in normal epithelial tissue, where its expression is up-regulated by treatment with retinoic acid (31, 32). In many malignant cell lines derived from various carcinomas the level of RAR-β2 mRNA is decreased or undetectable (33-37), indicating that the specific loss of RAR-β2 mRNA expression may be an important event in tumorogenesis.

The disruption of retinoic acid receptor (RAR) activity characterizes the human acute promyelocytic leukemia (APL) and is associated with a block of granulocytic differentiation, indicating that RARs are critical regulators of normal myeloid differentiation. Moreover, knockout mice, deficient in retinoic acid receptors display an in vitro block to granulocyte differentiation (38, 39).

Although the above evidence clearly portrays an important role for RARs in regulating myelopoiesis, several critical questions remain unanswered. If RAR activity is ligand concentration-dependent, then what is the mechanism by which RAR activity regulates myeloid differentiation of cells that are exposed to the uniform "physiological" concentrations of retinoids that are presumably present in blood and bone marrow? Most importantly from a clinical standpoint, why do only the acute pro-myelocytic leukemic cells (APL) exhibit a dramatic response to retinoids while the other 90% of acute myelogenous leukemias do not, even though these other acute myelogenous leukemias express normal RARs (40)?

The biological effect of retinoids and retinoid receptors on normal, non-leukemic, hematopoietic stem cells was reported by Purton et al. (41).

Purton et al. (41) demonstrated that pharmacological levels (1 μmol) of all-trans-retinoic-acid (ATRA) enhanced the generation of colony-forming cell (CFC) and colony-forming unit-spleen (CFU-S) in liquid suspension cultures of Lin$^-$ c-kit$^+$ Sca-1$^+$ murine hematopoietic precursors. Purton et al.

(41) further investigated the effects of ATRA as well as an RAR antagonist, AGN 193109, on the generation of transplantable cells, including pre-CFU-S, short-term repopulating stem cells (STRCs), and long-term repopulating stem cells (LTRCs). Purton et al. (41) demonstrated that ATRA enhanced the ex-vivo maintenance and production of competitive repopulating STRCs and LTRCs from $Lin^-c-kit^+$ $Sca-1^+$ cells cultured in liquid suspension for 14 days. In addition, ATRA prevented the differentiation of these primitive stem cells into more mature pre-CFU-S during the 14 days of culture. In marked contrast, $Lin^-c-kit^+$ $Sca-1^+$ cells cultured with AGN 193109, an RAR antagonist, for 7 days had virtually no short- or long-term repopulating ability, but displayed an approximately 6-fold increase in the pre-CFU-S population. Purton et al. (41) conclusion from these studies was that the agonist to RAR, namely retinoic acid, enhances the maintenance and self-renewal of short- and long-term repopulating stem cells. In contrast, the RAR antagonist AGN 193109 abrogates reconstituting ability, most likely by promoting the differentiation of the primitive stem cells. Purton et al. (41) argue that these results imply an important and unexpected role of retinoids in regulating hematopoietic stem cell differentiation (41).

Whereas retinoids accelerates the growth and differentiation of granulocyte progenitors in cytokine-stimulated cultures of purified $CD34^+$ cells (42), at the stem cell level, the retinoids show an opposite effect.

Although in a non-hematopoietic tissue, but in accordance with Purton et al. (41), Kamei also demonstrated that retinoids, especially all-trans-retinoic-acid, inhibit the differentiation of pre-adipose cells (43).

Hence, in the hematopoietic system, nuclear retinoid receptors were strongly implicated in pathways controlling and promoting downstream differentiation of lineage-committed cells. As was shown in detail for several leukemia cell line models, such as HL-60, NH4, and 32D, which are lineage committed cells that are blocked at the myeloblast or promyelocytic stage of differentiation, inactivation of these receptors by specific antagonists, antisense or transduction with truncated receptors is associated with inhibition of induced granulocytic and monocytic differentiation.

In contrast to normal cells, in leukemia there is a disruption between regulatory pathways controlling cell proliferation and differentiation. These pathways are strictly coupled in normal cells. The only exception in which these two processes, proliferation and commitment to differentiation are not coupled, is the self-renewal proliferation pathway of the stem cells. Therefore, all the above studies do not teach the role of retinoid receptors at the stem cell level altogether (19, 22, 64).

While reducing the present invention to practice it was demonstrated that retinoic acid antagonists, when added to ex-vivo hematopoietic or hepatocyte cultures for only a limited, short-term period, enable extended long-term expansion of self-renewable stem cells.

The antagonists did not have any significant positive or negative effect on overall cell and $CD34^+$ cell expansion during the short-term cultures. In addition, $CD34^+$ antigen is expressed on committed as well as multi potent stem cells. Only a small fraction of the entire $CD34^+$ cell population, the $CD34^+/CD38^-$ and $CD34^+/Lin^-$ cells, belong to the stem and early progenitor cell compartment.

Analysis of the content of these two rare subpopulations in two weeks ex-vivo cultures revealed that cultures supplemented with a RAR antagonist contained higher percentages of $CD34^+/CD38^-$ cells and $CD34^+/Lin^-$ cells as compared to cultures treated only with the early acting cytokines Thrombopoietin (TPO), interleukin-6 (IL-6), an FLT-3 ligand and stem cell factor (SCF). The antagonist completely abolished the expression of the CD38 antigen. Also there was inhibition of a variety of other lineage-specific (Lin) antigens. The effect of the antagonist is specific and it is apparently targeted to key regulatory genes located at the checkpoint of self-renewal and commitment to differentiation decision. These conclusions are derived from the results described herein in the Examples section, showing that the RAR antagonist down regulates only the expression of differentiation associated antigens, but not of antigens associated with stem cell phenotype such as the CD34 antigen. The percentages and absolute numbers of $CD34^+$ cells were not affected by the antagonist during the short-term culture.

Further support for antagonist-specific effects on regulatory events of self-renewal and commitment to differentiation comes from experiments conducted herein with primary and passaged hepatocyte cultures. Primary cultures incubated with the antagonists revealed an increase in the proportion of cells producing α-fetoprotein, and in the number of histologically distinct oval cells, events associated with proliferation of early hepatocyte populations. These early hepatocyte populations persisted for at least 3 weeks in culture, even in the absence of supplemental cytokines, a most unprecedented finding. Furthermore, supplementation of the cultures with growth factors had no effect on the proliferation of early hepatocyte populations, however RAR antagonist treatment enabled expansion of this population even following first passage, and demonstrated significantly expanded hepatocyte populations following second passage, further indicating a role for antagonists in cellular self-renewal capability.

In addition to its effect on short-term cultures, while reducing the present invention to practice, it was demonstrated that short-term treatment with the antagonist molecule also enabled the long-term ex-vivo expansion and self-renewal of stem cells, e.g. $CD34^+/Lin^-$ and $CD34^+38^-$ cells. Interestingly, limited exposure to the antagonist was sufficient to produce a significant and impressive prolongation of the long and extended long-term cultures as demonstrated by FACS analysis of stem cells and the functional LTC-CFUc. During the long and extended long-term cultures, the content of CFUc and CFU-mix impressively increased as compared to the content of CFU in cultures treated only with the cytokines, which actually decreases during the long-term cultures. In fact, many of the control cultures were unable to maintain any CFU potential in the long and extended long-term culture. In contrast to cultures treated for 3 weeks with the antagonist, which showed a dramatic and continuous increase of CFU-mix during the extended long-term culture period, cytokine-only treated cultures did not enable the expansion or even the maintenance of mix-colonies during the entire culture period. Expansion of stem cells, as revealed from the phenotype characterization, is in complete agreement with the long-term self-renewal potential as measured by the functional LTC-CFUc assay. Both assays demonstrate superior and prolonged expansion of self-renewing stem cells in cultures pulsed with the antagonist molecule.

It has been shown that RAR antagonists inhibited RA induced granulocytic differentiation of committed, promyelocytic HL-60 cells (25). It was also shown, that gene transfection of a truncated RAR inhibited the response of mouse derived myeloid leukemic cell line, 32D, to G-CSF (22). These studies, however, were performed with leukemic, lineage committed cell lines and specifically show only inhibition of granulocytic differentiation induced by RA or G-CSF. Hence, no regulation at the stem cell level can be concluded from the above studies.

The study presented herein is the first to demonstrate that an RAR antagonist molecule can regulate ex-vivo differentiation processes of normal stem cells.

As opposed to Purton et al. (41), whose teachings are described above, it is demonstrated herein, using antagonist molecules to retinoid receptors and human stem cell cultures, that retinoid receptors are involved in the regulation of stem cell self-renewal. It is further demonstrated herein that the addition of these molecules for only a limited, short-term period to the ex-vivo cultures media enables the continuous proliferation of stem cells with no alteration of their phenotype for extended time periods. Furthermore, these effects of retinoic acid receptor antagonists did not involve any cell transformation and do not result in any cell line formation.

Opposite to cell lines occasionally obtained by transduction with a truncated, dominant negative RAR (22-23), it is shown herein that, whether the antagonist was supplemented for only the first two to three weeks or continuously for the entire culture period, all cultured cells underwent normal myeloid, erythroid and lymphoid differentiation and completely lost any cell proliferation ability 16-18 weeks after the initiation of the cultures.

As opposed to genetic modifications obtained by transduction procedures that induce infinitive alterations in gene expression and cell functions (unless the transduced gene is shut off), continuous treatment with the RAR antagonist did not result in infinitive expansion or maintenance of $CD34^+$/$Lin^-$ phenotype. Therefore, the mechanism of activity of a dominant negative receptor is very different than the mechanism of RAR antagonist molecules. Additional supportive data of a different mode of action comes from experiments demonstrating that cells transduced with a dominant negative RAR remain immature even in the presence of a differentiation-inducers (22), which definitely is not the case with normal, non leukemic cells treated with an RAR antagonist.

Starting with normal mouse derived bone marrow (BM) cells and following transduction with a truncated RAR receptor, Collins (23) occasionally obtained a mouse-stem cell line. However, using the same mouse-derived cells and an RAR antagonist, Purton et al. (41) demonstrated that an RAR antagonist accelerated stem cell differentiation, whereas retinoic acid supported ex-vivo expansion of stem cells (41). These data provided by Purton et al. (41) and Collins (23) favor the existence of two different, unrelated mechanisms as herein discussed.

In addition to the retinoid receptors effect on hematopoietic tissue, it was demonstrated that receptors belonging to the retinoid receptor family are involved in differentiation pathways controlling normal embryogenesis as well as adult tissues development.

Multiple fetal anomalies occur in vitamin A deficient animals as well as in retinoic acid receptor gene 'knockout' mice, indicating that retinoic acid (an active metabolite of vitamin A) performs some essential functions in normal development. Retinoids are also long known to influence skin morphology. When antagonists to RAR are given late in gestation, 14 days post conception (dpc), they delay differentiation and maturation of the fetal skin and hair follicles in mouse (65).

RXR-alpha ablation results in epidermal interfollicular hyperplasia with keratinocyte hyperproliferation and aberrant terminal differentiation, accompanied by an inflammatory reaction of the skin. It was further shown that RXR-alpha/VDR heterodimers play a major role in controlling hair cycling, and suggested that additional signaling pathways mediated by RXR-alpha heterodimerized with other nuclear receptors are involved in postnatal hair follicle growth (66).

Taking together the above data, it is concluded that at the stem cell level, positive and negative signals via receptors belonging to the retinoid receptor family, control the physiological balance between self-renewal and commitment to differentiation of normal hematopoietic and non-hematopoietic stem cells.

The novel method of ex-vivo down-regulation of cell differentiation, enabled large expansion of embryonic and adult, hematopoietic and non-hematopoietic stem cells and may be utilized for transplantation of hematopoietic cells, gene therapy, cell replacement therapy or any other application, which requires increasing numbers of stem cells.

The utilization of a small molecule for obtaining large stem cell expansion is a feasible, economical and safe method.

Hence, in the course of the present study it was found that a series of chemical agents that bind retinoic acid, retinoid X and/or Vitamin D receptors interfere with proper receptor signaling. This interference can reversibly inhibit (delay) the process of ex-vivo differentiation of stem cells, thereby stimulating and prolonging active ex-vivo stem cell expansion.

This newly discovered effect of receptor antagonist application is utilizable for maximizing the ex-vivo expansion of various types of cells including hematopoietic cells, hepatocytes and embryonic stem cells. Such ex-vivo expanded cells can be applied in several clinical situations. The following lists a few.

Hematopoietic cell transplantation: Transplantation of hematopoietic cells has become the treatment of choice for a variety of inherited or malignant diseases. While early transplantation procedures utilized the entire bone marrow (BM) population, recently, more defined populations, enriched for stem cells ($CD34^+$ cells) have been used (44). In addition to the marrow, such cells could be derived from other sources such as peripheral blood (PB) and neonatal umbilical cord blood (CB) (45). Compared to BM, transplantation with PB cells shortens the period of pancytopenia and reduces the risks of infection and bleeding (46-48).

An additional advantage of using PB for transplantation is its accessibility. The limiting factor for PB transplantation is the low number of circulating pluripotent stem/progenitor cells.

To obtain enough PB-derived stem cells for transplantation, these cells are "harvested" by repeated leukophoresis following their mobilization from the marrow into the circulation by treatment with chemotherapy and cytokines (46-47). Such treatment is obviously not suitable for normal donors.

The use of ex-vivo expanded stem cells for transplantation has the following advantages (49-50):

It reduces the volume of blood required for reconstitution of an adult hematopoietic system and may obviate the need for mobilization and leukophoresis (46).

It enables storage of small number of PB or CB stem cells for potential future use.

In the case of autologous transplantation of recipients with malignancies, contaminating tumor cells in autologous infusion often contribute to the recurrence of the disease (46). Selecting and expanding $CD34^+$ stem cells will reduce the load of tumor cells in the final transplant.

The cultures provide a significant depletion of T lymphocytes, which may be useful in the allogeneic transplant setting for reducing graft-versus-host disease.

Clinical studies indicate that transplantation of ex-vivo expanded cells derived from a small number of PB $CD34^+$ cells can restore hematopoiesis in recipients treated with high doses of chemotherapy, although the results do not yet allow firm conclusions about long term in-vivo hematopoietic capabilities of these cultured cells (46-47).

For successful transplantation, shortening of the duration of the cytopenic phase, as well as long-term engraftment, is crucial. Inclusion of intermediate and late progenitor cells in the transplant could accelerate the production of donor-derived mature cells thereby shortening the cytopenic phase. It is important, therefore, that ex-vivo expanded cells include, in addition to stem cells, more differentiated progenitor cells in order to optimize short-term recovery and long term restoration of hematopoiesis. Expansion of intermediate and late progenitor cells, especially those committed to the neutrophilic and megakaryocytic lineages, concomitant with expansion of stem cells, should serve this purpose (51).

Such cultures may be useful in restoring hematopoiesis in recipients with completely ablated bone marrow, as well as in providing a supportive measure for shortening recipient bone marrow recovery following conventional radio- or chemo-therapies.

Prenatal diagnosis of genetic defects in scarce cells: Prenatal diagnosis involves the collection of embryonic cells from a pregnant woman, in utero, and analysis thereof for genetic defects. A preferred, non-invasive, means of collecting embryonic cells involves separation of embryonic nucleated red blood cell precursors that have infiltrated into peripheral maternal circulation. However, since the quantities of these cells are quite scarce, a further application of the present invention would be the expansion of such cells according to methods described herein, prior to analysis. The present invention, therefore, offers a means to expand embryonic cells for applications in prenatal diagnosis.

Gene therapy: For successful long-term gene therapy, a high frequency of genetically modified stem cells with transgenes stably integrated within their genome, is an obligatory requirement. In BM tissue, while the majority of cells are cycling progenitors and precursors, stem cells constitute only a small fraction of the cell population and most of them are in a quiescent, non-cycling state. Viral-based (e.g., retroviral) vectors require active cell division for integration of the transgene into the host genome. Therefore, gene transfer into fresh BM stem cells is highly inefficient. The ability to expand a purified population of stem cells and to regulate their cell division ex-vivo would provide for an increased probability of their genetic modification (52).

Adoptive immunotherapy: Ex-vivo-expanded, defined lymphoid subpopulations have been studied and used for adoptive immunotherapy of various malignancies, immuno-deficiencies, viral and genetic diseases (53-55).

The treatment enhances the required immune response or replaces deficient functions. This approach was pioneered clinically by Rosenberg et al. (56) using a large number of autologous ex-vivo expanded non-specific killer T cells, and subsequently ex-vivo expanded specific tumor infiltrating lymphocytes.

Functionally active, antigen-presenting cells could be grown from a starting population of $CD34^+$ PB cells in cytokine-supported cultures, as well. These cells can present soluble protein antigens to autologous T cells in-vitro and, thus, offer new prospects for the immunotherapy of minimal residual disease after high dose chemotherapy. Ex-vivo expansion of antigen-presenting dendritic cells has been studied as well, and is an additional promising application of the currently proposed technology (57-59).

Ex-Vivo Expansion of Non-Hematopoietic Stem and Progenitor Cells:

Additional applications of the technology proposed herein include the possibility for ex-vivo expansion of non-hematopoietic stem and progenitor cells, including, for example, neural stem cells, oligodendrocyte progenitors, and the like.

Myelin disorders form an important group of human neurological diseases that are, as yet, incurable. Progress in animal models, particularly in transplanting cells of the oligodendrocyte lineage, has resulted in significant focal remyelination and physiological evidence of restoration of function (60). Future therapies could involve both transplantation and promotion of endogenous repair, and the two approaches could be combined with ex-vivo manipulation of donor tissue.

U.S. Pat. No. 5,486,359 illustrates that isolated human mesenchymal stem cells can differentiate into more than one tissue type (e.g. bone, cartilage, muscle, or marrow stroma) and provides a method for isolating, purifying, and expanding human mesenchymal stem cells in culture.

U.S. Pat. No. 5,736,396 provides methods for in-vitro or ex-vivo lineage-directed induction of isolated, culture-expanded human mesenchymal stem cells comprising mesenchymal stem cell contact with a bioactive factor effective in is inducing stem cell differentiation into a lineage of choice. Further disclosed is a method including introducing culture-expanded lineage-induced mesenchymal stem cells into the original, autologous host, for purposes of mesenchymal tissue regeneration or repair.

U.S. Pat. No. 4,642,120 provides compositions for repairing defects in cartilage and bones. These are provided in gel form either as such, or embedded in natural or artificial bones. The gel comprises certain types of cells. Cells may be committed embryonal chondrocytes or any mesenchymal-origin cells which potentially can be converted to become functional cartilage cells, typically by the inclusion of chondrogenic inducing factors, in combination with fibrinogen, antiprotease and thrombin.

U.S. Pat. No. 5,654,186 illustrates that blood-borne mesenchymal cells proliferate in culture, and in-vivo, as demonstrated in animal models, and are capable of migrating into wound sites from the blood to form skin.

U.S. Pat. No. 5,716,411 reveals a method of skin regeneration of a wound or burn in an animal or human. This method comprises the steps of initially covering the wound with a collagen glycosaminoglycan (GC) matrix, facilitating mesenchymal cell and blood vessel infiltration from healthy underlying tissue within the grafted GC matrix. Subsequently a cultured epithelial autograft sheet grown from epidermal cells taken from the animal or human at a wound-free site is applied on the body surface. The resulting graft has excellent inclusion rates and has the appearance, growth, maturation and differentiation of normal skin.

U.S. Pat. No. 5,716,616 provides methods for treating recipients suffering from diseases, disorders or conditions characterized by bone, cartilage, or lung defects. The methods comprise intravenous administration of stromal cells isolated from normal, syngeneic individuals, or intravenous administration of stromal cells isolated from the recipient subsequent to correction of the genetic defect in the isolated cells. Methods of introducing genes into a recipient individual are also disclosed. The methods comprise obtaining a bone marrow sample from either the recipient individual or a matched syngeneic donor and isolating adherent cells from the sample. Once isolated, donor adherent cells are transfected with a gene and administered to a recipient individual intravenously. Compositions comprising isolated stromal cells that include exogenous genes operably linked to regulatory sequences are disclosed, as well.

In each of the above examples, non-hematopoietic stem and progenitor cells are used as an external source of cells for replenishing missing or damaged cells of an organ. Such use requires high levels of stem and progenitor cell expansion for successful application of the proposed therapies. Because of this pressing need for large numbers of expanded stem and progenitor cell populations, the methods and applications of the present invention address a critical niche in any of the methods disclosed in the above U.S. patents.

Additional Examples for Both Ex-Vivo and In-Vivo Applications:

Additional applications of stem and progenitor cell expansion include skin regeneration, hepatic regeneration, muscle regeneration and stimulation of bone growth for applications in osteoporosis.

Mobilization of bone marrow stem cells into peripheral blood (peripheralization): Effects of retinoic acid, retinoid and/or Vitamin D receptor antagonists have additional in-vivo applications. As mentioned above, PB-derived stem cells for transplantation are "harvested" by repeated leukophoresis following their mobilization from the marrow into the circulation by treatment with chemotherapy and cytokines (46-47).

The use of chemotherapy is, of course, not suitable for normal donors. Administration of antagonists, into the donor could increase the marrow stem cell pool, which is then mobilized into the periphery by endogenous or injected G-CSF.

Stimulation of fetal hemoglobin production: Increased fetal hemoglobin has been shown to ameliorate clinical symptoms in recipients suffering β-hemoglobinopathies, such as sickle cell anemia and β-thalassemia (61).

Fetal hemoglobin, which normally comprises 1% of the total hemoglobin, becomes elevated in accelerated erythropoiesis (e.g., following acute hemolysis or hemorrhage or administration of erythropoietin) (62).

It has been suggested that this phenomenon is associated with acceleration of the maturation/differentiation process of erythroid precursors (63). Administration of retinoic acid, retinoid and/or Vitamin D receptor antagonists to recipients with β-hemoglobinopathies might first increase and synchronize their early erythroid progenitor pool, by blocking progenitor differentiation.

Following cessation of administration of the drug and its removal from the body, this early population then might undergo accelerated maturation, which may result in an elevated production of fetal hemoglobin.

The following description provides more details relating to specific aspects and embodiments of the present invention.

According to one aspect of the present invention there is provided a method of ex-vivo expanding a population of stem cells, while at the same time, substantially inhibiting differentiation of the stem cells ex-vivo. The method according to this aspect of the present invention is effected by providing the stem cells with ex-vivo culture conditions for ex-vivo cell proliferation and, at the same time, for reducing an expression and/or activity of CD38, thereby expanding the population of stem cells while at the same time, substantially inhibiting differentiation of the stem cells ex-vivo.

As used herein, the phrase "stem cells" refers to pluripotent cells that, given the right growth conditions, may develop to any cell lineage present in the organism from which they were derived. The phrase, as used herein, refers both to the earliest renewable cell population responsible for generating cell mass in a tissue or body and the very early progenitor cells, which are somewhat more differentiated, yet are not committed and can readily revert to become a part of the earliest renewable cell population. Methods of ex-vivo culturing stem cells of different tissue origins are well known in the art of cell culturing. To this effect, see for example, the text book "Culture of Animal Cells—A Manual of Basic Technique" by Freshney, Wiley-Liss, N.Y. (1994), Third Edition, the teachings of which are hereby incorporated by reference.

As used herein the term "inhibiting" refers to slowing, decreasing, delaying, preventing or abolishing.

As used herein the term "differentiation" refers to relatively generalized or specialized changes during development. Cell differentiation of various lineages is a well-documented process and requires no further description herein. As used herein the term differentiation is distinct from maturation which is a process, although some times associated with cell division, in which a specific cell type mature to function and then dies, e.g., via programmed cell death.

The phrase "cell expansion" is used herein to describe a process of cell proliferation substantially devoid of cell differentiation. Cells that undergo expansion hence maintain their cell renewal properties and are oftentimes referred to herein as renewable cells, e.g., renewable stem cells.

As used herein the term "ex-vivo" refers to a process in which cells are removed from a living organism and are propagated outside the organism (e.g., in a test tube). As used herein, the term "ex-vivo", however, does not refer to a process by which cells known to propagate only in-vitro, such as various cell lines (e.g., HL-60, MEL, HeLa, etc.) are cultured. In other words, cells expanded ex-vivo according to the present invention do not transform into cell lines in that they eventually undergo differentiation.

Providing the ex-vivo grown cells with conditions for ex-vivo cell proliferation include providing the cells with nutrients and preferably with one or more cytokines, as is further detailed hereinunder.

As mentioned hereinabove, concomitant with treating the cells with conditions which allow for ex-vivo the stem cells to prolifetare, the cells are short-term treated or long-term treated to reduce the expression and/or activity of CD38.

Reducing the activity of CD38 is effected by providing the cells with an agent that inhibits CD38 activity (i.e., a CD38 inhibitor).

As used herein a "CD38 inhibitor" refers to an agent which is capable of down-regulating or suppressing CD38 activity in stem cells.

A CD38 inhibitor according to this aspect of the present invention can be a "direct inhibitor" which inhibits CD38 intrinsic activity or an "indirect inhibitor" which inhibits the activity or expression of CD38 signaling components (e.g., the cADPR and ryanodine signaling pathways) or other signaling pathways which are effected by CD38 activity.

According to presently known embodiments of this aspect of the present invention, nicotinamide is a preferred CD38 inhibitor.

Hence, in one embodiment, the method according to this aspect of the present invention is effected by providing the cells either with nicotinamide itself, or with a nicotinamide analog, a nicotinamide or a nicotinamide analog derivative or a nicotinamide or a nicotinamide analog metabolite.

As used herein, the phrase "nicotinamide analog" refers to any molecule that is known to act similarly to nicotinamide. Representative examples of nicotinamide analogs include, without limitation, benzamide, nicotinethioamide (the thiol analog of nicotinamide), nicotinic acid and α-amino-3-indolepropionic acid.

The phrase "a nicotinamide or a nicotinamide analog derivative" refers to any structural derivative of nicotinamide itself or of an analog of nicotinamide. Examples of such derivatives include, without limitation, substituted benzamides, substituted nicotinamides and nicotinethioamides and N-substituted nicotinamides and nicotinthioamides.

The phrase "a nicotinamide or a nicotinamide analog metabolite" refers to products that are derived from nicotinamide or from analogs thereof such as, for example, NAD, NADH and NADPH.

Alternatively, a CD38 inhibitor according to this aspect of the present invention can be an activity neutralizing antibody which binds for example to the CD38 catalytic domain, thereby inhibiting CD38 catalytic activity. It will be appreciated, though, that since CD38 is an intracellular protein measures are taken to use inhibitors which may be delivered through the plasma membrane. In this respect a fragmented antibody such as a Fab fragment (described hereinunder) is preferably used.

The term "antibody" as used in this invention includes intact molecules as well as functional fragments thereof, such as Fab, F(ab')$_2$, and Fv that are capable of binding to macrophages. These functional antibody fragments are defined as follows:

Fab, the fragment which contains a monovalent antigen-binding fragment of an antibody molecule, can be produced by digestion of whole antibody with the enzyme papain to yield an intact light chain and a portion of one heavy chain;

Fab', the fragment of an antibody molecule that can be obtained by treating whole antibody with pepsin, followed by reduction, to yield an intact light chain and a portion of the heavy chain; two Fab' fragments are obtained per antibody molecule;

(Fab')$_2$, the fragment of the antibody that can be obtained by treating whole antibody with the enzyme pepsin without subsequent reduction; F(ab')$_2$ is a dimer of two Fab' fragments held together by two disulfide bonds;

Fv, defined as a genetically engineered fragment containing the variable region of the light chain and the variable region of the heavy chain expressed as two chains; and Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

Antibody fragments according to the present invention can be prepared by expression in *E. coli* or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of V$_H$ and V$_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise V$_H$ and V$_L$ chains connected by a peptide linker. These single-chain antigen binding proteins (sFv) are prepared by constructing a structural gene comprising DNA sequences encoding the V$_H$ and V$_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins recipient antibody in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, J. Mol. Biol., 227:381 (1991); Marks et al., J. Mol. Biol., 222:581 (1991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

Alternatively, the method according to this aspect of the present invention can be effected by providing the ex-vivo cultured stem cells with an agent that down-regulates CD38 expression.

An agent that downregulates CD38 expression refers to any agent which affects CD38 synthesis (decelerates) or degradation (acelerates) either at the level of the mRNA or at the level of the protein. For eaxmple, a small interfering polynucleotide molecule which is designed to down regulate the expression of CD38 can be used according to this aspect of the present invention.

An example for a small interfering polynucleotide molecule which can down-regulate the expression of CD38 is a small interfering RNA or siRNA, such as, for example, the morpholino antisense oligonucleotides described by in Munshi et al. (Munshi C B, Graeff R, Lee H C, *J Biol Chem* 2002 Dec. 20;277(51):49453-8), which includes duplex oligonucleotides which direct sequence specific degradation of mRNA through the previously described mechanism of RNA interference (RNAi) (Hutvagner and Zamore (2002) Curr. Opin. Genetics and Development 12:225-232).

As used herein, the phrase "duplex oligonucleotide" refers to an oligonucleotide structure or mimetics thereof, which is formed by either a single self-complementary nucleic acid strand or by at least two complementary nucleic acid strands. The "duplex oligonucleotide" of the present invention can be composed of double-stranded RNA (dsRNA), a DNA-RNA hybrid, single-stranded RNA (ssRNA), isolated RNA (i.e., partially purified RNA, essentially pure RNA), synthetic RNA and recombinantly produced RNA.

Preferably, the specific small interfering duplex oligonucleotide of the present invention is an oligoribonucleotide composed mainly of ribonucleic acids.

Instructions for generation of duplex oligonucleotides capable of mediating RNA interference are provided in www.ambion.com.

Hence, the small interfering polynucleotide molecule according to the present invention can be an RNAi molecule (RNA interference molecule).

Alternatively, a small interfering polynucleotide molecule can be an oligonucleotide such as a CD38-specific antisense molecule or a rybozyme molecule, further described hereinunder.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art.

Oligonucleotides used according to this embodiment of the present invention are those having a length selected from a range of 10 to about 200 bases preferably 15-150 bases, more preferably 20-100 bases, most preferably 20-50 bases.

The oligonucleotides of the present invention may comprise heterocyclic nucleosides consisting of purines and the pyrimidines bases, bonded in a 3' to 5' phosphodiester linkage.

Preferably used oligonucleotides are those modified in either backbone, internucleoside linkages or bases, as is broadly described hereinunder. Such modifications can oftentimes facilitate oligonucleotide uptake and resistivity to intracellular conditions.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos.: 687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466, 677; 5,476,925; 5,519,126; 5,536,821; 5,541,306; 5,550,111; 5,563,253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl 10 internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which can be used according to the present invention, are those modified in both sugar and the internucleoside linkage, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374. Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

Another modification of the oligonucleotides of the invention involves chemically linking to the oligonucleotide one or more moieties or conjugates, which enhance the activity, cellular distribution or cellular uptake of the oligonucleotide. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety, as disclosed in U.S. Pat. No. 6,303,374.

It is not necessary for all positions in a given oligonucleotide molecule to be uniformly modified, and in fact more than one of the aforementioned modifications may be incorporated in a single compound or even at a single nucleoside within an oligonucleotide.

As described hereinabove, the oligonucleotides of the present invention are preferably antisense molecules, which are chimeric molecules. "Chimeric antisense molecules" are oligonucleotides, which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target polynucleotide. An additional region of the oligonucleotide may serve as a substrate for enzymes capable of cleaving RNA:DNA or RNA:RNA hybrids. An example for such includes RNase H, which is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense molecules of the present invention may be formed as composite structures of two or more oligonucleotides, modified oligonucleotides, as described above. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein fully incorporated by reference.

The oligonucleotides of the present invention can further comprise a ribozyme sequence. Rybozymes are being increasingly used for the sequence-specific inhibition of gene expression by the cleavage of mRNAs. Several rybozyme sequences can be fused to the oligonucleotides of the present invention. These sequences include but are not limited ANGIOZYME specifically inhibiting formation of the VEGF-R (Vascular Endothelial Growth Factor receptor), a key component in the angiogenesis pathway, and HEP-TAZYME, a rybozyme designed to selectively destroy Hepatitis C Virus (HCV) RNA, (Rybozyme Pharmaceuticals, Incorporated—WEB home page).

Further alternatively, a small interfering polynucleotide molecule, according to the present invention can be a DNAzyme.

DNAzymes are single-stranded catalytic nucleic acid molecules. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, LM Curr Opin Mol Ther 2002;4:119-21).

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther www.asgt.org). In another application, DNAzymes complementary to bcr-abl oncogenes were successful in inhibiting the oncogenes expression in leukemia cells, and lessening relapse rates in autologous bone marrow transplant in cases of CML and ALL.

Alternatively, as described hereinabove, retinoid receptor superfamily inhibitors (e.g., antagonists, siRNA molecules, antisense molecules, antibodies, etc.) which downregulate or suppress retinoid receptor activity and/or expression can be used to down regulate CD38 expression.

Briefly, as is described hereinabove, retinoid receptors such as RAR, RXR and VDR have been reported to be involved in the regulation of gene expression pathways associated with cell proliferation and differentiation and in particular in the regulation of CD38 expression (24, 25). Hence, preferred agents that downregulate CD38 expression according to the present invention include RAR antagonists, RXR antagonists and VDR antagonists or, alternatively, antagonists for reducing the capacity of the stem cells in responding to retinoic acid, retinoid and/or Vitamin D.

As used herein the term "antagonist" refers to an agent that counteracts or abrogates the effects of an agonist or a natural ligand of a receptor. Further features relating to such antagonists are detailed hereinunder.

Each of the agents described hereinabove may reduce the expression or activity of CD38 individually. However, the present invention aims to also encompas the use of any subcombination of these agents.

It will be appreciated that protein agents (e.g., antibodies) of the present invention can be expressed from a polynucleotide encoding same and provided to ex-vivo cultured stem cells employing an appropriate gene delivery vehicle/method and a nucleic acid construct as is further described hereinunder.

Examples of suitable constructs include, but are not limited to pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com). Examples of retroviral vector and packaging systems are those sold by Clontech, San Diego, Calif., including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter.

As the method of ex-vivo expanding a population of stem cells, while at the same time, substantially inhibiting differentiation of the stem cells ex-vivo, according to this aspect of the present invention, is effected by modulating CD38 expression and/or activity, either at the protein level, using RAR, RXR or VDR antagonists or a CD38 inhibitor such as nicotinamide and analogs thereof, or at the at the expression level via genetic engineering techniques, as is detailed hereinabove, there are further provided, according to the present invention, several preferred methods of ex-vivo expanding a population of stem cells, while at the same time, substantially inhibiting differentiation of the stem cells ex-vivo.

In one particular, a method of ex-vivo expanding a population of stem cells, while at the same time, substantially inhibiting differentiation of the stem cells ex-vivo is effected by providing the stem cells with ex-vivo culture conditions for ex-vivo cell proliferation and, at the same time, for reducing a capacity of the stem cells in responding to retinoic acid, retinoids and/or Vitamin D, thereby expanding the population of stem cells while at the same time, substantially inhibiting differentiation of the stem cells ex-vivo.

Reducing the capacity of the cells in responding to retinoic acid, retinoids and/or Vitamin D, or to retinoic acid, retinoid X and/or Vitamin D receptor signaling may be effected, for example, by the administration of chemical inhibitors, including receptor antagonists.

In another particular, the method of ex-vivo expanding a population of stem cells, while at the same time, substantially inhibiting differentiation of the stem cells ex-vivo is effected by providing the stem cells with ex-vivo culture conditions for ex-vivo cell proliferation and, at the same time, for reducing a capacity of the stem cells in responding to signaling pathways involving the retinoic acid receptor, retinoid-X receptor and/or Vitamin D receptor, thereby expanding the population of stem cells while at the same time, substantially inhibiting differentiation of the stem cells ex-vivo.

Reducing the capacity of the cells to respond to retinoic acid, retinoid X and/or Vitamin D receptor signaling events, includes treating the cells with antagonists supplied continuously or for a short-pulse period, and is effected by a diminution or abrogation of cellular signaling pathways through their respective, cognate receptors.

Final concentrations of the antagonists may be, depending on the specific application, in the micromolar or millimolar ranges. For example, within about 0.1 μM to about 100 mM, preferably within about 4 μM to about 50 mM, more preferably within about 5 μM to about 40 mM.

In still another particular, the method of ex-vivo expanding a population of stem cells, while at the same time, substantially inhibiting differentiation of the stem cells ex-vivo is effected by providing the stem cells with ex-vivo culture conditions for ex-vivo cell proliferation and with nicotinamide, a nicotinamide analog, a nicotinamide or a nicotinamide analog derivative or a nicotinamide or a nicotinamide analog metabolite, thereby expanding the population of stem cells while at the same time, substantially inhibiting differentiation of the stem cells ex-vivo.

Final concentrations of the nicotinamide or the analogs, derivatives or metabolites thereof are preferably, depending on the specific application, in the millimolar ranges. For example, within about 0.1 mM to about 20 mM, preferably within about 1 mM to about 10 mM, more preferably within about 5 mM to about 10 mM.

The ex-vivo expansion of populations of stem cells, according to the features described hereinabove, can be utilized for expanding a population of hematopoietic renewable stem cells ex-vivo.

Hence, according to another aspect of the present invention, there is provided a method of ex-vivo expanding a population of hematopoietic renewable stem cells ex-vivo. The method is effected by obtaining adult or neonatal umbilical cord whole white blood cells (also known in the art as mononuclear cell fraction) or whole bone marrow cells sample and providing the cells in the sample with ex-vivo culture conditions for stem cells ex-vivo cell proliferation and, at the same time, for reducing the expression and/or activity of CD38, as is described hereinabove, thereby expanding a population of a renewable stem cells in the sample.

In one particular embodiment of this aspect of the present invention, this method is effected by obtaining adult or neonatal umbilical cord whole white blood cells or whole bone marrow cells sample and providing the cells in the sample with ex-vivo culture conditions for stem cells ex-vivo cell proliferation and, at the same time, for reducing a capacity of the stem cells in responding to retinoic acid, retinoids and/or Vitamin D, thereby expanding a population of a renewable stem cells in the sample.

In another particular embodiment of this aspect of the present invention, the method is effected by obtaining adult or neonatal umbilical cord whole white blood cells or whole bone marrow cells sample and providing the cells in the sample with ex-vivo culture conditions for stem cells ex-vivo cell proliferation and, at the same time, for reducing a capacity of the stem cells in responding to signaling pathways involving the retinoic acid receptor, the retinoid X receptor and/or the Vitamin D receptor, thereby expanding a population of a renewable stem cells in the sample.

In still another particular embodiment of this aspect of the present invention, the method is effected by obtaining adult or neonatal umbilical cord whole white blood cells or whole bone marrow cells sample and providing the cells in the sample with ex-vivo culture conditions for stem cells ex-vivo cell proliferation and with nicotinamide, a nicotinamide analog, a nicotinamide or a nicotinamide analog derivative or a nicotinamide or a nicotinamide analog metabolite, thereby expanding a population of a renewable stem cells in the sample.

Expanding the population of stem cells can be further utilized, according to the present invention, in in vivo settings, such that according to still another aspect of the present invention there is provided a method of in-vivo expanding a population of stem cells, while at the same time, substantially inhibiting differentiation of the stem cells in-vivo. The method, according to this aspect of the present invention is effected by administering to a subject in need thereof a therapeutically effective amount of an agent, the agent serves for reducing an expression and/or activity of CD38, according to the features described hereinabove.

In one particular embodiment of this aspect of the present invention, the method is effected by administering to a subject in need thereof a therapeutically effective amount of an agent, which serves for reducing a capacity of the stem cells in responding to retinoic acid, retinoids and/or Vitamin D, as is defined hereinabove.

In another particular embodiment of this aspect of the present invention, the method is effected by administering to a subject in need thereof a therapeutically effective amount of an agent, which serves for reducing a capacity of the stem cells in responding to signaling pathways involving the retinoic acid receptor, retinoid-X receptor and/or Vitamin D receptor, as is defined hereinabove.

In still another particular embodiment of this aspect of the present invention, the method is effected by administering to a subject in need thereof a therapeutically effective amount of an agent selected from the group consisting of nicotinamide, a nicotinamide analog, a nicotinamide or a nicotinamide analog derivative and a nicotinamide or a nicotinamide analog metabolite.

As used herein throughout, the phrase "therapeutically effective amount" or "effective amount" refers to that amount of the agent being administered which will induce expansion of stem cells yet will limit the differentiation thereof.

The methods described hereinabove for ex-vivo expanding stem cells populations can result, inter alia, in an expanded population of stem cells.

Thus, further according to an aspect of the present invention there is is provided an ex-vivo expanded population of hematopoietic stem cells which comprises a plurality of cells characterized by 3-20% of the cells being reselectable $CD34^+$ cells, of which at least 40% of cells are $CD34^+_{dim}$, i.e., fall below the median intensity in a FACS analysis, wherein, in the reselectable $CD34^+$ cells, a majority of cells which are $Lin^-$ are also $CD34^+_{dim}$ cells. In one embodiment, the hematopoietic stem cells are derived from a source selected from the group consisting of bone marrow, peripheral blood and neonatal umbilical cord blood. In another embodiment, the population of cells has a single genetic background. In yet another embodiment, the ex-vivo expanded population of hematopoietic stem cells comprises at least N cells derived from a single donor, wherein N equals the average number of $CD34^+$ cells derived from one sample of neonatal umbilical cord blood, bone marrow, or peripheral blood multiplied by 1,000. Cell surface expression of the CD34 and/or Lin markers can be determined, for example, via FACS analysis or immunohistological staining techniques. A self renewal potential of the stem cells can be determined in-vitro by long term colony formation (LTC-CFUc), as is further exemplified in the Examples section that follows, or by in-vivo engraftment in the SCID-Hu mouse model. The SCID-Hu mouse model employs C.B-17 scid/scid (SCID) mice transplanted with human fetal thymus and liver tissue or fetal BM tissue and provides an appropriate model for the evaluation of putative human hematopoietic stem cells. Because of the reconstitution of the SCID mice with human fetal tissue, the model affords the proliferation of stem cells, in this case human hematopoietic stem cells to proliferate, and function in the hematopoietic microenvironment of human origin. Mice are typically irradiated, then delivered stem cells into the grafts, and reconstitution is measured by any number of methods, including FACS and immunohistochemistry of repopulated organs (Humeau L., et al Blood (1997) 90:3496).

Additionally, the methods described hereinabove can be utilized to produce transplantable hematopoietic cell preparations, such that according to yet another aspect of the present invention there is provided a transplantable hematopoietic cell preparation, which comprises an expanded population of hematopoietic stem cells propagated ex-vivo in the presence of an effective amount of an agent, which reduces the expression and/or activity of CD38, as described hereinabove, while at the same time, substantially inhibiting differentiation of the stem cells; and a pharmaceutically acceptable carrier. Hence, cell populations of the invention can be administered in a pharmaceutically acceptable carrier or diluent, such as sterile saline and aqueous buffer solutions. The use of such carriers and diluents is well known in the art.

In a particular embodiment of this aspect of the present invention, the transplantable hematopoietic cell preparation comprises an expanded population of hematopoietic stem cells propagated ex-vivo in the presence of an effective amount of an agent, which reduces a capacity of the stem cells in responding to retinoic acid, retinoids and/or Vitamin D, while at the same time, substantially inhibiting differentiation of the stem cells; and a pharmaceutically acceptable carrier.

In another particular embodiment of this aspect of the present invention, the transplantable hematopoietic cell preparation comprises an expanded population of hematopoietic stem cells propagated ex-vivo in the presence of an effective amount of an agent, which reduces a capacity of the stem cells in responding to retinoic acid receptor, retinoid X receptor and/or Vitamin D receptor signaling, while at the same time, substantially inhibiting differentiation of the stem cells; and a pharmaceutically acceptable carrier.

In still another particular embodiment of this aspect of the present invention, the transplantable hematopoietic cell preparation comprises an expanded population of hematopoietic stem cells propagated ex-vivo in the presence of an effective amount of an agent selected from the group consisting of nicotinamide, a nicotinamide analog, a nicotinamide or a nicotinamide is analog derivative and a nicotinamide or a nicotinamide analog metabolite; and a pharmaceutically acceptable carrier.

The ability of the agents of the present invention to inhibit differentiation of stem cells can be further used in various technical applications:

According to a further aspect of the present invention there is provided a method of preserving stem cells. In one embodiment, the method is effected by handling the stem cell in at least one of the following steps: harvest, isolation and/or storage, in a presence of an effective amount of a retinoic acid receptor antagonist, a retinoid X receptor antagonist and/or a Vitamin D receptor antagonist. Alternatively, the method is effected by handling the stem cell in at least one of the following steps: harvest, isolation and/or storage, in a presence of an effective amount of nicotinamide, a nicotinamide analog, a nicotinamide or a nicotinamide analog derivative or a nicotinamide or a nicotinamide analog metabolite.

According to still a further aspect of the present invention there is provided a cells collection/culturing bag. The cells collection/culturing bag of the present invention is supplemented with an effective amount of a retinoic acid receptor antagonist, a retinoid X receptor antagonist and/or a Vitamin D receptor antagonist, which substantially inhibits cell differentiation. Alternatively, the cells collection/culturing bag of the present invention is supplemented with an effective amount of nicotinamide, a nicotinamide analog, a nicotinamide or a nicotinamide analog derivative or a nicotinamide or a nicotinamide analog metabolite.

According to the present invention there is also provided a cells separation and/or washing buffer. The separation and/or washing buffer is supplemented with an effective amount of a retinoic acid receptor antagonist, a retinoid X receptor antagonist and/or Vitamin D receptor antagonists, which substantially inhibit cell differentiation and induce cell expansion. Alternatively, the separation and/or washing buffer is supplemented with an effective amount of nicotinamide, a nicotinamide analog, a nicotinamide or a nicotinamide analog derivative or a nicotinamide or a nicotinamide analog metabolite.

As is further detailed below, stem cells may serve to exert cellular gene therapy.

Gene therapy as used herein refers to the transfer of genetic material (e.g., DNA or RNA) of interest into a host to treat or prevent a genetic or acquired disease or condition or phenotype. The genetic material of interest encodes a product (e.g., a protein, polypeptide, peptide, functional RNA, antisense) whose production in vivo is desired. For example, the genetic material of interest can encode a hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (i) ex-vivo or cellular gene therapy; and (ii) in vivo gene therapy. In ex-vivo gene therapy cells are removed from a patient, and while being cultured are treated in-vitro. Generally, a functional replacement gene is introduced into the cells via an appropriate gene delivery vehicle/method (transfection, transduction, homologous recombination, etc.) and an expression system as needed and then the modified cells are expanded in culture and returned to the host/patient. These genetically re-implanted cells have been shown to express the transfected genetic material in situ.

Hence, further according to an aspect of the present invention, there is provided a method of genetically modifying stem cells with an exogene. The method, according to this aspect of the present invention, is effected by (a) obtaining stem cells to be genetically modified; (b) providing the stem cells with ex-vivo culture conditions for cell proliferation and, at the same time, for reducing an expression and/or activity of CD38, thereby expanding a population of the stem cells, while at the same time, substantially inhibiting differentiation of the stem cells ex-vivo; and (c) genetically modifying the stem cells with the exogene. It is clear that the order of step (b) and (c) can be reversed.

In a particular embodiment of this aspect of the present invention, the method is effected by (a) obtaining stem cells to be genetically modified; (b) providing the stem cells with ex-vivo culture conditions for cell proliferation and, at the same time, for reducing a capacity of the stem cells in responding to retinoic acid, retinoids and/or Vitamin D, thereby expanding a population of the stem cells, while at the same time, substantially inhibiting differentiation of the stem cells ex-vivo; and (c) genetically modifying the stem cells with the exogene.

In another particular embodiment of this aspect of the present invention, the method is effected by (a) obtaining stem cells to be genetically modified; (b) providing the stem cells with ex-vivo culture conditions for cell proliferation and, at the same time, for reducing a capacity of the stem cells in responding to signaling pathways involving the retinoic acid receptor and/or the retinoid X receptor and/or the Vitamin D receptor, thereby expanding a population of the stem cells, while at the same time, substantially inhibiting differentiation of the stem cells ex-vivo; and (c) genetically modifying the stem cells with the exogene. In still another particular embodiment of this aspect of the present invention, the method is effected by (a) obtaining stem cells to be genetically modified; (b) providing the stem cells with ex-vivo culture conditions for cell proliferation and with nicotinamide, a nicotinamide analog, a nicotinamide or a nicotinamide analog derivative or a nicotinamide or a nicotinamide analog metabolite, thereby expanding a population of the stem cells, while at the same time, substantially inhibiting differentiation of the stem cells ex-vivo; and (c) genetically modifying the stem cells with the exogene.

In a preferred embodiment, genetically modifying the cells is effected by a vector, which comprises the exogene or transgene, which vector is, for example, a viral vector or a nucleic acid vector. Many viral vectors suitable for use in cellular gene therapy are known, examples are provided hereinbelow. Similarly, a range of nucleic acid vectors can be used to genetically transform the expanded cells of the invention, as is further described below.

Accordingly, the expanded cells of the present invention can be modified to express a gene product. As used herein, the phrase "gene product" refers to proteins, peptides and functional RNA molecules. Generally, the gene product encoded by the nucleic acid molecule is the desired gene product to be supplied to a subject. Examples of such gene products include proteins, peptides, glycoproteins and lipoproteins normally produced by an organ of the recipient subject. For example, gene products which may be supplied by way of gene replacement to defective organs in the pancreas include insulin, amylase, protease, lipase, trypsinogen, chymotrypsinogen, carboxypeptidase, ribonuclease, deoxyribonuclease, triaclyglycerol lipase, phospholipase $A_2$, elastase, and amylase; gene products normally produced by the liver include blood clotting factors such as blood clotting Factor VIII and Factor IX, UDP glucuronyl transferae, ornithine transcarbanoylase, and cytochrome p450 enzymes, and adenosine deaminase, for the processing of serum adenosine or the endocytosis of low density lipoproteins; gene products produced by the thymus include serum thymic factor, thymic humoral factor, thymopoietin, and thymosin $\alpha_1$; gene products produced by the digestive tract cells include gastrin, secretin, cholecystokinin, somatostatin, serotinin, and substance P.

Alternatively, the encoded gene product is one, which induces the expression of the desired gene product by the cell (e.g., the introduced genetic material encodes a transcription factor, which induces the transcription of the gene product to be supplied to the subject).

In still another embodiment, the recombinant gene can provide a heterologous protein, e.g., not native to the cell in which it is expressed. For instance, various human MHC components can be provided to non-human cells to support engraftment in a human recipient. Alternatively, the transgene is one, which inhibits the expression or action of a donor MHC gene product normally expressed in the micro-organ explant.

A nucleic acid molecule introduced into a cell is in a form suitable for expression in the cell of the gene product encoded by the nucleic acid. Accordingly, the nucleic acid molecule includes coding and regulatory sequences required for transcription of a gene (or portion thereof) and, when the gene product is a protein or peptide, translation of the gene acid molecule include promoters, enhancers and polyadenylation signals, as well as sequences necessary for transport of an encoded protein or peptide, for example N-terminal signal sequences for transport of proteins or peptides to the surface of the cell or secretion.

Nucleotide sequences which regulate expression of a gene product (e.g., promoter and enhancer sequences) are selected based upon the type of cell in which the gene product is to be expressed and the desired level of expression of the gene product. For example, a promoter known to confer cell-type specific expression of a gene linked to the promoter can be used. A promoter specific for myoblast gene expression can be linked to a gene of interest to confer muscle-specific expression of that gene product. Muscle-specific regulatory elements, which are known in the art, include upstream regions from the dystrophin gene (Klamut et al., (1989) *Mol. Cell Biol.* 9: 2396), the creatine kinase gene (Buskin and Hauschka, (1989) *Mol. Cell Biol.* 9: 2627) and the troponin gene (Mar and Ordahl, (1988) *Proc. Natl. Acad. Sci. USA.* 85: 6404). Regulatory elements specific for other cell types are known in the art (e.g., the albumin enhancer for liver-specific expression; insulin regulatory elements for pancreatic islet cell-specific expression; various neural cell-specific regulatory elements, including neural dystrophin, neural enolase and A4 amyloid promoters).

Alternatively, a regulatory element, which can direct constitutive expression of a gene in a variety of different cell types, such as a viral regulatory element, can be used. Examples of viral promoters commonly used to drive gene expression include those derived from polyoma virus, Adenovirus 2, cytomegalovirus and Simian Virus 40, and retroviral LTRs.

Alternatively, a regulatory element, which provides inducible expression of a gene linked thereto, can be used. The use of an inducible regulatory element (e.g., an inducible promoter) allows for modulation of the production of the gene product in the cell. Examples of potentially useful inducible regulatory systems for use in eukaryotic cells include hormone-regulated elements (e.g., see Mader, S. and White, J. H. (1993) *Proc. Natl. Acad. Sci. USA* 90: 5603-5607), synthetic ligand-regulated elements (see, e.g., Spencer, D. M. et al 1993) *Science* 262: 1019-1024) and ionizing radiation-regulated elements (e.g., see Manome, Y. Et al. (1993) *Biochemistry* 32: 10607-10613; Datta, R. et al. (1992) *Proc. Natl. Acad. Sci. USA* 89: 1014-10153). Additional tissue-specific or inducible regulatory systems, which may be developed, can also be used in accordance with the invention.

There are a number of techniques known in the art for introducing genetic material into a cell that can be applied to modify a cell of the invention.

In one embodiment, the nucleic acid is in the form of a naked nucleic acid molecule. In this situation, the nucleic acid molecule introduced into a cell to be modified consists only of the nucleic acid encoding the gene product and the necessary regulatory elements.

Alternatively, the nucleic acid encoding the gene product (including the necessary regulatory elements) is contained within a plasmid vector. Examples of plasmid expression vectors include CDM8 (Seed, B. (1987) *Nature* 329: 840) and pMT2PC (Kaufman, et al. (1987) *EMBO J.* 6: 187-195).

In another embodiment, the nucleic acid molecule to be introduced into a cell is contained within a viral vector. In this situation, the nucleic acid encoding the gene product is inserted into the viral genome (or partial viral genome). The regulatory elements directing the expression of the gene product can be included with the nucleic acid inserted into the viral genome (i.e., linked to the gene inserted into the viral genome) or can be provided by the viral genome itself.

Naked nucleic acids can be introduced into cells using calcium-phosphate mediated transfection, DEAE-dextran mediated transfection, electroporation, liposome-mediated transfection, direct injection, and receptor-mediated uptake.

Naked nucleic acid, e.g., DNA, can be introduced into cells by forming a precipitate containing the nucleic acid and calcium phosphate. For example, a HEPES-buffered saline solution can be mixed with a solution containing calcium chloride and nucleic acid to form a precipitate and the precipitate is then incubated with cells. A glycerol or dimethyl sulfoxide shock step can be added to increase the amount of nucleic acid taken up by certain cells. $CaPO_4$-mediated transfection can be used to stably (or transiently) transfect cells and is only applicable to in vitro modification of cells. Protocols for $CaPO_4$-mediated transfection can be found in Current Protocols in Molecular Biology, Ausubel, F. M. et al. (eds.) Greene Publishing Associates, (1989), Section 9.1 and in Molecular Cloning: A Laboratory Manual, 2nd Edition, Sambrook et al. Cold Spring Harbor Laboratory Press, (1989), Sections 16.32-16.40 or other standard laboratory manuals.

Naked nucleic acid can be introduced into cells by forming a mixture of the nucleic acid and DEAE-dextran and incubating the mixture with the cells. A dimethylsulfoxide or chloroquine shock step can be added to increase the amount of nucleic acid uptake. DEAE-dextran transfection is only applicable to in vitro modification of cells and can be used to introduce DNA transiently into cells but is not preferred for creating stably transfected cells. Thus, this method can be used for short-term production of a gene product but is not a method of choice for long-term production of a gene product. Protocols for DEAE-dextran-mediated transfection can be found in Current Protocols in Molecular Biology, Ausubel, F. M. et al. (eds.) Greene Publishing Associates (1989), Section 9.2 and in Molecular Cloning: A Laboratory Manual, 2nd Edition, Sambrook et al. Cold Spring Harbor Laboratory Press, (1989), Sections 16.41-16.46 or other standard laboratory manuals.

Naked nucleic acid can also be introduced into cells by incubating the cells and the nucleic acid together in an appropriate buffer and subjecting the cells to a high-voltage electric pulse. The efficiency with which nucleic acid is introduced into cells by electroporation is influenced by the strength of the applied field, the length of the electric pulse, the temperature, the conformation and concentration of the DNA and the ionic composition of the media. Electroporation can be used to stably (or transiently) transfect a wide variety of cell types and is only applicable to in vitro modification of cells. Protocols for electroporating cells can be found in Current Protocols in Molecular Biology, Ausubel F. M. et al. (eds.) Greene Publishing Associates, (1989), Section 9.3 and in Molecular Cloning: A Laboratory Manual, 2nd Edition, Sambrook et al. Cold Spring Harbor Laboratory Press, (1989), Sections 16.54-16.55 or other standard laboratory manuals.

Another method by which naked nucleic acid can be introduced into cells includes liposome-mediated transfection (lipofection). The nucleic acid is mixed with a liposome suspension containing cationic lipids. The DNA/liposome complex is then incubated with cells. Liposome mediated transfection can be used to stably (or transiently) transfect cells in culture in vitro. Protocols can be found in Current Protocols in Molecular Biology, Ausubel F. M. et al. (eds.) Greene Publishing Associates, (1989), Section 9.4 and other standard laboratory manuals. Additionally, gene delivery in vivo has been accomplished using liposomes. See for example Nicolau et al. (1987) *Meth. Enz.* 149:157-176; Wang and Huang (1987) *Proc. Natl. Acad. Sci. USA* 84:7851-7855; Brigham et al. (1989) *Am. J. Med. Sci.* 298:278; and Gould-Fogerite et al. (1989) *Gene* 84:429-438.

Naked nucleic acid can also be introduced into cells by directly injecting the nucleic acid into the cells. For an in vitro culture of cells, DNA can be introduced by microinjection. Since each cell is microinjected individually, this approach is very labor intensive when modifying large numbers of cells. However, a situation wherein microinjection is a method of choice is in the production of transgenic animals (discussed in greater detail below). In this situation, the DNA is stably introduced into a fertilized oocyte, which is then allowed to develop into an animal. The resultant animal contains cells carrying the DNA introduced into the oocyte. Direct injection has also been used to introduce naked DNA into cells in vivo (see e.g., Acsadi et al. (1991) *Nature* 332:815-818; Wolff et al. (1990) *Science* 247:1465-1468). A delivery apparatus (e.g., a "gene gun") for injecting DNA into cells in vivo can be used. Such an apparatus is commercially available (e.g., from BiO-Rad).

Naked nucleic acid can be complexed to a cation, such as polylysine, which is coupled to a ligand for a cell-surface receptor to be taken up by receptor-mediated endocytosis (see for example Wu, G. and Wu, C. H. (1988) *J. Biol. Chem.* 263: 14621; Wilson et al. (1992) *J. Biol. Chem.* 267: 963-967; and U.S. Pat. No. 5,166,320). Binding of the nucleic acid-ligand complex to the receptor facilitates uptake of the DNA by receptor-mediated endocytosis. Receptors to which a DNA-ligand complex has targeted include the transferrin receptor and the asialoglycoprotein receptor. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88: 8850; Cristiano et al. (1993) *Proc. Natl. Acad. Sci. USA* 90: 2122-2126). Receptor-mediated DNA uptake can be used to introduce DNA into cells either in vitro or in vivo and, additionally, has the added feature that DNA can be selectively targeted to a particular cell type by use of a ligand which binds to a receptor selectively expressed on a target cell of interest.

Generally, when naked DNA is introduced into cells in culture (e.g., by one of the transfection techniques described above) only a small fraction of cells (about 1 out of $10^5$) typically integrate the transfected DNA into their genomes (i.e., the DNA is maintained in the cell episomally). Thus, in order to identify cells, which have taken up exogenous DNA, it is advantageous to transfect nucleic acid encoding a selectable marker into the cell along with the nucleic acid(s) of interest. Preferred selectable markers include those, which confer resistance to drugs such as G418, hygromycin and methotrexate. Selectable markers may be introduced on the same plasmid as the gene(s) of interest or may be introduced on a separate plasmid.

A preferred approach for introducing nucleic acid encoding a gene product into a cell is by use of a viral vector containing nucleic acid, e.g., a cDNA, encoding the gene product. Infection of cells with a viral vector has the advantage that a large proportion of cells receive the nucleic acid which can obviate the need for selection of cells which have received the nucleic acid. Additionally, molecules encoded within the viral vector, e.g., a cDNA contained in the viral vector, are expressed efficiently in cells which have taken up viral vector nucleic acid and viral vector systems can be used either in vitro or in vivo.

Defective retroviruses are well characterized for use in gene transfer for gene therapy purposes (for review see Miller, A. D. (1990) *Blood* 76: 271). A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions, which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM, which are well known to those skilled in the art. Examples of suitable packaging virus lines include ψCrip, ψCrip, ψ2 and ψAm. Retroviruses have been used to introduce a variety of genes into many different cell types, including epithelial cells endothelial cells, lymphocytes, myoblasts, hepatocytes, bone marrow cells, in vitro and/or in vivo (see for example Eglitis, et al. (1985) *Science* 230: 1395-1398; Danosand Mulligan (1988) *Proc. Natl. Acad. Sci. USA* 85: 6460-6464; Wilson et al. (1988) *Proc. Natl. Acad. Sci USA* 85:3014-3018; Armentano et al., (1990) Proc. Natl. Acad. Sci. USA 87: 6141-6145; Huber et al. (1991) Proc. Natl. Acad. Sci. USA 88: 8039-8043; Feri et al. (1991) Proc. Natl. Acad. Sci. USA 88:8377-8381; Chowdhury et al. (1991) *Science* 254: 1802-1805; van Beusechem et al. (1992) Proc. Natl. Acad. Sci USA 89:7640-7644; Kay et al. (1992) *Human Gene Therapy* 3:641-647; Dai et al. (1992) *Proc. Natl. Acad. Sci. USA* 89:10892-10895; Hwu et al (1993) J. Immunol. 150:4104-4115; U.S. Pat. No. 4,868,116; U.S. Pat. No. 4,980, 286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

The genome of an adenovirus can be manipulated such that it encodes and expresses a gene product of interest but it is inactivated in terms of its ability to replicate in a normal lytic viral life cycle. See for example Berkner et al. (1988) *BioTechniques* 6:616; Rosenfeld et al. (1991) *Science* 252:431434; and Rosenfeld et al. (1992) *Cell* 68:143-155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci.* USA 89: 6482-6486), hepatocytes (Herz and Gerard (1993) *Proc. Natl. Acad. Sci. USA* 90: 2812-2816) and muscle cells (Quantin et al. (1992) *Proc. Natl. Acad. Sci. USA* 89: 2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol* 57: 267). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics In Micro. And Immunol.* (1992) 158: 97-129). It is also one of the few viruses that may integrate its DNA into non-dividing cells, and exhibits a high frequency of stable integration (see for example Flotte et al. (1992) *Am. J. Respir. Cell. Mol. Biol.* 7: 349-356; Samulski et al. (1989) *J. Virol.* 63:3822-3828; and McLaughlin et al (1989) J. Virol. 62: 1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5: 3251-3260 can be used to introduce DNA into cells. A variety of nucleic acids have been introduced into different cell types using AAV vectors (see for example Hermonat et al. (1984) *Proc. Natl. Acad. Sci. USA* 81: 6466-6470; Tratschin et al. (1985) *Mol. Cell Biol.* 4: 2072-2081; Wondisford et al. (1988) *Mol. Endocrinol.* 2:32-39; Tratschin et al. (1984) *J. Virol.* 51: 611-619; and Flotte et al. (1993) J. Biol. Chem. 268: 3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be interest to be expressed by a cell is not readily assayable, an expression system can first be optimized using a reporter gene linked to the regulatory elements and vector to be used. The reporter gene encodes a gene product, which is easily detectable and, thus, can be used to evaluate efficacy of the system. Standard reporter genes used in the art include genes encoding β-galactosidase, chloramphenicol acetyl transferase, luciferase and human growth hormone.

When the method used to introduce nucleic acid into a population of cells results in modification of a large proportion of the cells and efficient expression of the gene product by the cells (e.g., as is often the case when using a viral expression vector), the modified population of cells may be used without further isolation or subcloning of individual cells within the population. That is, there may be sufficient production of the gene product by the population of cells such that no further cell isolation is needed. Alternatively, it may be desirable to grow a homogenous population of identically modified cells from a single modified cell to isolate cells, which efficiently express the gene product.

Such a population of uniform cells can be prepared by isolating a single modified cell by limiting dilution cloning followed by expanding the single cell in culture into a clonal population of cells by standard techniques.

As is discussed in detail hereinabove, ex-vivo expansion of stem cells can be advantageously utilized in hematopoietic cells transplantation or implantation. Hence, according to another aspect of the present invention there is provided a method of hematopoietic cells transplantation or implantation. The method according to this aspect of the present invention is effected by (a) obtaining hematopoietic stem cells to be transplanted from a donor; (b) providing the stem cells with ex-vivo culture conditions for cell proliferation and, at the same time, for reducing an expression and/or activity of CD38, thereby expanding the population of the stem cells, while at the same time, substantially inhibiting differentiation of the stem cells ex-vivo; and (c) transplanting or implanting the stem cells to a recipient.

In a particular embodiment of this aspect of the present invention, the method is effected by (a) obtaining hematopoietic stem cells to be transplanted from a donor; (b) providing the stem cells with ex-vivo culture conditions for cell proliferation and, at the same time, for reducing a capacity of the stem cells in responding to retinoic acid, retinoids and/or Vitamin D, thereby expanding the population of the stem cells, while at the same time, substantially inhibiting differentiation of the stem cells ex-vivo; and (c) transplanting or implanting the stem cells to a recipient.

In another particular embodiment of this aspect of the present invention, the method is effected by (a) obtaining hematopoietic stem cells to be transplanted from a donor; (b) providing the stem cells with ex-vivo culture conditions for cell proliferation and, at the same time, for reducing a capacity of the stem cells in responding to signaling pathways involving the retinoic acid receptor, the retinoid X receptor and/or the Vitamin D receptor, thereby expanding the population of the stem cells, while at the same time, substantially inhibiting differentiation of the stem cells ex-vivo; and (c) transplanting or implanting the stem cells to a recipient.

In still another particular embodiment of this aspect of the present invention, the method is effected by (a) obtaining hematopoietic stem cells to be transplanted from a donor; (b) providing the stem cells with ex-vivo culture conditions for cell proliferation and with nicotinamide, a nicotinamide analog, a nicotinamide or a nicotinamide analog derivative or a nicotinamide or a nicotinamide analog metabolite, thereby expanding the population of the stem cells, while at the same time, substantially inhibiting differentiation of the stem cells ex-vivo; and (c) transplanting or implanting the stem cells to a recipient.

The donor and the recipient can be a single individual or different individuals, for example, allogeneic individuals. When allogeneic transplantation is practiced, regimes for reducing implant rejection and/or graft vs. host disease, as well know in the art, should be undertaken. Such regimes are currently practiced in human therapy. Most advanced regimes are disclosed in publications by Slavin S. et al., e.g., J Clin Immunol (2002) 22: 64, and J Hematother Stem Cell Res (2002) 11: 265), Gur H. et al. (Blood (2002) 99: 4174), and Martelli M F et al, (Semin Hematol (2002) 39: 48), which are incorporated herein by reference.

According to yet another aspect of the present invention there is provided a method of adoptive immunotherapy. The method according to this aspect of the present invention is effected by (a) obtaining hematopoietic stem cells from a recipient; (b) providing the stem cells with ex-vivo culture conditions for cell proliferation and, at the same time, for reducing an expression and/or activity of CD38, thereby expanding a population of the stem cells, while at the same time, substantially inhibiting differentiation of the stem cells; and (c) transplanting the stem cells to the recipient.

In a particular embodiment of this aspect of the present invention, the method is effected by (a) obtaining hematopoietic stem cells from a recipient; (b) providing the stem cells with ex-vivo culture conditions for cell proliferation and, at the same time, for reducing a capacity of the stem cells in responding to retinoic acid, retinoids and/or Vitamin D, thereby expanding a population of the stem cells, while at the same time, substantially inhibiting differentiation of the stem cells; and (c) transplanting the stem cells to the recipient.

In another particular embodiment of this aspect of the present invention, the method is effected by (a) obtaining hematopoietic stem cells from a recipient; (b) providing the stem cells with ex-vivo culture conditions for cell proliferation and, at the same time, for reducing a capacity of the stem cells in responding to signaling pathways involving the retinoic acid receptor and/or the retinoid X receptor and/or the Vitamin D receptor, thereby expanding a population of the stem cells, while at the same time, substantially inhibiting differentiation of the stem cells; and (c) transplanting the stem cells to the recipient.

In still another particular embodiment of this aspect of the present invention, the method is effected by (a) obtaining hematopoietic stem cells from a recipient; (b) providing the stem cells with ex-vivo culture conditions for cell proliferation and with nicotinamide, a nicotinamide analog, a nicotinamide or a nicotinamide analog derivative or a nicotinamide or a nicotinamide analog metabolite, thereby expanding a population of the stem cells, while at the same time, substantially inhibiting differentiation of the stem cells; and (c) transplanting the stem cells to the recipient.

The effect of the agents that reduce CD38 expression or activity used in context of the present invention is not limited to ex-vivo settings. Hence, based o the findings herein described, novel in-vivo applications for these agents are envisaged.

Hence, according to yet another aspect of the present invention there is provided a method of mobilization of bone marrow stem cells into the peripheral blood of a donor for harvesting the cells. The method according to this aspect of the present invention is effected by (a) administering an effective amount of an agent to the donor for reducing the expression and/or activity of CD38, thereby expanding a population of the stem cells, while at the same time, substantially inhibiting differentiation of the stem cells; and (b) harvesting the cells by leukophoresis.

In a particular embodiment of this aspect of the present invention, the method is effected by (a) administering an effective amount of an agent to the donor for reducing a capacity of the stem cells in responding to retinoic acid, retinoids and/or Vitamin D, thereby expanding a population of the stem cells, while at the same time, substantially inhibiting differentiation of the stem cells; and (b) harvesting the cells by leukophoresis.

In another particular embodiment of this aspect of the present invention, the method is effected by (a) administering an effective amount of an agent to the donor for reducing a capacity of the stem cells in responding to signaling pathways involving the retinoic acid receptor and/or the retinoid X receptor and/or the Vitamin D receptor, thereby expanding a population of the stem cells, while at the same time, substantially inhibiting differentiation of the stem cells; and (b) harvesting the cells by leukophoresis.

In still another particular embodiment of this aspect of the present invention, the method is effected by (a) administering to the donor an effective amount of an agent selected from the group consisting of nicotinamide, a nicotinamide analog, a nicotinamide or a nicotinamide analog derivative and a nicotinamide or a nicotinamide analog metabolite, thereby expanding a population of the stem cells, while at the same time, substantially inhibiting differentiation of the stem cells; and (b) harvesting the cells by leukophoresis.

Preferably, the methods of mobilization of stem cells further comprise administering to the donor at least one cytokine, preferably at least one early cytokine, which are presently used to induce cell mobilization into peripheral blood.

Further according to an aspect of the present invention there is provided a method of decelerating maturation/differentiation of erythroid precursor cells for the treatment of β-hemoglobinopathic patients. The method according to this aspect of the present invention is effected by administering to the patient an agent for reducing the expression and/or activity of CD38, thereby expanding a population of erythroid precursor cells, while at the same time, substantially inhibiting differentiation of the erythroid precursor cells, such that upon natural removal of the agent from the body, the cells undergo accelerated maturation, resulting in elevated production of fetal hemoglobin.

The agent used according to this method of the present invention can be an agent for abrogating or reducing a capacity of the cells in responding to retinoic acid, retinoids and/or Vitamin D, an agent for abrogating or reducing a capacity of the cells in responding to retinoic acid, retinoid X and/or Vitamin D receptor signaling or an agent such as nicotinamide, a nicotinamide analog, a nicotinamide or a nicotinamide analog derivative and a nicotinamide or a nicotinamide analog metabolite.

In in-vivo settings, administration of the agents the reduce CD38 expression or activity, e.g., retinoic acid, retinoid and/or Vitamin D receptor antagonists, or nicotinamide, a nicotinamide analog, a nicotinamide or a nicotinamide analog derivative and/or a nicotinamide or a nicotinamide analog metabolite, may be by a pharmaceutical composition including same, which may further include thickeners, carriers, buffers, diluents, surface active agents, preservatives, and the like, all as well known in the art.

The pharmaceutical composition may be administered in various ways, depending on the preference for local or systemic treatment, and on the area to be treated. Administration may be done topically (including opthalmically, vaginally, rectally, intranasally), orally, by inhalation, or parenterally, for example by intravenous drip or intraperitoneal, subcutaneous, subdural, intramuscular or intravenous injection, or via an implantable delivery device.

Formulations for topical administration may include, but are not limited to, lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include, but are not limited to, sterile solutions, which may also contain buffers, diluents and other suitable additives.

Formulations for implantable delivery devices may similarly include, but are not limited to, sterile solutions, which may also contain buffers, diluents and other suitable additives.

Dosing is dependent on responsiveness of the condition for treatment, but will normally be one or more doses per day, with course of treatment lasting from several days to several months or until a required effect is achieved. Persons ordinarily skilled in the art can easily determine optimum dosages, dosing methodologies and repetition rates. Slow release administration regimes may be advantageous in some applications.

According to preferred embodiments of the present invention, providing the stem cells with the conditions for ex-vivo cell proliferation comprises providing the cells with nutrients and with cytokines. Preferably, the cytokines are early acting cytokines, such as, but not limited to, stem cell factor, FLT3 ligand, interleukin-1, interleukin-2, interleukin-3, interleukin-6, interleukin-10, interleukin-12, tumor necrosis factor-α and thrombopoietin. It will be appreciated in this respect that novel cytokines are continuously discovered, some of which may find uses in the methods of cell expansion of the present invention.

Late acting cytokines can also be used. These include, for example, granulocyte colony stimulating factor, granulocyte/macrophage colony stimulating factor, erythropoietin, FGF, EGF, NGF, VEGF, LIF, Hepatocyte growth factor and macrophage colony stimulating factor.

The stem cells to be expanded by the method of the present invention can be embryonic stem cells or adult stem cells. Embryonic stem cells and methods of their retrieval are well known in the art and are described, for example, in Trounson A O (Reprod Fertil Dev (2001) 13: 523), Roach M L (Methods Mol Biol (2002) 185: 1), and Smith A G (Annu Rev Cell Dev Biol (2001) 17:435). Adult stem cells are stem cells, which are derived from tissues of adults and are also well known in the art. Methods of isolating or enriching for adult stem cells are described in, for example, Miraglia, S. et al. (1997) Blood 90: 5013, Uchida, N. et al. (2000) Proc. Natl. Acad. Sci. USA 97: 14720, Simmons, P. J. et al. (1991) Blood 78: 55, Prockop D J (Cytotherapy (2001) 3: 393), Bohmer R M (Fetal Diagn Ther (2002) 17: 83) and Rowley S D et al (Bone Marrow Transplant (1998) 21: 1253), Stem Cell Biology Daniel R. Marshak (Editor) Richard L. Gardner (Editor), Publisher: Cold Spring Harbor Laboratory Press, (2001) and Hematopoietic Stem Cell Transplantation. Anthony D. Ho (Editor) Richard Champlin (Editor), Publisher: Marcel Dekker (2000).

A presently preferred source for adult stem cells is the hematopoietic system. Hence, according to a preferred embodiment of the present invention the stem cells are hematopoietic stem cells. Such stem cells can be derived from bone marrow, peripheral blood and neonatal umbilical cord blood. Methods of enriching white blood cells (mononuclear cells) for stem cells are well known in the art, including, selecting for $CD34^+$ expressing cells. $CD34^+$ cells include pluripotent stem cells and very early progenitor cells, which, under the appropriate conditions may revert to stem cells, as they are not committed cells.

One most surprising result obtained while reducing the present invention to practice was that stem cells present in the mononuclear cell fraction of blood (i.e., white blood cells), can undergo expansion using the methods of the present invention in a fashion similar to stem cells enriched $CD34^+$ cell fraction of blood. Hence, according to an embodiment of the present invention, the stem cells that undergo expansion are mixed (e.g., not separated from, not enriched) with committed cells. This embodiment of the present invention is of particular advantage because it relieves the tedious need for cell separation prior to ex-vivo culturing the cells.

In another embodiment, the cells are enriched for hematopoietic $CD34^+$ cells and are characterized by an absence, or significantly diminished expression of cell surface antigens CD38 and Lineage specific antigens (Lin, including: CD3, CD61, CD19, CD33, CD14, CD15 and/or CD4).

It was experimentally found that reducing the capacity of the stem cells in responding to the disclosed signaling pathways is reversible, e.g., inherently reversible. In some experiments, following 16-18 weeks in culture the cells ceased to expand and started to differentiate. In other words, cells expanded using the protocols of the present invention to not transform into cell lines. Hence, by exposing such cells following sufficient expansion to growth conditions by which differentiation is induced, one would be able to direct the ex-vivo differentiation of the cells to desired direction, including ex vivo and in vivo cis- and trans-differentiation.

As used herein "cis-differentiation" refers to differentiation of adult stem cells into a tissue from which they were derived. For example, the differentiation of $CD34^+$ hematopoietic cells to different committed/mature blood cells constitutes cis-differentiation.

As used herein "trans-differentiation" refers to differentiation of adult stem cells into a tissue from which they were not derived. For example, the differentiation of $CD34^+$ hematopoietic cells to cells of different tissue origin, e.g., myocites constitutes trans-differentiation.

The stem cells used for cell expansion in context of the present invention can be obtained from any tissue of any multicellular organism including both animals and plants. Stem cells were shown to exist in many organs and tissues and are believed to exist in all tissues of animals, including, but not limited to, bone marrow (Rowley S D et al (1998) Bone Marrow Transplant 21: 1253), peripheral blood (Koizumi K, (2000) Bone Marrow Transplant 26: 787, liver (Petersen B E et al (1998) Hepatology 27: 433) and brain (Pagano S F et al (2000) Stem Cells 18: 295). It is anticipated that all such cells are expandable using the methods of the present invention.

Reducing the capacity of the stem cells in responding to the above antagonists and/or signaling pathways of the above receptors is by ex-vivo culturing the stem cells in a presence of an effective amount of at least one retinoic acid receptor antagonist, at least one retinoid X receptor antagonist and/or at least one Vitamin D receptor antagonist, preferably, for a time period 15 of 0.1-50%, preferably, 0.1-25%, more preferably, 0.1-15%, of an entire ex-vivo culturing period of the stem cells or for the entire period. In this respect it was surprisingly uncovered that an initial pulse exposure to an antagonist is sufficient to exert cell expansion long after the antagonist was removed from the culturing set up.

Many antagonists to RAR, RXR and VDR are presently known, some of which are listed hereinafter.

The retinoic acid receptor antagonist used in context of the different aspects and embodiments of the present invention can be:

AGN 194310; AGN 109; 3-(4-Methoxy-phenylsulfanyl)-3-methyl-butyric acid; 6-Methoxy-2,2-dimethyl-thiochroman-4-one,2,2-Dimethyl-4-oxo-thiochroman-6-yltrifluoromethane-sulfonate; Ethyl 4-((2,2 dimethyl-4-oxo-thiochroman-6-yl)ethynyl)-benzoate; Ethyl 4-((2,2-dimethy 1-4-trifiouromethanensulfonyloxy -(2H)-thiochromen-6-yl) ethynyl)-benzoate(41); Thiochromen-6-yl]-ethynyl]-benzoate(yl); (p-[(E)-2-[3'4'-Dihydro-4,4'-dimethyl-7'-(heptyloxy)-2'H-1-benzothiopyran-6'yl]propenyl]benzoic acid l'1'-dioxide; 2E,4E,6E-[7-(3,5-Di-t-butyl-4-n-butoxyphenyl)-3-methyl]-octa-2,4,6-trienoic acid; 2E,4E,6E-[7-(3,5-Di-t-butyl-4-n-propoxyphenyl)-3-methyl]-octa-2,4,6-trienoic acid; 2E,4E,6E-[7-(3,5-Di-t-butyl-4-n-pentoxyphenyl)-3-methyl]-octa-2,4,6-trienoic acid; 2E,4E,6E-[7-(3,5-Di-t-butyl-4-n-hexoxyphenyl)-3-methyl]-octa-2,4,6-trienoic acid; 2E,4E,6E-[7-(3,5-Di-t-butyl-4-n-heptoxyphenyl)-3-methyl]-octa-2,4,6-trienoic acid; 2E,4E,6E-[7-(3,5-Di-t-butyl-4-n-octoxyphenyl)-3-methyl]-octa-2,4,6-trienoic acid; (2E,4E,6E)-7-[3-t-butyl-5-(1-phenyl-vinyl)-phenyl]-3-methyl-octa-2,4,6-trienoic acid; 2E,4E,6E-[7-(3,5-Di-t-butyl-4-{[4,5-.sup.3H.sub.2]-n-pentoxy}phenyl)-3-methyl]-octa-2,4,6-trienoic acid; (2E,4E)-(1RS,2RS)-5-[2-(3,5-di-tert.butyl-2-ethoxy-phenyl) -cyclopropyl]-3-methyl-penta-2,4-dienoic acid ethyl ester; (2E,4E)-(1RS,2RS)-5-[2-(3,5-di-tert.butyl-2-ethoxy-phenyl)-cyclopropyl]-3-methyl-penta-2,4-dienoic acid; (2E,4E) -(1RS,2RS)-5-[2-(3,5-di-tert.butyl-2-butoxy-phenyl) -cyclopropyl]-3-methyl-penta-2,4-dienoic acid; (2E,4E,6Z)-7-[3,5-di-tert.butyl-2-ethoxyphenyl]3-methyl-2,4,6-octatrienoic acid; (2E,4E,6Z)-7-[3,5-di-tert.butyl-2-butyloxyphenyl]-3-methyl-2,4,6-octatrienoic acid; 4-(5,6,7,8-tetrahydro-5,5,8,8-tetramethyl-2-naphthalene-carboxamido) benzoic acid; (2E,4E)-3-methyl-5-[(1S,2S)-2-(5,5,8,8-tetramethyl-5,6,7,8-tetrahydro-naphthalen-2-yl)-cyclopropyl]-penta-2,4-dienoic acid; p-[(E)-2-[3',4'-Dihydro-4',4'-dimethyl-7'-(heptyloxy)-2'H-1-benzothiopyran-6'-yl]propenyl]benzoic acid; 1',1'-dioxide, 4-(7,7,10,10-Tetramethyl-1-pyridin-3-ylmethyl-4,5,7,8,9,10-hexahydro-1H-naphto[2,3-g]indol-3-yl)-benzoic acid; (2E,4E,6Z)-7-[3,5-di-tert.butyl-2-methoxyphenyl]-3-methyl-2,4,6-octatrienoic acid; (2E,4E,6Z)-7-[3,5-di-tert.butyl-2-ethoxyphenyl]-3-methyl-2,4,6-octatrienoic acid; (2E,4E,6Z) -7-[3,5-di-tert.butyl-2-hexyloxyphenyl]-3-methyl-2,4,6-octatrienoic acid; (2E,4E,6Z)-7-[3,5-di-tert.butyl-2-octyloxyphenyl]-3-methyl-2,4,6-octatrienoic acid; and (2E,4E)-(1RS,2RS)-5-[2-(3,5-di-tert-butyl-2-butoxy-phenyl)-cyclopropyl]-3-methyl-penta-2,4-dienoic acid (2E,4E,6Z)-7-(3-n-propoxy-5,6,7,8-tetramethylnaphthalene-2-yl)-3-methylocta-2,4,6-trienoic acid, and 4-(5H-2,3(2,5 dimethyl-2,5-hexano)-5-n-propyldibenzo[b,e][1,4]diazepin-11-yl)benzoic acid, and 4-(5H-2, 3-(2,5-dimethyl-2,5-hexano)-5methyl-8-nitrodibenzo[b,e][1,4]diazepin-1-yl)benzoic acid, and 4-{[4-(4-Ethylphenyl) 2,2-dimethyl-(2H)-thiochromen-6-yl]ethynyl}benzoic acid, and 4-[4-2methyl-1,2-dicarba-closo-dodecaboran-1-yl-phenylcarbamoyl]benzoic acid, and 4-[4,5,7,8,9,10-hexahydro-7,7,10,10-tetramethyl-1-(3-pyridylmethyl)-anthra[1,2-b] pyrrol-3-yl]benzoic acid, and (3-pyridylmethyl)-]5-thiaanthra[2,1-b]pyrrol-3-yl)benzoic acid, and (3-pyridylmethyl)-anthra[2 ml-d]pyrazol-3-yl]benzoic acid.

The retinoid X receptor antagonist used in context of the different aspects and embodiments of the present invention can be:

LGN100572, 1-(3-hydroxy-5,6,7,8-tetrahydro-5,5,8,8-tetramethylnaphthalene-2-yl)ethanone, 1-(3-propoxy-5,6,7,8-tetrahydro-5,5,8,8-tetramethylnaphthalene-2-yl)ethanone, 3-(3-propoxy-5,6,7,8-tetrahydro-5,5,8,8-tetramethylnaphthalene-2-yl)but-2-enenitrile, 3-(3-propoxy-5,6,7,8-tetrahydro-5,5,8,8-tetramethylnaphthalene-2-yl)but-2-enal, (2E,4E,6E)-7-3[-propoxy-5,6,7,8-tetrahydro 5,5,8,8-tetramethyl-2-naphthalene-2-yl]-3-methylocta-2,4,6-trienoic acid, 4-[3,5,5,8,8-pentamethyl-5,6,7,8-tetrahydro-2-naphthyl)carbonyl] benzoic acid, 4-[1-(3,5,5,8,8-pentamethyl-5,6,7,8-tetrahydro-2-naphthyl)ethenyl]benzoic acid, 4-[1(3,5,5,8,8-pentamethyl-5,6,7,8-tetrahydro-2-naphthyl)cyclopropyl] benzoic acid, 4-[1-(3,5,5,8,8-pentamethyl-5,6,7,8-tetrahydro-2-naphthyl)ethenyl]benzenete trazole, 2-[1-(5,5, 8,8-tetramethyl-5,6,7,8-tetrahydro-2-naphthyl)ethenyl] pyridine-5-carboxylic acid, 2-[1-(3,5,5,8,8-pentamethyl-5,6, 7,8-tetrahydro-2-naphthyl)ethyl]pyridine-5-carboxylic acid, ethyl-2-[1-(3,5,5,8,8-pentamethyl-5,6,7,8-tetrahydro-2-naphthyl)ethenyl]pyridine-5-carboxylate, 5-[1-3,5,5,8,8-pentamethyl-5,6,7,8-tetrahydro-2-naphthyl)ethenyl]pyridine-2-carboxylic acid, 2-[1-(3,5,5,8,8-pentamethyl-5,6,7,8-tetrahydro-2-naphthyl)cyclopropyl]pyridine-5-carboxylic acid, methyl 2-[1-(3,5,5,8,8-pentamethyl-5,6,7,8-tetrahydro-2-naphthyl)cyclopropyl]pyridine-5-carboxylate, 4-[1-(3,5,5, 8,8-pentamethyl-5,6,7,8-tetrahydro-2-naphthyl)ethenyl]-N-(4-hydroxyphenyl) benzamide, 2-[1-(3,5,5,8,8-Pentamethyl-5,6,7,8-tetrahydro-2-naphthyl)ethenyl]pyridine-5-carboxylic acid, 2-[1-(3,5,5,8,8-Pentamethyl-5,6,7,8-tetrahydro-2-naphthyl)cyclopropyl]pyridine-5-carboxylic acid, 4-[(3,5,5,8,8-pentamethyl-5,6,7,8-tetrahydro-2-naphthyl)carbonyl]benzoic acid butyloxime, 4-[(3,5,5,8,8-pentamethyl-5,6,7,8-tetrahydro-2-naphthyl)carbonyl]benzoic acid propyloxime, 4-[(3,5,5,8,8-pentamethyl-5,6,7,8-tetrahydro-2-naphthyl)carbonyl]benzoic acid cyanoimine, 4-[(3,5,5,8,8-pentamethyl-5,6,7,8-tetrahydro-2-naphthyl) carbonyl]benzoic acid allyloxime, 4-[(3,5,5,8,8-pentamethyl-5,6,7,8-tetrahydro-2-naphthyl)carbonyl]benzoic acid 4-(3-methylbut-2-enoic acid)oxime, and 4-[(3,5,5,8,8-pentamethyl-5,6,7,8-tetrahydro-2-naphthyl)carbonyl]benzoic acid 1-aminoethyloxime (2E,4E,6Z)-7-(3-n-propoxy-5,6,7, 8-tetrahydro-5,5,8,8-tetramethylnaphthalene-2-yl)-3-methylocta-2,4,6-trienoic acid, and 4-(5H-2,3(2,5 dimethyl-2,5-hexano)-5-n-propyldibenzo[b,e][1,4]diazepin-11-yl) benzoic acid, and 4-(5H-2,3-(2,5-dimethyl-2,5-hexano)-5m.

The Vitamin D receptor antagonist used in context of the different aspects and embodiments of the present invention can be: 1 alpha, 25-(OH)-D3-26,23 lactone; 1 alpha, 25-dihydroxyvitamin D (3); the 25-carboxylic ester ZK159222; (23S)-25-dehydro-1 alpha-OH-D (3); (23R)-25-dehydro-1 alpha-OH-D (3); 1 beta, 25 (OH)$_2$ D$_3$; 1 beta, 25(OH)$_2$-3-epi-D$_3$; (23S) 25-dehydro-1 alpha(OH) D3-26,23-lactone; (23R) 25-dehydro-1 alpha(OH)D3-26,23-lactone and Butyl-(5Z, 7E,22E-(1S,7E,22E-(1S,3R,24R)-1,3,24-trihydroxy-26,27-cyclo-9,10-secocholesta-5,7,10(19),22-tetraene-25-carboxylate).

The above listed antagonists are known for their high affinity towards their respective cognate receptors. However, it may be possible for these molecules to be active towards other receptors.

According to an additional aspect of the present invention, there is provided an assay of determining whether a specific retinoic acid receptor antagonist, a retinoid X receptor antagonist or a Vitamin D receptor antagonist is an effective cell expansion agent. The assay according to this aspect of the present invention comprises culturing a population of stem cells, e.g., CD34+ hematopoietic cells, or cells of a substantially non-differentiated cell line, such as, but not limited to, USP-1 and USP-3 (Sukoyan M A (2002) Braz J Med Biol Res, 35(5):535, C6, c2, Cr/A-3, DB1 and B6-26 (U.S. Pat. No. 6,190,910), and H9.1 and H9.2 (Odorico J. S. (2001) Stem Cells 19: 193) in the presence of the retinoic acid receptor antagonist, the retinoid X receptor antagonist or the Vitamin D receptor antagonist and monitoring expansion of the cells over time, e.g., a few weeks to a few months. If increased expansion and decreased differentiation occurs, as compared to non-treated cells, the retinoic acid receptor antagonist, the retinoid X receptor antagonist or the Vitamin D receptor antagonist tested is an effective cell expansion agent. Preferably, culturing the population of stem cells or cells of a substantially non-differentiated cell line is performed in a presence of an effective amount of a cytokine, preferably, an early acting cytokine or a combination of such cytokines, e.g., thrombopoietin (TPO), interleukin-6 (IL-6), an FLT-3 ligand and stem cell factor (SCF). This assay can be used, by one ordinarily skilled in the art, to determine which of the antagonists listed below is most efficient for the purpose of implementing the various methods, preparations and articles-of-manufacture of the present invention which are further described hereinafter. To determine most effective concentrations and exposure time for achieving optimal results with stem cells of different origins.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following.

EXAMPLES

Reference is now made to the following examples, which together with the above descriptions illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

RAR-Antagonists and Their Use in Ex-Vivo Hema Topoietic Cell Expansion

Material and Experimental Methods

High-Affinity Retinoic Acid Receptor Antagonist (RAR) Synthesis:

Synthesis of the RAR Antagonist 4-[[4-(4-ethylphenyl)-2,2-dimethyl-(2H)-thiochomen-6-yl)]-benzoic acid, (A GN 194310):

The RAR antagonist AGN194310 was synthesized according to the procedure described by Johnson (26), with some modification.

Synthesis of 3-(4-methoxyphenylthio)-3-methyl-butyric acid:

A heavy-walled screw-cap tube was charged with 3-methyl-2-butenoic acid (13.86 gm) 3,3-dimethylacrylic acid, (138.4 mmol), 4-methoxythiophenol (143.2 mmol), and piperidine (41.6 mmol) [Aldrich]. The mixture was heated to 105-110° C. for 32 hours, then cooled to room temperature. The reaction mixture was dissolved in ethyl acetate (EtOAc) (700 ml) with stirring, and the resulting solution was washed with 1M aqueous HCl (50 ml×2), water (50 ml), and saturated aqueous NaCl (50 ml). The organic solution was thereafter dried over $NaSO_4$. Concentration of this organic solution under reduced pressure afforded an oil and 2 days incubation at −20° C. yielded a crystalline solid. Forty ml of pentane were added to the solid, which was then crushed and filtered. The solid was washed on filter paper with pentane (20 ml, 2 times) to yield the product 3-(4-methoxyphenylthio)-3-methyl-butyric acid, as pale yellow crystals (31.4 grams, 94.4% yield, m.p. 62-64° C.), [$^1$H-NMR($CDCl_3$): d7.5 (t, 2H, J=8 Hz), d6.9 (t, 2H, J=6.7 Hz), d3.9 (s, 3H, J=16.1 Hz), d2.6 (s, 2H), d1.3 (s, 6H)].

Synthesis of 3-(4-methoxyphenylthio)-3-methyl-butyryl chloride:

93.62 mmol oxalyl chloride in 10 ml benzene was added to a solution of 3-(4-methoxyphenylthio)-3-methyl-butyric acid in 100 ml of benzene at room temperature, for 30 minutes. During the addition of the oxalyl chloride, the solution turned yellow. After stirring the reaction mixture for 4 hours at room temperature, the reaction solution was cooled to 5° C. and washed with ice cold 5% aqueous NaOH (5 ml×6) (a large volume of gas was released during this procedure), followed by ice-cold water (15 ml×2) and finally saturated aqueous NaCl (15 ml). The organic solution was dried over $NaSO_4$ and concentrated under reduced pressure to give the acyl chloride product as a clear yellow oil. This material was used without further purification in the next step. [$^1$H-NMR (CDCl$_3$): d3.8 (s, 3H), d3.1 (s, 2H), d1.4 (s, 6H)].

Synthesis of 6-methoxy-2,2-dimethyl-thiochroman-4-one:

A solution of Tin (IV) chloride in 30 ml dichloromethane was added dropwise to a solution of 3-(4-methoxyphenylthio)-3-methyl-butyryl chloride in 180 ml dichloromethane, at 0° C., yielding a dark red solution. After stirring the reaction mixture at 0° C. for 2 hours, the reaction was quenched by the slow addition of 115 ml water. The dark red reaction mixture became yellow.

The organic layer was washed with 1M aqueous HCl (50 ml), 5% aqueous NaOH (50 ml) and a saturated solution of NaCl (50 ml) and was thereafter dried over magnesium sulfate. The resulting organic solution was concentrated under reduced pressure, and distilled under vacuum (135-142° C., 0.6 mm/Hg) to obtain 6-methoxy-2,2-dimethyl-thiochroman-4-one as a residual pale-yellow oil (11 grams, 80.7%); [$^1$H-NMR (CDCl$_3$): d7.6 (s, 1H), d7.1 (s, 1H), d7.0 (s, 1H), d3.8 (s, 3H), d2.86 (s, 2H), d1.46 (s, 6H)].

Synthesis of 6-hydroxy-2,2-dimethyl-thiochroman-4-one:

Boron tribromide (20 grams) in 80 ml dichloromethane was added over a 20 minute period to a solution of 6-methoxy-2,2-dimethyl-thiochroman-4-one in 50 ml dichloromethane. The reaction mixture was cooled to −23° C. and stirred for 5 hours, cooled to −78° C., then quenched by the slow addition of 50 ml water (0.5 hour). Following warming to room temperature, the colorless precipitate was filtered. After separation of the organic layer, the aqueous layer was extracted with 120 ml dichloromethane. The combined organic layers were washed with saturated aqueous NaHCO$_3$ (50 ml), water (50 ml) and saturated aqueous NaCl, then dried over MgSO$_4$. Removal of the organic solvent under reduced pressure gave a green solid (6 grams of crude product). This product was dissolved in 100 ml diethyl ether and the resulting solution was diluted with 300 ml petroleum ether. Overnight incubation at −15° C. yielded a crystalline product (2.3 grams, 41% yield, m.p. 122-126° C.). The filtrate was evaporated under vacuum, and the residue (3.42 grams) was dissolved in 30 ml diethyl ether. The ether solution was diluted with 150 ml petroleum ether and the resulting mixture was kept in a freezer at −20° C. overnight. Precipitation and filtration of the product yielded 1.5 grams of the product 6-methoxy-2,2-dimethyl-thiochroman-4-one. This compound was re-precipitated by dissolution in 30 ml diethyl ether, then diluted with 20 ml petroleum ether. Incubation at 4° C. overnight, yielded 1 gram (80.7% yield, m.p. 135-142° C., 0.6 mm/Hg) of the green crystalline product, 6-hydroxy-2,2-dimethyl-thiochroman-4-one. [$^1$H-NMR (CDCl$_3$): d7.8 (s, 1H), d7.7 (s, 1H), d7.1 (s, 1H), d2.8 (s, 2H), d1.45 (s, 6H)].

Synthesis of 2,2-dimethyl-4-oxo-thiochroman-6-yl-trifluoro-methanesulfonate:

Trifluoromethanesulfonic anhydride was added to a stirred solution of 6-hydroxy-2,2-dimethyl-thiochroman-4-one in anhydrous pyridine. The mixture was stirred for 4 hours at 0° C., then stirred overnight at room temperature. Concentration under high vacuum yielded a residue that was treated with diethyl ether (75 ml). The ether solution was separated from the precipitate resulting from the formation of a salt between pyridine and trifluoromethanesulfonic acid. The ether solution was washed with water, then aqueous NaCl, and dried over MgSO$_4$. After removing the ether, the residue was crystallized. Traces of pyridine were removed under high vacuum. 0.7 gram of the crude product was obtained, and was further purified by column chromatography using 14 grams silica, and a solution of 200 ml petroleum ether:ethyl acetate (95:5) (using 15 ml eluent solution×13). After evaporation of the product fractions, 0.62 gram of 2,2-dimethyl-4-oxo-thiochroman-6-yl-trifluoro-methanesulfonate was obtained as colorless crystals (76.5% yield, m.p. 70-74° C.), [$^1$H-NMR (CDCl$_3$): d7.9 (s, 1H), d7.3 (s, 2H), d2.8 (s, 2H), d1.4 (s, 6H)].

Synthesis of 2,2-dimethyl-6-trimethylsilanyl-ethynyl-thiochroman-4-one:

A solution of 2,2-dimethyl-4-oxo-thiochroman-6-yl-trifluoro-methanesulfonate in triethylamine and dimethylformamide was sparged with argon for 10 minutes. Trimethylsilylacetylene and bis[triphenylphosphine]palladium(II) chloride were added to this solution. The reaction mixture was heated in a bath at 95-100° C. and maintained a reaction temperature of 88-90° C., for 5 hours. The reaction solution was cooled to room temperature, diluted with 200 ml water, and extracted with 100 ml ethyl acetate (60 ml×3). The resulting organic phase was washed with water (50 ml×2), and brine (50 ml). Finally, the organic solution was dried over MgSO$_4$, evaporated under reduced pressure, and the resulting residue was further purified by column chromatography using 42 grams silica, and an eluent system composed of 400 ml petroleum ether:ethyl acetate (97:3), yielding 2,2-dimethyl-6-trimethylsilanyl-ethynyl-thiochroman-4-one (1.82 grams, 76.4% yield, m.p. 67-70° C.); [$^1$H-NMR (CDCl$_3$): d7.8 (s, 1H), d7.3 (s, 2H), d2.8 (s, 2H), d1.4 (s, 6H), d0.23 (s, 9H)].

Synthesis of 6-ethynyl-2,2,-dimethylthiochroman-4-one:

A solution of 2,2-dimethyl-6-trimethylsilanyl-ethynyl-thiochroman-4-one in methanol and potassium bicarbonate was stirred overnight at room temperature. The potassium carbonate was dissolved and the reaction was evaporated to a reduced volume of 30-40 ml, diluted with water (to an approximate volume of 70-100 ml), cooled in an ice-water bath and extracted with diethyl ether (60 ml×3). The combined organic layers were washed with 30 ml water and saturated aqueous NaCl (30 ml) and dried over MgSO$_4$. Removal of the solvent under reduced pressure afforded 6-ethynyl-2,2-dimethylthiochroman-4-one as an orange solid (1.3 gram, 97.7% yield, m.p. 63-66° C.) [$^1$H-NMR (CDCl$_3$): d7.8 (s, 1H), d7.3 (s, 2H), d3.0 (s, 1H), d 2.8 (s, 2H), d1.4 (s, 6H)].

Synthesis of ethyl 4-iodobenzoate:

A mixture of 4-iodobenzoic acid, 25 ml ethyl alcohol and 20 ml solution of dry HCl in ethyl alcohol was refluxed for 2 hours. The solid was dissolved after 1 hour of boiling. The reaction solution was cooled to room temperature and evaporated under vacuum to a volume of 10 ml. A lower organic layer formed with the chemical conversion of the acid to the ester. The resulting mixture was cooled in an ice bath. To this mixture 80 ml of diethyl ether, dry sodium hydrogen carbonate (1 gram) and 50 grams of ice were added. This solution was stirred, washed by dissolution of a saturated solution of sodium bicarbonate in 50 ml water and water, dried over sodium sulfate, and evaporated under vacuum, yielding ethyl 4-iodobenzoate as a liquid oil product (5.43 gram, 96.1% yield) [$^1$H-NMR (CDCl$_3$): d7.8 (s, 1H), d7.79 (s, 1H), 7.6 (s, 1H), d4.4 (d, 2H, J=7.1 Hz), d1.4 (s, 3H)].

Synthesis of ethyl 4-[(2,2-dimethyl-4-oxo-thiochroman-6-yl)ethynyl]-benzoate:

A solution of 6-ethynyl-2,2-dimethyl-thiochroman-4-one and ethyl 4-iodobenzoate in 80 ml triethylamine was purged with argon for 10 minutes. 0.7 gram Pd[PPh$_3$]$_2$Cl$_2$ and 0.19 gram CuI were added to this solution. The solution was sparged with argon for an additional 5 minutes, then stirred for 2 days at room temperature. The reaction mixture was filtered through a pad of celite with a diethyl ether wash. The filtrate was evaporated under reduced pressure. The solid residue was purified by column chromatography (40 grams silica, petroleum ether:ethyl acetate 95:5, 750 ml eluent solvent system) to yield ethyl 4-[(2,2-dimethyl-4-oxo-thiochroman-6-yl)ethynyl]-benzoate (1.26 gram, 56.5% yield, m.p. 102-104° C.). [$^1$H-NMR(CDCl$_3$): d8.275 (s, 2H), d7.6 (s, 3H), d7.5 (s, 1H), d7.2 (s, 1H), d4.3 (t, 2H, J=7), d2.8 (s, 2H), d1.48 (s, 3H)].

Synthesis of Ethyl 4-[(2,2-dimethyl-4-trifluoromethanesulfonyloxy)-(2H)-thiochromen-6-yl)ethynyl]benzoate:

A solution of sodium bis(trimethylsilyl)amide (0.6 M solution in toluene) and 10 ml of tetrahydrofuran was cooled to −78° C. and a solution of ethyl 4-[(2,2-Dimethyl-4-oxo-thiochroman-6-yl)ethynyl]benzoate in 10 ml tetrahydrofuran (THF) was slowly added. After 30 minutes, a solution of 2-[N,N-bis(trifluoromethanesulfonyl)amino]pyridine in 7 ml THF was added to the reaction mixture. After 5 minutes, the cooling bath was removed and the reaction solution was warmed to room temperature, stirred overnight and quenched by the addition of a saturated aqueous solution of NH$_4$Cl (20 ml). Two solvent layers were formed. The solution mixture was extracted with ethyl acetate (75 ml). The combined organic layers were washed with 5% aqueous NaOH (10 ml), water (15 ml×2), dried over MgSO$_4$, then concentrated under reduced pressure. The crude product (1.74 gram) was purified by column chromatography with 35 grams silica, and 2% ethyl acetate/petroleum ether (500 ml, 20×25 ml) eluent system. After evaporation of the combined eluted product fractions, ethyl 4-[(2,2-dimethyl-4-trifluoromethanesulfonyloxy)-(2H)-thiochromen-6-yl)ethynyl]benzoate (1.16 gram, 71% yield, m.p. 100-104° C.) was obtained, as a pale yellow solid. [$^1$H-NMR (CDCl$_3$): d8.2 (s, 2H), d7.6 (s, 3H), d7.5 (s, 1H), d7.2 (s, 1H), d6.0 (s, 1H), d4.4 (t, 6H, J=24 Hz)].

Synthesis of ethyl 4-[[4-(4-ethylphenyl)-2,2-dimethyl-[2H]-thiochromen-6-yl]-ethynyl]-benzoate:

7.25 ml of 1.7 M LiC(CH$_3$)$_3$ in pentane were added to a solution of p-bromo-ethyl-benzene (cooled to −78° C.) in 4 ml of THF. A solution of 658.7 mg zinc chloride in 8 ml THF was added, and the reaction mixture was warmed to room temperature, stirred for 40 minutes, then transferred to a second flask containing ethyl 4-[(2,2-Dimethyl-4-trifluoromethylsulfonyl)-(2H) -thiochromen-6-yl)ethynyl]benzoate and Pd(PPh$_3$)$_4$ in 8 ml THF. The resulting solution was heated to 50° C. for 2 hours, stirred at room temperature overnight, then quenched by addition of saturated aqueous NH$_4$Cl (10 ml) for 10 minutes. Two layers formed. The mixture was extracted with 75 ml ethyl acetate and the combined organic layers were washed with water (10 ml), and saturated NaCl. After drying the organic solution over MgSO$_4$, the solution was concentrated under reduced pressure, and purified by column chromatography using 24 grams silica, and a petroleum ether:ethyl acetate (95:5) eluent system (200 ml) yielding ethyl 4-[[4-(4-ethylphenyl)-2,2-dimethyl-[2H]-thiochromen-6-yl]-ethynyl]-benzoate

[$^1$H-NMR (CDCl$_3$): d8.2 (s, 2H), d7.6 (s, 2H), d7.4 (s, 2H), d7.2 (s, 1H), d7.1 (s, 2H), d7.0 (s, 2H), d6.0 (s, 1H), d4.4 (t, 2H, J=24 Hz), d2.8 (t, 2H, J=15 Hz), d1.6 (s, 6H), d1.4 (t, 3H, J=14 Hz)].

Synthesis of 4-[14-(4-Ethylphenyl)-2,2-dimethyl-(2H)-thiochroman-6-yl]-ethynyl]benzoic acid:

Two ml of a 2 M solution of NaOH were added to a solution of ethyl 4[[4-(4-ethylphenyl)-2,2-dimethyl-[2H]-thiochromen-6-yl]-ethynyl]benzoate in THF and ethanol. The solution was heated to 40° C., stirred overnight, then cooled to room temperature. The reaction mixture was acidified with 1 N HCl (4 ml). At the beginning of the process, the reaction mixture formed a heterogeneous system. The mixture was extracted with ethyl acetate (25 ml×2). The combined organic layers were washed with 10 ml water, saturated aqueous NaCl, and dried with NaSO$_4$, and the solvent was removed under reduced pressure. The residual solid (0.31 gram) was recrystallized from acetonitrile (25 ml) to yield 4-[[4-(4-ethylphenyl)-2,2-dimethyl-(2H)-thiochroman-6-yl]-ethynyl] benzoic acid, (AGN194310) (0.236 gram, 70%) as a colorless solid (m.p. 210-212° C.) [$^1$H-NMR (DMSO-d6): d8.2 (s, 2H), d7.8 (s, 2H), d7.6 (s, 2H), d7.4 (s, 2H), d7.2 (s, 2H), d7.0 (s, 1H), d6.0 (s, 1H), d2.6 (t, 2H, J=35 Hz), d1.6 (s, 6H), d1.4 (t, 3H, J=46 Hz)].

Mononuclear Cell Fraction Collection and Purification:

Human blood cells were obtained from umbilical cord blood from female patients following full-term, normal delivery (informed consent was obtained).

Samples were collected and processed within 12 hours postpartum. Blood was mixed with 3% Gelatin (Sigma, St. Louis, Mo.), sedimented for 30 minutes to remove most red blood cells. The leukocyte-rich fraction was harvested and layered on a Ficoll-Hypaque gradient (1.077 gram/ml; Sigma), and centrifuged at 400 g for 30 minutes. The mononuclear cell fraction in the interface layer was collected, washed three times and resuspended in phosphate-buffered saline (PBS) solution (Biological Industries) containing 0.5% bovine serum albumin (BSA, Fraction V; Sigma).

Purification of CD34$^+$ Cells From Mononuclear Cell Fractions:

To purify CD34$^+$ mononuclear cells, the fraction was subjected to two cycles of immuno-magnetic separation using the MiniMACS® or Clinimax® CD34 Progenitor Cell Isolation Kit (Miltenyi Biotec, Auburn, Calif.) as per manufacturer's recommendations. The purity of the CD34$^+$ population obtained ranged from 95% to 98% as was determined by flow cytometry (see below).

To further purify the CD34$^+$ population into CD34$^+$38$^-$ or the CD34$^+$Lin$^-$ sub-fractions, the purified CD34$^+$ cells were further labeled for CD38 (Dako A/S, Glostrup, Denmark) or lineage antigens (BD Biosciences, Erermbodegem, Belgium). The negatively labeled fraction was measured and sorted by a FACS sorter.

For CD34$^-$Lin$^-$ purification, the CD34$^-$ fraction was depleted from cells expressing lineage antigens using a negative selection column (StemCell Technologies, Vancouver, BC, Canada).

Ex-Vivo Expansion of CD34$^{+/-}$ Cell Populations:

CD34$^+$ expressing purified cells above were cultured in 24-well Costar Cell Culture Clusters (Corning Inc., Corning, N.Y.) or culture bags (American Fluoroseal Corp), at a concentration of 10$^4$ cells/ml in alpha medium (Biological Industries, Beit Haemek, Israel) supplemented with 10% fetal bovine serum (FBS, Biological Industries). The following human recombinant cytokines were added: Thrombopoietin (TPO), interleukin-6 (IL-6), FLT-3 ligand and stem cell factor (SCF), all at final concentrations of 50 ng/ml each, though occasionally IL-3, at a concentration of 20 ng/ml, was added either together or instead of SCF. For non-hematopoietic cell differentiation, FGF, EGF, NGF, VEGF, LIF or Hepatocyte growth factor (HGF) were used to supplement the growth medium, either alone or in various combinations. All cytokines used were purchased from Perpo Tech, Inc. (Rocky Hill, N.J.). The cultures were incubated at 37° C., 5% CO$_2$, in a humidified atmosphere.

Alternatively, whole mononuclear fraction cells (MNC) were isolated, cultured and supplemented with cytokines, as above.

At weekly intervals, cell cultures were toped and semi-depopulated and were supplemented with fresh medium, serum and cytokines or supplemented with fresh growth medium, alone. At predetermined time points, cells were harvested, stained with trypan blue, counted, and cell morphology was determined via the use of cytospin (Shandon, UK)-prepared smears stained with May-Grunwald/Giemsa solutions.

RAR Antagonist Supplementation of Ex-Vivo Hematopoietic Stem/Progenitor Cell Cultures:

CD34$^+$ purified and whole MNC cultures were prepared and maintained as described above. AGN 194310 RAR antagonist was added to test cultures at concentrations ranging from $1\times10^{-3}$-$1\times10^{-11}$ M [or 410 µg/l to $4.1\times10^{-5}$ µg/l]. The antagonist was added for a predetermined, limited period, for up to three weeks or continuously during the entire culture period.

Morphological Assessment:

Morphological characterization of the resulting culture populations was accomplished on aliquots of cells deposited on glass slides via cytospin (Cytocentrifuge, Shandon, Runcorn, UK). Cells were fixed, stained with May-Grunwald/Giemsa stain and examined microscopically.

Surface Antigen Analysis:

Cells were harvested, washed with a PBS solution containing 1% bovine sera albumin (BSA) and 0.1% sodium azide (Sigma), and stained at 4° C. for 60 minutes with fluorescein isothiocyanate or phycoerythrin-conjugated antibodies (all from Immunoquality Products, the Netherlands). The cells were then washed with the same buffer and analyzed by FACS caliber or Facstarplus flow cytometers. Cells were passed at a rate of 1000 cells/second, using saline as the sheath fluid. A 488 nm argon laser beam served as the light source for excitation. Emission of ten thousand cells was measured using logarithmic amplification, and analyzed using CellQuest software. Negative control staining of cells was accomplished with mouse IgG-PE (Dako A/S Glostrup, Denmark) and mouse IgG-FITC (BD Biosciences, Erembodegem, Belgium).

Determination of CD34 and Other Hematopoietic Marker Expression:

CD34 surface expression on short and long-term cultures initiated either with purified CD34$^+$ cells or the entire MNC fraction was determined as follows: CD34$^+$ cells were positively reselected (Miltenyi kit) and counted. Purity was confirmed by subsequent FACS and cell morphology analysis.

Reselected CD34$^+$ cell subsets were stained for the following combination of antigens: CD34PE/CD38FITC and CD34PE/38, 33, 14, 15, 3, 4, 61, 19 (Lin) FITC. The fraction positive for CD34 and negative for CD38 was defined as CD34$^+$CD38$^-$. The fraction positive for CD34 and negative for LIN was defined as CD34$^+$Lin$^-$ cell fraction.

Cell Population Calculations:

FACS analysis results are given as percentage values of cells. Absolute numbers of subsets are calculated from the absolute number of CD34$^+$ cells.

Determination of baseline levels of CD34$^+$/CD38$^-$ and CD34$^+$/Lin$^-$ cells was conducted as follows: CD34$^+$ cells were purified from 3 thawed cord blood units and stained for the above markers. The mean of these experiments was considered as the baseline value.

Total cell counts, numbers of CD34$^+$ cells and subsets, and CFU numbers are presented as cumulative numbers, with the assumption that the cultures had not been passaged; i.e., the number of cells per ml were multiplied by the number of passages performed.

Assaying Colony Forming Unit (CFU) Ability:

Cells were cloned in semi-solid, methylcellulose-containing medium supplemented with 2 IU/ml erythropoietin (Eprex, Cilag AG Int., Switzerland), stem cell factor and IL-3, both at 20 ng/ml, and G-CSF and GM-CSF, both at 10 ng/ml (all from Perpo Tech). Cultures were incubated for 14 days at 37° C., 5% $CO_2$ in a humidified atmosphere.

Determination of LTC-CFUc Values:

Briefly, the ability of the cultures to maintain self-renewal was measured by determination of the content of colony forming unit cells in the long and extended long-term cultures (LTC-CFUc), as described in the references hereinabove.

Experimental Results

RAR Antagonist Treatment of Enriched CD34$^+$ Populations Alters Surface Differentiation Marker Expression Resulting in Large Numbers of Cells With a Less-Differentiated Phenotype in Short-Term Cultures:

In order to determine retinoid receptor antagonist effects on the ex-vivo expansion of stem cells, CD34$^+$ cell enriched cultures were initiated in the presence of a combination of 4 cytokines with and without different concentrations of the retinoic acid receptor antagonist AGN 194310. Two weeks after the initial seeding, the percentage of cells bearing the CD34$^+$ marker (considered to be mostly committed progenitor cells), as well as the percentage of cells bearing the markers CD34$^+$/CD38$^-$ and CD34$^+$Lin$^-$ (considered to represent the stem and early progenitor compartment) was ascertained by FACS analysis.

Figure 1C:
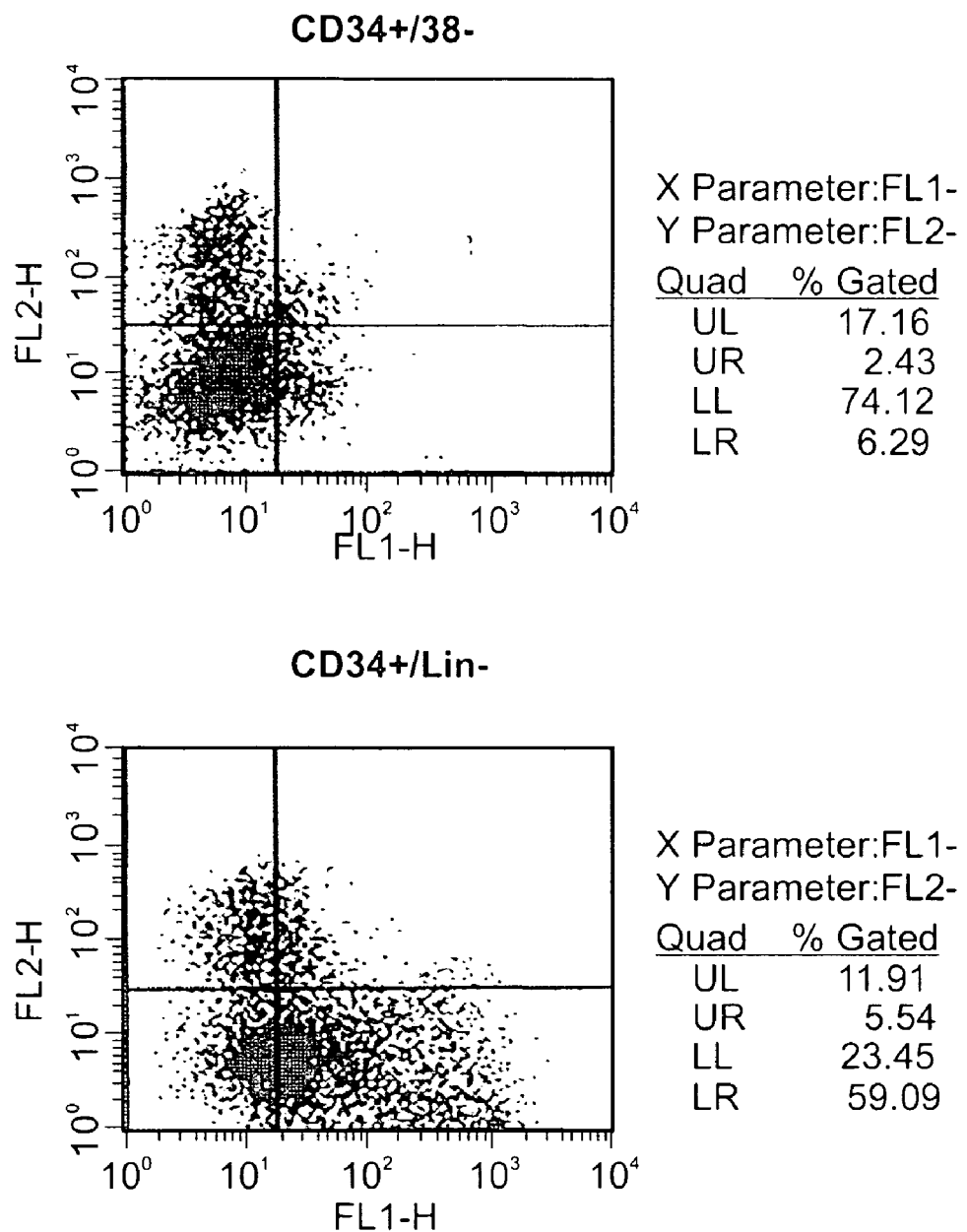
FIG. 1C is a FACS analysis plot showing RAR antagonist ($10^{-6}$ M) treated culture cell surface marker expression with a similar level of expression of the CD34 antigen, but an almost complete abrogation of the CD38 and lineage-related antigen expression, as compared to controls.

The FACS analysis plots are shown in FIGS. 1A-C. Retinoic acid receptor (RAR) antagonist treated cultures contained similar numbers of total and CD34$^+$ cells as compared to cytokine-only treated cultures. RAR antagonist treatment completely abolished the expression of the CD38 antigen and concurrently, significantly inhibited the expression of the additional differentiation associated antigens CD33, CD14, CD15, CD4, CD3, CD19 and CD61, which was a totally unexpected phenomenon. Table 1 below summarizes the data from the FACS analysis.

TABLE 1

| | No. of cells ($\times10^4$) | % 34$^+$ cells | % 34$^+$/38$^-$ cells | % 34$^+$/Lin$^-$ cells |
|---|---|---|---|---|
| control (cytokines only) | 52 | 19.41 | 6.82 | 3.96 |
| RAR antagonist, $10^{-5}$ M | 42 | 18.94 | 17.14 | 15.18 |
| RAR antagonist, $10^{-6}$ M | 52 | 19.59 | 17.16 | 11.91 |

Figure 2A:
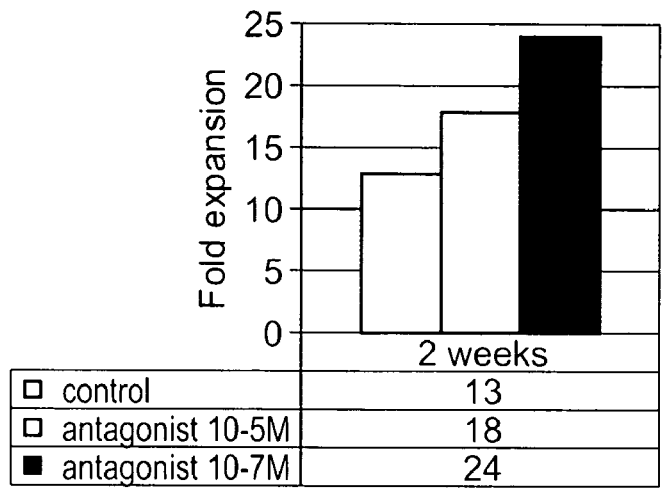
FIG. 2A is a graph of data collected by FACS analysis showing comparable CD34$^+$ cell expansion levels in control and RAR antagonist treated cultures.
Figure 2B:
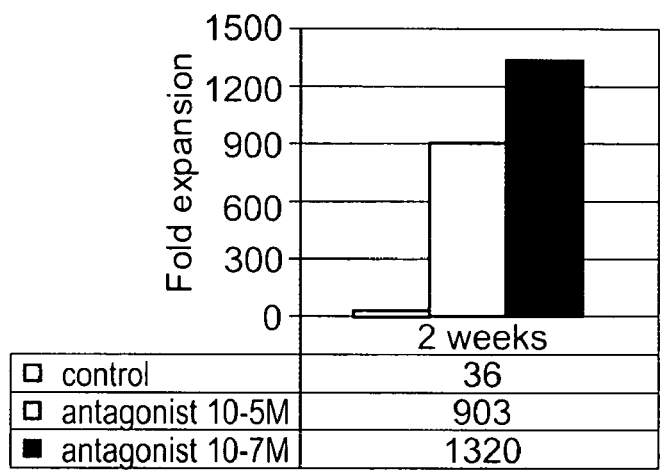
FIG. 2B is a graph of data collected by FACS analysis showing markedly enhanced CD34$^+$CD38$^-$ cell expansion levels in response to RAR antagonist treatment, at either the $10^{-5}$ or $10^{-7}$ M concentrations, as compared to controls.
Figure 2C:
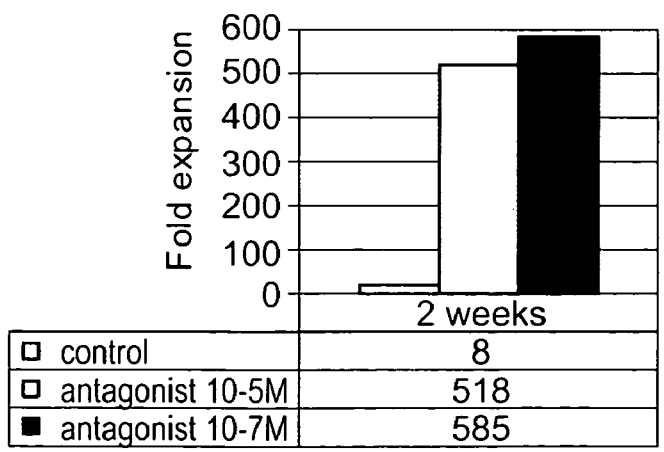
FIG. 2C is a graph of data collected by FACS analysis showing markedly enhanced CD34$^+$Lin$^-$ cell expansion levels in response to RAR antagonist treatment, at either the $10^{-5}$ or $10^{-7}$ M concentrations, as compared to controls.

In an additional set of experiments, the stem and early progenitor cell subsets were measured following 2 weeks expansion from a re-selected CD34$^+$ cell fraction. After two weeks in culture, CD34$^+$ cells were re-selected and analyzed by FACS, as above, for the presence of the surface markers CD34$^+$CD38$^-$ and CD34$^+$Lin$^-$ (FIG. 2). RAR antagonist-treated cultures of reselected CD34$^+$ cells revealed a 1000-fold increase in CD34$^+$CD38$^-$ and a 500-fold increase in CD34$^+$Lin$^-$ surface expression. In marked contrast, reselected control cultures treated with cytokines alone revealed only a 36-fold expansion of the CD34$^+$CD38$^-$ and an 8-fold expansion of the CD34$^+$Lin$^-$ compartments. Despite the marked differences in surface antigen expression, the total number of cells, and total number of CD34$^+$ cells was comparable in all cultures. These results indicate that RAR antagonists preferably enable marked proliferation, yet limited differentiation of the stem cell compartment. RAR antagonists thus directly impact the high fold expansion of these rare cells during the short-term culture period. It could also be concluded that the antagonists do not have any positive or negative effect on more mature, committed CD34+ cells.

Figure 3A:
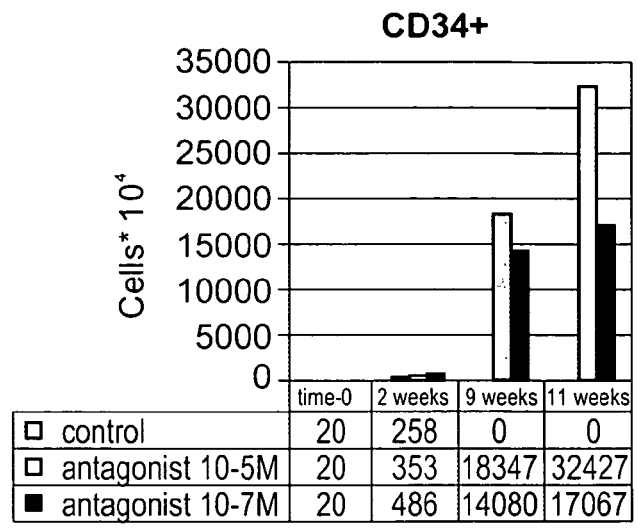
FIG. 3A is a graph of data collected by FACS analysis revealing comparable CD34$^+$ surface expression up to 2 weeks post seeding of control and treated cultures. Cultures were treated with an RAR antagonist, $10^{-5}$ M and $10^{-7}$ M [or 41 µg/liter to 0.41 µg/liter) and a combination of 4 cytokines (IL-6, TPO, FLT3 and SCF), and were subjected to an additional positive selection step prior to FACS analysis. A marked increase in expression is seen, however, 9 and 11 weeks post seeding in cultures treated with RAR antagonists, as compared to controls.

RAR Antagonist Treatment of Enriched CD34+ Populations Alters Surface Differentiation Marker Expression Resulting in Large Numbers of Cells With a Less-Differentiated Phenotype in Long-Term Cultures:

In order to find out whether the RAR antagonists potentiate a stem cell fraction with higher self-renewal ability, the effect of a limited, short-term (2-3 weeks) RAR antagonist culture treatment was tested on long-term expansion of CD34+ cells and subsets. Cultures were treated with RAR antagonists for the first three weeks only and then incubated for an additional eight weeks in the absence of the antagonist. In order to determine the effect of the antagonist on short and long term expansion of CD34+ cells, representative samples were taken from the cultures at the time intervals indicated (FIG. 3), for re-selection of CD34+ cells. CD34+ surface expression was again determined by FACS analysis following a positive selection step (FIG. 5B). During the first three weeks of incubation there were no significant differences between control and RAR antagonist treated cultures in terms of the numbers of CD34+-bearing cells. Following an additional eight weeks of incubation (week 11 of the culture), the RAR antagonist pre-treated cultures revealed a continuous, long-term increased expression of surface CD34+ antigen (FIG. 3A) whereas no CD34+ cells could be detected in the control cultures. A 92-fold increase in expression was seen in RAR antagonist treated cultures between week three to eleven and a 1621-fold expansion of this compartment occurred since the initiation of the cultures.

Figure 3B:
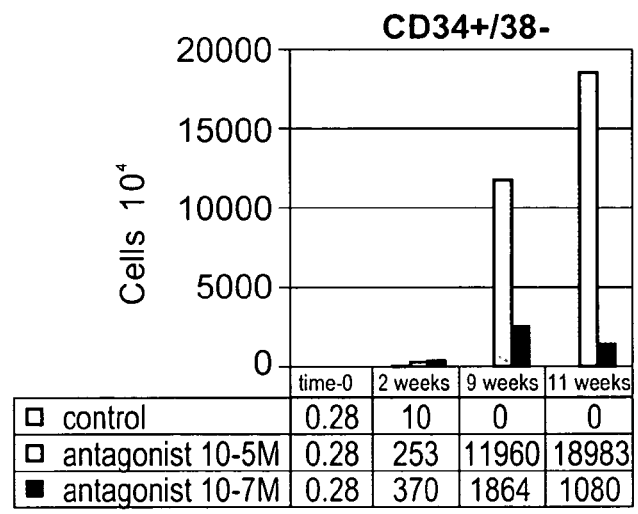
FIG. 3B is a graph of data collected by FACS analysis showing comparable CD34$^+$CD38$^-$ surface expression up to 2 weeks post seeding of control and RAR antagonist and cytokine treated cultures, (as treated in 3A), in samples subjected to an additional positive selection step. A marked increase in expression is seen 9 and 11 weeks post seeding in RAR antagonist treated cultures, as compared to controls.
Figure 3C:
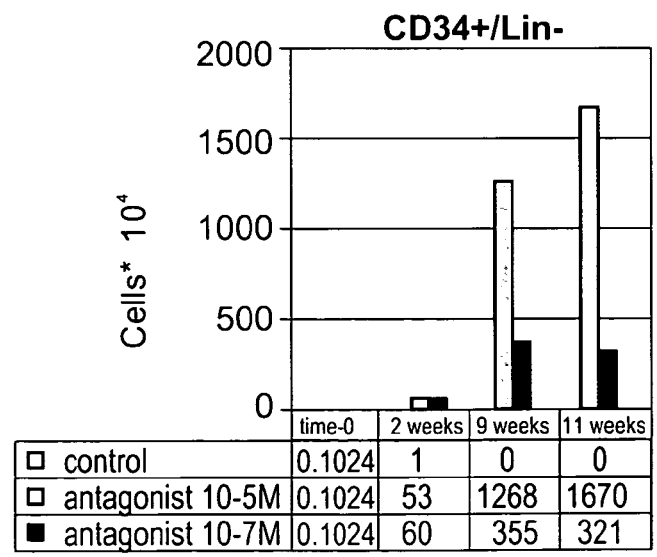
FIG. 3C is a graph of data collected by FACS analysis showing enhanced CD34$^+$Lin$^-$ surface expression by 2 weeks post seeding of RAR antagonist treated cultures, (as treated in 3A), as compared to controls, in samples subjected to an additional positive selection step. A markedly increased expression is seen in the groups treated with RAR antagonist by 9 and 11 weeks post seeding.

Expression of the CD34+CD38− and CD34+Lin− surface markers was verified in a highly purified, CD34+ re-selected fraction (FIG. 3B-C). After two weeks in culture, while control samples revealed a modest 10-fold increase in CD34+Lin− surface expression, RAR antagonist treated cultures expanded by a marked 530-fold. CD34+Lin− expression at week eleven, 9 weeks after the termination of the treatment with the antagonist, revealed a 16,700-fold increase in CD34+Lin− expression. Comparison between the fold-expansion of RAR antagonist treated cultures versus that of control cells indicates that only the former enables a significant continuous proliferation of stem cells in extended long-term cultures. The continued expansion of stem cells in the absence of RAR antagonists indicates that even a relatively short pulse with the antagonist is sufficient to modify stem cell responses.

In an additional experiment, cultures were treated for one week only with cytokines only (control) or with cytokines and the RAR antagonist. A marked long-term effect of the RAR antagonist was noticed at week 13 of incubation, as is demonstrated in the results presented in Table 2 below. At week 20, the RAR antagonist pre-treated cultures deteriorated and the cells underwent normal differentiation, though in a slower kinetic that the control. These results indicate that a one-week RAR antagonist treatment is sufficient for dramatically modulating the proliferation ability of stem cells in ex-vivo conditions as the RAR antagonist transiently potentiate stem cell proliferation yet maintains their self-renewal ability.

TABLE 2

| Treatment | No. of CD34+ cells | No. of CFU*103 |
|---|---|---|
| Control (week 13) | 0 | 0 |
| Control (week 20) | 0 | 0 |
| RAR antagonist ($10^{-5}$ M) (week 13) | 10322 | 66355 |

TABLE 2-continued

| Treatment | No. of CD34+ cells | No. of CFU*103 |
|---|---|---|
| RAR antagonist ($10^{-5}$ M) (week 20) | 0 | 0 |

Figure 4:
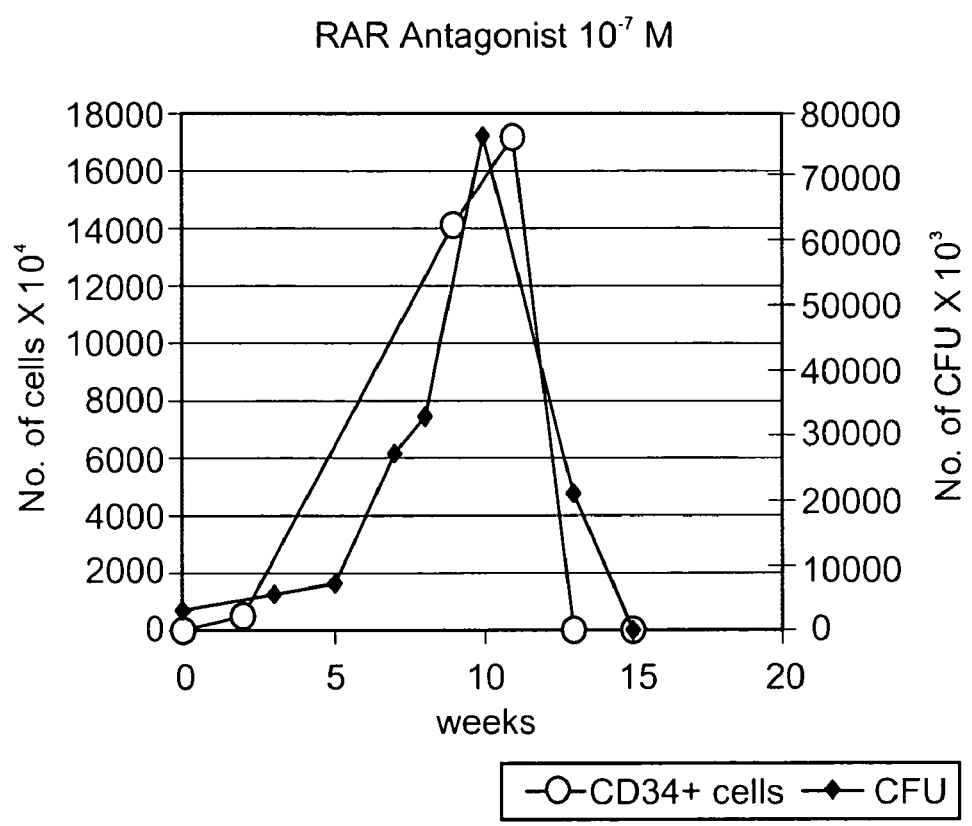
FIG. 4 is a graph of data collected by FACS analysis and LTC-CFU ability showing high levels of CD34$^+$ cell proliferation and long-term colony forming unit ability in ex-vivo cultures treated with $10^{-7}$ M of the RAR antagonist and a combination of the 4 cytokines, as above, up to almost 12 weeks post seeding. At 10 weeks and 11 weeks (CFUs and CD34 cells, respectively), these populations begin to decline.

The limited extensive and durable cell proliferation enabled by the RAR antagonist is further demonstrated in another experiment, where it was shown that ex-vivo cultures supplemented with the RAR antagonist AGN 194310 ($10^{-7}$ M or 0.41 microgram/liter) enabled cell proliferation, only until 11 weeks post initial seeding of culture cells (FIG. 4). CFU forming ability was assayed as well, yet peak colony forming unit ability preceded peak absolute number of CD34+ cells by approximately one week, whereupon a precipitous decline in proliferation was evident, at which point cellular differentiation occurred, as evidenced by the loss of clonogenic (CFU forming ability) potential of the culture. These results, which describe a normal behavior of stem cells, namely extensive proliferation followed by differentiation are in marked contrast to previous reports that integration of a dominant negative retinoid receptor gene sustain infinite proliferation, in other words, resulted in the creation of cell lines (Muramatsu M, Biochem Biophys Res Commun 2001 Jul. 27:285(4): 891-6 "reversible integration of the dominant negative retinoid receptor gene for ex vivo expansion of hematopoietic stem/progenitor cells), whereas in the present invention, cells were fully capable of normal differentiation, following extended ex-vivo proliferation.

A representative FACS chart plot of CD34+ cells 2 and 11 weeks following re-selection is shown in FIG. 5. While control cultures expressed markers for a more differentiated state, RAR antagonist treated samples expressed a less differentiated phenotype, as evidenced by the leftward shift in expression profile. These findings indicated that although not lineage negative, most of the CD34+ cells derived from RAR antagonist treated cultures expressed fewer lineage related surface markers.

RAR Antagonist Treatment of Mononuclear Cell Populations Expands a Population of Cells With a Less-Differentiated Phenotype Mononuclear cell fractions cultured in the presence of RAR antagonists and cytokines similarly revealed a significant increase in the number of CD34+Lin− cells (78%, 24%) as quantitated by FACS analysis from a reselected, highly purified CD34+ cell fraction, as compared to controls, 2 and 5 weeks (respectively), after initial seeding (Table 3). However, most remarkable is that these cells responded to the RAR antagonists and expanded an undifferentiated population, even in mixed culture conditions, without prior purification of the CD34+ population. RAR antagonist treatment was sufficient to stimulate specific expansion of the stem/progenitor cell compartment, as 5 weeks post seeding, while control MNCs had no detectable CD34+ population, RAR antagonist treated cultures revealed significant numbers of CD34+ cells, and those that were lineage marker deficient. Thus, any factors elaborated by the MNC culture cells that suppress CD34+ cell survival in control samples are insufficient to override the signal provided by the RAR antagonist to elaborate this compartment.

TABLE 3

Expansion of CD34+/Lin− mononuclear cells

|  | Cytokines only | Cytokines +RAR antagonist $10^{-6}$ M |
|---|---|---|
| 2 weeks | | |
| No of CD34 cells × $10^{4*}$ | 176 | 169 |
| No of CD34+/Lin− × $10^{4*}$ | 1.76 | 132.5 |
| % CD34/Lin− | 1 | 78.4 |
| 5 weeks | | |
| No of CD34 cells × $10^{4*}$ | 0 | 985 |
| No of CD34+/Lin− × $10^{4*}$ | 0 | 237.8 |
| % CD34/Lin− | 0 | 24.1 |

*Cumulative value

RAR Antagonist Treatment Enhances Long-Term Culture Colony Forming Unit (LTC-CFUc) Ability Demonstration of a culture's ability to form colony forming units (CFUs) is another functional, in vitro method for verifying the presence of stem and early progenitor cells with a high self-renewal potential. Here it is demonstrate that culture pre-treatment with RAR antagonists enabled greater expansion of cells with a self-renewal capacity as evidenced by the presence of increasing numbers of CFU cells during the extended long-term culture period.

Figure 6A:
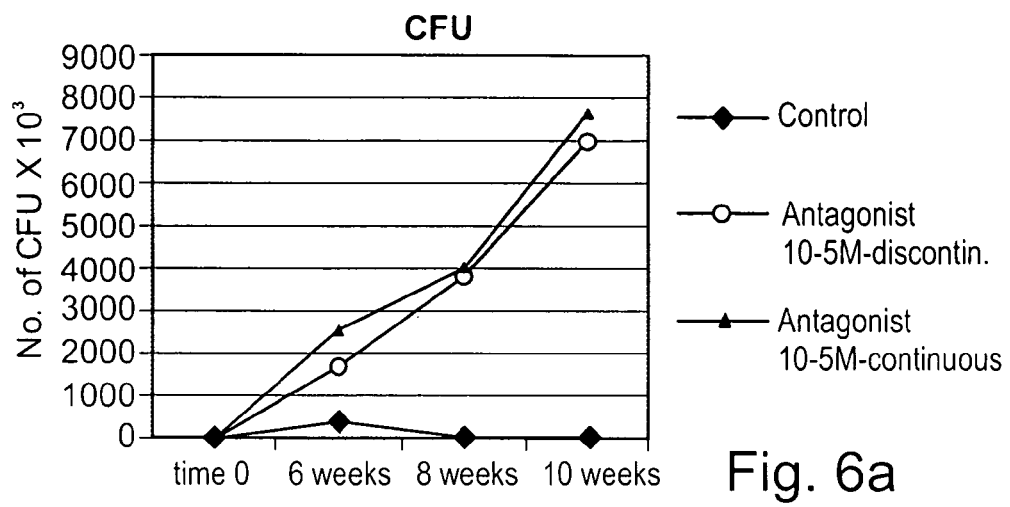
FIG. 6A is a graph of colony forming unit data showing that both long-term cultures pulsed for the first 3 weeks with the antagonists or cultures administered RAR antagonists continuously reveal a 5-fold increase in CFU content as compared to control values.
Figure 6B:
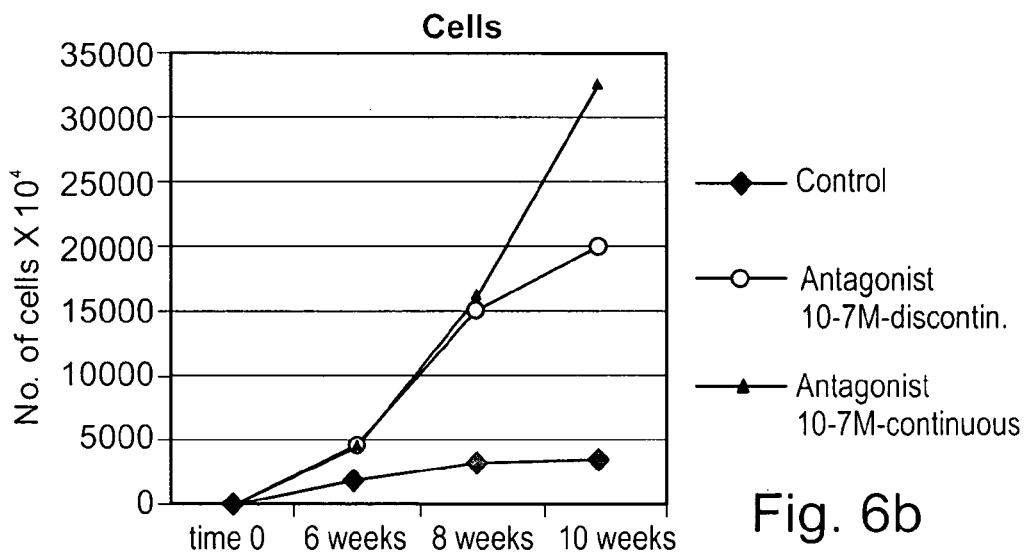
FIG. 6B is a graph of cell enumeration data showing that long-term cultures either pulsed for the first 3 weeks with antagonists, or administered RAR antagonists continuously, reveal a 5-fold increase in CFU content as compared to control values.
Figure 7:
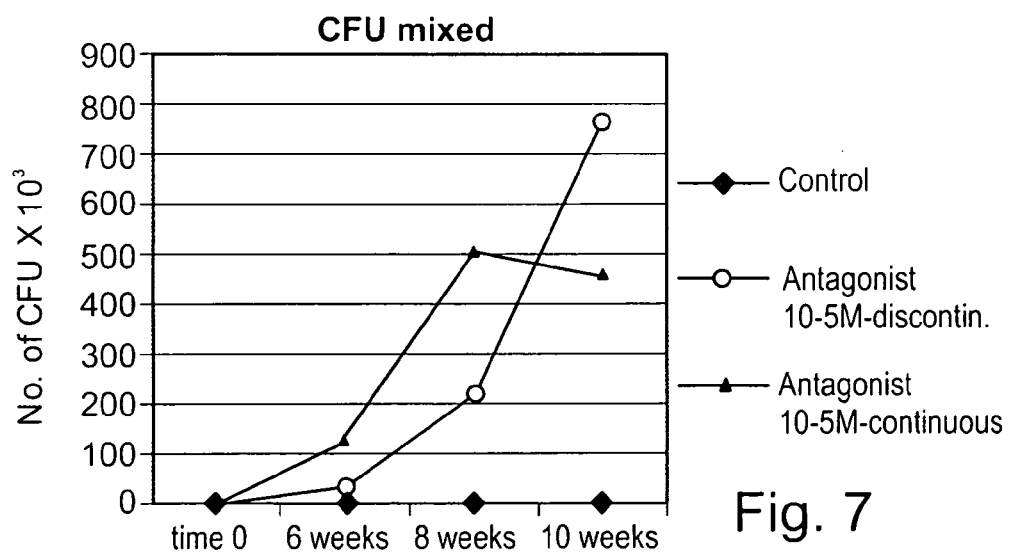
FIG. 7 is a graph of mixed colony forming unit data showing that both long-term cultures pulsed for the first 3 weeks with the antagonists or cultures administered RAR antagonists continuously reveal a dramatic increase in CFU content as compared to control values, with pulse-treatment yielding the highest CFU values.
Figure 13A:
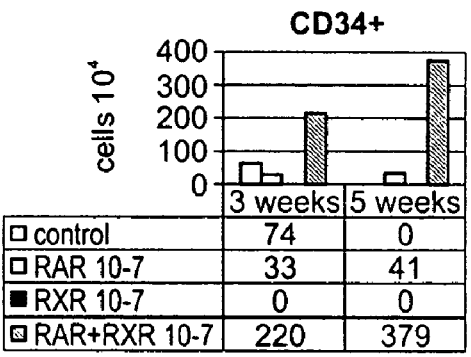
FIG. 13A is a bar graph presenting the data obtained by FACS analysis of cultures treated with a RAR antagonist AGN 194310, a RXR antagonist LGN 100754 and a combination thereof. Comparable CD34+ surface expression levels determined 3 and 5 weeks post seeding are evident. A marked increase in expression in cultures treated with a combination of the RAR and RXR antagonists, as compared with the untreated (cytokines only) control, the RAR antagonist and RXR antagonist treatments is demonstrated.
Figure 13B:
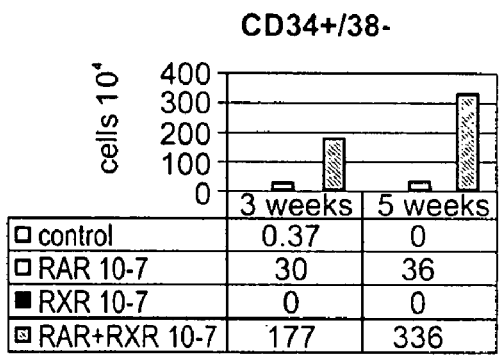
FIG. 13B is a bar graph presenting the data obtained by FACS analysis of cultures treated with an RAR antagonist AGN 194310, an RXR antagonist LGN 100754 and a combination thereof. Comparable CD34+/38− surface expression levels determined 3 and 5 weeks post seeding are evident. A marked increase in expression in cultures treated with the combination of RAR and RXR antagonists, as compared with the untreated control (cytokines only), the RAR antagonist and the RXR antagonist treatments is demonstrated.
Figure 13C:
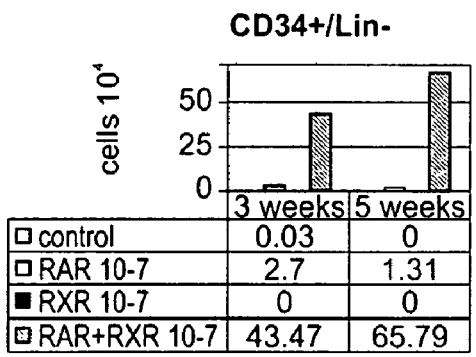
FIG. 13C is a bar graph presenting the data obtained by FACS analysis of cultures treated with an RAR antagonist AGN 194310, an RXR antagonist LGN 100754 and a combination thereof. Comparable CD34+/Lin− surface expression levels determined 3 and 5 weeks post seeding are evident. A marked increase in expression in cultures treated with the RAR and RXR antagonists combination, as compared with the untreated control (cytokines only), the RAR antagonist and the RXR antagonist treatments is demonstrated.
Figure 13D:
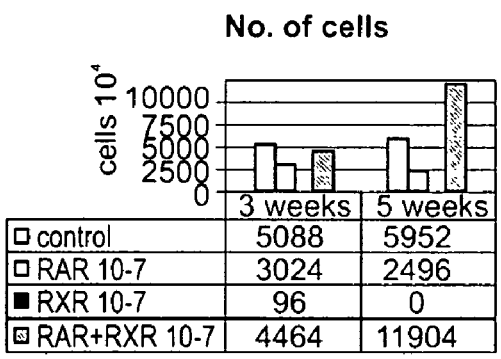
FIG. 13D is a bar graph presenting the total cell density of cultures treated with an RAR antagonist AGN 194310, an RXR antagonist LGN 100754 and a combination thereof. Comparable number of cells determined 3 and 5 weeks post seeding is evident. A significant increase of cell density in cultures treated with RAR+RXR antagonist 5 weeks post seeding, as compared with the untreated control (cytokines only), the RAR antagonist and RXR antagonist treatments is demonstrated.
Figure 13E:
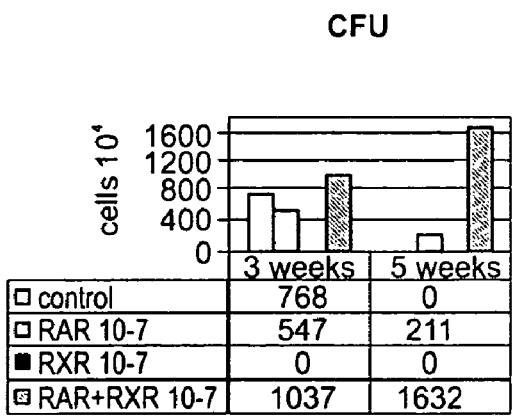
FIG. 13E is a bar graph presenting the colony-forming unit (CFU) data of cultures treated with an RAR antagonist AGN 194310, an RXR antagonist LGN 100754 and a combination thereof. Comparable CFU levels determined 3 and 5 weeks post seeding are evident. A marked increase in CFU in cultures treated with the RAR and RXR combination, as compared with the untreated control (cytokines only), the RAR antagonist and the RXR antagonist treatments is demonstrated.

Long-term CD34+ cell cultures were supplemented with a combination of 4 cytokines, Flt3, TPO, IL-6 and IL-3, with and without varying predetermined concentrations of the RAR antagonist AGN 194310. RAR antagonist treatment of the cultures was for a limited period of three weeks or was continuous during the entire culture period. The ability to form CFUs was determined for long-term (6 weeks) cultures treated with 2 doses of the RAR antagonist for a short pulse or continuously and was compared to control samples treated with cytokines alone. Long-term cultures pulsed for the first 3 weeks with the antagonist revealed a 5-fold increase in CFU content as compared to control cultures (FIGS. 6A and 6B. Enumeration of mix-colonies indicated that control cultures did not contain any mix-colony forming unit cells, whereas antagonist treated cultures contained a higher number of cells with CFU-mix potential (FIG. 7).

RAR Antagonist Treatment Enhances Extended Long-Term Culture Colony Forming Unit (LTC-CFUc) Ability:

The ability to form CFUc was determined for extended long-term (8-10 week) cultures treated with the RAR antagonists, as well. The differences in CFU content were significantly more pronounced during this culture period. RAR antagonist treatment markedly increased CFUc content between week 6 to 10, as compared to control cultures, which lost the ability to regenerate cells with CFU potential (FIGS. 6A and 6B) RAR antagonist pulse-treatment or continuous treatment increased CFU content by 15×$10^4$. Pulse treatment with the antagonist yielded the highest level of CFU-mix content, as well (FIG. 7)

Example 2

RAR-Antagonists and Their Use in Ex-Vivo Hepatocyte Expansion

Material and Experimental Methods

Isolation and Culture of Primary Hepatocytes:

Three intact livers were harvested from 3 week old VLVC female mice (Harlan Laboratories, Jerusalem, Israel), dissected and washed twice with DMEM (Beit Haemek, Israel), incubated with DMEM in the presence 0.05% collagenase for 30 minutes at 37° C., ground and passed through a 200 µm mesh sieve, yielding individual hepatocytes. Cells were washed twice and viability was ascertained with trypan blue. Cells were plated in collagen-coated, 35 mm tissue culture plates at a density of 4-×$10^4$ live cells/ml in F12 media (containing 15 mM Hepes, 0.1% glucose, 10 mM sodium bicarbonate, 100 units/ml penicillin-streptomycin, glutamine, 0.5 units/ml insulin, 7.5 m cg/ml hydrocortisone, and 10% fetal bovine serum). Medium was changed after 12 hours, the cells were washed twice with phosphate buffered saline (PBS) and new medium was added. Medium was changed twice a week.

Hepatocytes were also grown in the presence of Epidermal Growth Factor (EGF), Platelet-Derived Growth Factor β chain (PDGF-BB), Fibroblast growth Factors (FGF4) and Hepatocyte Growth Factor (HGF), at 20-50 ng/ml each, for the entire culturing period according to the method of Schwartz et al. (Schwartz R E, Reyes M, Koodie L, Jiang Y, Blackstad M, Lund T, Lenvik T, Johnson S, Hu W S, Verfaillie C M. Multipotent adult progenitor cells from bone marrow differentiate into functional hepatocyte-like cells. J Clin Invest. 2002; 109 (10): 1291-302). Hepatocytes were also grown in serum free medium according to the method of Runge et al. (Runge D, Runge D M, Jager D, Lubecki K A, Beer Stolz D, Karathanasis S, Kietzmann T, Strom S C, Jungermann K, Fleig W E, Michalopoulos G K. Serum-free, long-term cultures of human hepatocytes: maintenance of cell morphology, transcription factors, and liver-specific functions. Biochem Biophys Res Commun. 2000; 269(1): 46-53).

In all of the above-mentioned hepatocytes culture conditions, cells are grown in the presence or absence of the retinoic acid antagonist AGN 194310 at concentrations ranging from $10^{-5}$ M to $10^{-9}$ M.

After a period of 3 weeks, cultures treated with $10^{-5}$ M antagonist were detached with 0.25% trypsin, split and replated at a 1:2 ratio. The cells were either immunostained as described below, or visualized with Giemsa staining.

Murine hepatocyte cultures supplemented with EGF and HGF were evaluated as primary cultures, or following first and second passages. First passage cultures were grown for 2 weeks, split 1:2 and immunostained 8 days later for the presence of albumin, as described below. Second passage cultures were similarly grown for 2 weeks, split 1:2, and grown for an additional week, then split 1:4 and similarly immunostained 4 days later.

Histologic Characterization:

Hepatocytes and ex-vivo expanded cells were fixed in methanol directly in their cell culture plates and each procedure performed by standard procedures as outlined below.

The cellular uptake of organic anions by culture hepatocytes commonly use as markers of hepatocyte functionality, was studied by indocyanine green (ICG) dye uptake. ICG (Sigma, Jerusalem, Israel)) was dissolved in DMEM yielding a final concentration of 1 mg/ml (Yamada T, Yoshikawa M, Kanda S, Kato Y, Nakajima Y, Ishizaka S, Tsunoda Y. In vitro differentiation of embryonic stem cells into hepatocyte-like cells identified by cellular uptake of indocyanine green. Stem Cells. 2002; 20(2): 146-54). Ten days cultured hepatocytes were washed twice with PBS and incubated with 400 µl of the dye for 15 minutes at 37° C. Samples were then rinsed 3 times with PBS, and visualized by light microscopy.

Ex-vivo expanded cells and hepatocytes were stained with Giemsa stain, according to manufacturer's instructions (Shandon, Pittsburg, Pa.) for 4 minutes at room temperature, washed in buffer solution for 4 minutes and washed 3-4 times with rinse solution.

Immunocytochemistry

Hepatocytes were probed for expression of α-fetoprotein (AFP) using a rabbit polyclonal antibody raised against a recombinant protein of human origin that cross-reacts with AFP from mouse (H-140 Santa Cruz Technology, Santa Cruz, Calif.), and albumin using a rabbit antiserum to mouse albumin (Cappel-ICN, Aurora, Ohio). Cells were fixed in methanol at −20° C. for 10 minutes, rinsed with PBS for 5 minutes, and permeabilized with 0.1% triton-X (Sigma, Jerusalem, Israel) in PBS for 5 minutes. The cells were then washed with Tris buffer saline (TBS) for 5 minutes and incubated with 1% bovine serum albumin (BSA) in PBS for 10 minutes. Endogeneous peroxidases were inactivated by incubation with peroxidase block (Envision, Dako, Carpinteria, Calif.) for 5 minutes, at room temperature. Cells were incubated with antibodies raised in rabbit against mouse albumin (at a dilution of 1:100); or against α-fetoprotein (at a dilution of 1:25) for 30 minutes. Samples were then visualized for peroxidase activity (via methods according to manufacturer's instructions using the Envision HRP-system (Dako, Carpinteria, Calif.), and counterstained with hematoxylin (Dako, Carpinteria, Calif.).

Experimental Results

Primary cultures derived from 3 weeks old mouse livers, grown in media in the absence of cytokines, were probed for the expression of hepatocyte-specific markers including early development markers like β-fetoprotein (which is specific for less differentiated progenitor cells) and albumin which is a marker for mature hepatocytes, following 3 weeks in culture. Cultured cells stained positively (red-brown precipitate) for α-fetoprotein (FIG. 8A), and for albumin (data not shown) indicating the presence of functional hepatocytes. Incubation of the cultures in the presence of the $10^{-5}$ M retinoic acid antagonist resulted in an increase in the fraction of cells that stained positively for α-fetoprotein as compared to control cultures (FIG. 8B). This increase may signal the proliferation of early hepatocytes. Similarly, giemsa staining of the cultures revealed a large population of oval cells (hepatocyte stem progenitor cells are defined as oval cells) in cultures treated with the retinoic acid antagonist (FIG. 9B) while few were apparent in untreated control cultures (FIG. 9A).

Hepatocytes cultures grown in the presence of the antagonist and in the absence of cytokines for 3 weeks were trypsinized, split, and replated. The cells reattached to the culture plate and revealed typical hepatocytic morphology (FIG. 9C), as opposed to previous data indicating a difficulty in growing primary hepatocytes for extended periods of time in culture, especially in the absence of cytokines (Wick M, Koebe H G, Schildberg F W. New ways in hepatocyte cultures: Cell immobilization technique ALTEX. 1997; 14(2): 51-56; Hino H, Tateno C, Sato H, Yamasaki C, Katayama S, Kohashi T, Aratani A, Asahara T, Dohi K, Yoshizato K. A long-term culture of human hepatocytes which show a high growth potential and express their differentiated phenotypes. Biochem Biophys Res Commun. 1999 Mar. 5;256(1):184-91; Tateno C, Yoshizato K. Long-term cultivation of adult rat hepatocytes that undergo multiple cell divisions and express normal parenchymal phenotypes. Am J Pathol. 1996; 148(2): 383-92).

The supplementation of the culture media with growth factors in primary hepatocyte cultures treated with RAR antagonist revealed similar results to unsupplemented cultures, in that supplemented cultures stained positively for the production of α-fetoprotein (FIG. 10C), as compared to control cultures, supplemented with growth factors, but deprived of the RAR antagonist, where no immunostaining was evident (FIG. 10D). Background staining, as determined by probing for albumin expression, was negligible in RAR antagonist treated (FIG. 10A) and untreated, supplemented cultures (FIG. 10B). Thus culture supplementation with growth factors alone is insufficient to expand a less-differentiated cellular phenotype.

Similarly, first and second passages of growth factor-supplemented hepatocyte cultures were evaluated for their ability to persist in culture. In first passage growth factor-supplemented cultures both RAR antagonist treated (FIG. 11B) and untreated control cultures (FIG. 11A) revealed the presence of typical hepatocytes, however only RAR treated cultures (FIGS. 11C and D) revealed a large number of islets of oval cells, indicative of a hepatocyte stem cell population.

Second passage growth factor-supplemented cultures showed a marked diminishment in the number of hepatocytes evident in control cultures (FIG. 11E), as compared to RAR treated cultures (FIG. 11F), indicative of a failure of growth factor supplementation alone to provide expanded and persistent hepatocytes in culture. Only RAR antagonist treatment enabled expansion and long-term culture of hepatocyte populations.

Example 3

RXR and RAR+RXR Antagonists and Their Use in Ex-Vivo Cell Expansion

Material and Experimental Methods

Synthesis of the RXR Antagonist (2E, 4E, 6Z)-7-[3-propoxy-5,6,7,8 tetrahydro-5,5,8,8-tetramethyl-2-naphthalene-2-yl]-3-methylocta-2,4,6-trienoic acid] (LGN 100754):

The synthesis of LGN100754 was based on (i) Canan-Koch et al. J. Med. Chem. 39, 17, 3229-3234 [reaction scheme, page 3231; and (ii) Synthetic protocols from International Application No. PCT/US96/14876 (WO 97/12853) entitled Dimer-Selective RXR Modulators and Methods for Their Use. All materials were purchased from Ligand Pharmaceuticals Inc.

Synthesis of 6-ethynyl-1,1,4,4-tetramethyl-7-propoxy-1,2,3,4-tetrahydronaphthalene:

Phosphorus oxychloride (0.234 grams, 0.142 ml, 1.52 mmol) was added dropwise to dimethyl formamide (DMF) (4 ml) at room temperature under a nitrogen atmosphere. The solution was stirred for 30 minutes. The 1-(3-propoxy-5,6,7,8-tetrahydro-5,5,8,8,-tetramethylnaphthalen-2-yl)ethanone was added quickly (in one portion) to the orange solution, the reaction solution was heated to 60° C. and was stirred for 12 hours. The obtained dark brown solution was poured into ice water and the aqueous layer was adjusted to pH 7 with solid sodium hydrogen carbonate. Ethyl acetate extraction afforded the crude product, the chloroenal (6-[1-hydroxy,2-chloro-ethenyl]-1,1,4,4-tetramethyl-7-propoxy-1,2,3,4-tetrahydronaphthalene), 0.128 grams, as an orange/brown oil. A solution of the crude chloroenal in dioxane:water (3:2; 5 ml) was added to a solution of NaOH (0.061 grams, 1.52 mmol) in dioxane: $H_2O$ (3:2; 20 ml), at 80° C., and the reaction mixture was stirred for 2 hours, to yield an orange reaction solution. The reaction solution was cooled to room temperature, poured into brine and extracted with EtOAc. The organic phase was dried (MgSO4), filtered, and concentrated to afford an orange oil which was purified by radial chromatography (10:1 hexane:ethyl acetate) to give the product 6-ethynyl-1,1,4,4,-tetramethyl-7-propoxy-1,2,3,4-tetrahydronaphthalene (39%) as a yellow oil [$^1$H-NMR (400 MHz, $CDCl_3$): d 7.38(s, 1H, Ar—H), 6.76(s,1H, Ar—H), 3.98 (t, J=6.6 Hz, 2H, OCH$_3$), 3.19 (s, 1H, CH),1.83 (m, 2H, CH$_2$),1.66 (m, 2H, 2CH$_2$),1.26 (s, 6H, 2CH$_3$),1.23 (s, 6H, 2CH$_3$), 0.93 (t, J=7.4 Hz, 3H, CH$_3$)].

Synthesis of 3-(3-propoxy-5,6,7,8-tetrahydro-5,5,8,8 tetramethylnaphthalene-2-yl)propynenitrile:

Ethyl magnesium bromide (3.33 ml of a 1.0 M solution in THF, 3.32 mmol) was added dropwise to a room temperature solution of the acetylene ether (6-ethynyl-1,1,4,4,-tetramethyl-7-propoxy-1,2,3,4-tetrahydronaphthalene) (0.450 grams, 1.66 mmol) in THF (10 ml). The solution was heated to reflux for 6 hours and then cooled to room temperature. Phenyl cyanate (0.40 grams, 0.50 ml, 3.33 mmol) was added (neat) to the reaction solution and the reflux was continued for additional 2 hours. The reaction solution was cooled to room temperature and quenched with a saturated ammonium chloride solution. Aqueous workup followed by radial chromatography (20:1hexanes:EtOAc) afforded the product 3-(5,5,8,8-tetramethyl-3-propoxy-5,6,7,8-tetrahydronaphthalen-2-yl)-propynenitrile (80%) as a yellow solid; $^1$H-NMR (400 MHz, CDCl$_3$): d 7.44 (s, 1H, Ar—H), 6.78 (s, 1H, Ar—H), 3.97 (t, J=6.5 Hz, 2H, OCH$_2$), 1.83 (m, 2H, CH$_2$), 1.67 (m, 2H, 2CH$_2$), 1.27 (s, 6H, 2CH$_3$), 1.24 (s, 6H, 2CH$_3$), 1.03 (t, J=7.3 Hz, 3H, CH$_3$).

Synthesis of 3-(3-propoxy-5,5,8,8,-tetramethyl-5,6,7,8-tetrahydro-naphthalene-2-yl)but-2-enenitrile:

A flame dried flask was charged with a suspension of copper(I) iodide (0.057 grams, 0.298 mmol) in THF (5 ml) and the mixture was stirred at 0° C. under nitrogen atmosphere. Methyl lithium (0.43 ml of a 1.4 M solution in ether, 0.596 mmol) was added dropwise to give a colorless solution. The solution was cooled to −78° C. and afforded a yellow/brown color. The acetylene nitrile 3-(5,5,8,8-tetramethyl-3-propoxy-5,6,7,8-tetrahydronaphthalene-2-yl)propionitrile (0.040 grams, 0.135 mmol) in THF (3.0 ml) was added dropwise and the solution was stirred at −78° C. for 45 minutes and then quenched with methanol (5 ml). An aqueous workup afforded the cis-alkene nitrile 3-(3-propoxy-5,5,8,8,-tetramethyl-5,6,7,8-tetrahydro-naphthalene-2-yl)but-2-enenitrile (97%) as a yellow oil; $^1$H-NMR (400 MHz, CDCl$_3$): d 7.19 (s, 1H, Ar—H), 6.78 (s, 1H, Ar—H), 5.35 (s, 1H, olefinic), 3.92 (t, J=6.4 Hz, 2H, OCH$_2$), 2.27 (s, 3H, CH$_3$), 1.79 (m, 2H, CH$_2$), 1.67 (s, 2H, 2CH$_2$), 1.28 (s, 6H, 2CH$_3$), 1.27 (s, 6H, 2CH$_3$), 1.02 (t, J=7.4 Hz, 3H, CH$_3$).

Synthesis of (2E, 4E, 6Z)-7-3[-propoxy-5,6,7,8-tetrahydro-5,5,8,8-tetramethyl-2-naphthalene-2-yl]-3-methylocta-2,4,6-trienoic acid]:

A round-bottomed flask equipped with N$_2$ bubbler, septa, and a stir bar was charged with a solution of 3-(3-propoxy-5,5,8,8,-tetramethyl-5,6,7,8-tetrahydro-naphthalene-2-yl)-but-2-enenitrile adduct in hexanes (5 ml) and toluene (5 ml), and was then cooled to −78° C. DIBAL (3.71 ml of a 1.0 M solution in toluene, 5.6 mmol) was added dropwise via syringe to the solution which was then stirred for 1.5 hour at −78° C., quenched with aqueous sodium potassium tartarate solution (10 ml) and warmed to room temperature over 30 minutes. The aqueous layer was acidified (1.0 M HCl to pH=4) and extracted with EtOAc (3×10 ml). The combined organic extracts were washed with water and brine, dried (sodium sulfate), filtered, and concentrated to give the cis-alkenyl, cis-3-(3-propoxy-5,5,8,8-tetramethyl-5,6,7,8-tetrahydro-naphthalene-2-yl)but-2-enal as a yellow oil; $^1$H-NMR (400 MHz, CDCl$_3$): d 9.36 (d, J=8.4 Hz, 1H, CHO), 6.99 (s, 1H, Ar—H), 6.79 (s, 1H, Ar—H), 6.09 (s, J=8.4 Hz, 1H, olefinic), 3.90 (t, J=6.5 Hz, 2H, OCH$_2$),2.29 (s, 3H, CH$_3$),1.76 (m, 2H, CH$_2$), 1.68 (s, 2H, 2CH$_2$), 1.3 (s, 6H, 2CH$_3$), 1.24 (s, 6H, 2CH$_3$), 1.00 (t, J=7.4 Hz, 3H, CH$_3$).

A flame-dried round-bottomed flask equipped with a nitrogen bubbler, septa, and a stir bar was then charged with a solution of diethyl 3-ethoxycarbonyl-2-methyl-prop-2-enyl phosphonate (0.417 grams, 1.58 mmol, 0.39 ml) in THF (2.0 ml) and 1,3-Dimethyl-3,4,5,6-tetrahydro-2(1H)-pyrimidinone (DMPU, 0.7 ml). The solution was cooled to −78° C., and n-butyl lithium (0.96 ml of a 1.5 M solution in hexanes, 1.44 mmol) was added drop-wise via a syringe. The reaction mixture was warmed to 0° C. and stirred for 15 minutes. The resulting solution was then cooled to −78° C. and cis-3-(3-propoxy-5,5,8,8-tetramethyl-5,6,7,8-tetrahydro-naphthalene-2-yl)but-2-enal (1.31 mmol) was added dropwise via cannula. The solution was warmed to ambient temperature. After stirring for 1.5 hours, the reaction was quenched with water (15 ml), and the aqueous layer was extracted with EtOAc (3×10 ml). The combined organic layers were washed with aqueous CuSO$_4$, water, and brine, dried under sodium sulfate, filtered, and concentrated to give a crude ester (2E, 4E, 6Z)-7-3 [-propoxy-5,6,7,8-tetrahydro 5,5,8,8-tetramethyl-2-naphthalene-2-yl]-3-methyl-octa-2,4,6-trienoic acid ethyl ester. The crude ester was hydrolyzed with KOH (excess) in methanol (7 ml) at reflux temperature and quenched with 1 M HCl (5 ml). The solution was concentrated, diluted with water (10 ml) and the aqueous layer was extracted with EtOAc (3×15 ml). The combined organic layers were washed with water and brine, dried over NaSO$_4$, filtered, concentrated, purified by radial chromatography followed by preparative silica gel TLC to give (2E, 4E, 6Z)-7-3[-propoxy-5,6,7,8-tetrahydro-5,5,8,8-tetramethyl-2-naphthalene-2-yl]-3-methylocta-2,4,6-trienoic acid] as a pale yellow solid; m.p. 177-179° C.; $^1$H-NMR (400 MHz, CDCl$_3$): d 6.95 (s, 1H, Ar—H), 6.79 (s, 1H, Ar—H), 6.62 (dd, J=15.3, 11.0 Hz, 1H, olefinic), 6.22 (appp br d, 2H, 2* olefinic), 5.76 (s, 1H, olefinic), 3.89 (t, J=6.5 Hz, 2H, OCH$_2$), 2.19 (s, 3H, CH$_3$), 2.13 (s, 3H, 2CH$_3$, 1.77(m, 2H, CH$_2$), 1.68 (s, 4H, 2CH$_2$), 1.30 (s, 6H, 2CH$_3$), 1.23 (s, 6H, 2CH$_3$), 1.01 (t, J=7.4 Hz, 3H, CH$_3$).

Synthesis of the RAR+RXR Antagonist 4-[5H-2,3-(2,5-Dimethyl-2,5-Hexano) 5-Methyl-8-nitrodibenzo [b,e][1,4] diazepin-11-yl] Benzoic acid [designated HX 531]:

Synthesis of the RAR+RXR antagonist HX531 was accomplished based on the procedure described by Masyuki Ebisawa et al., Chem. Pharm. Bull., 47(12): 1778-1786 (1999).

Synthesis of 2,5-Dimethyl-2,5-hexanediol:

Solutions of hydrogen peroxide (1.05 moles) and ferrous sulfate (1 mole and 1 mole of sulfuric acid) were added simultaneously and equivalently to an aqueous solution of t-butyl alcohol (285 ml or 3 moles in 800 ml of water containing 23 ml of sulfiric acid) at 30° C. A 36% yield of semi-solid product possessing a camphor-like odor was thereby isolated. The 2,5-dimethyl-2,5-hexanediol product was purified by drying and recrystallization (EtOAc) (melting point (mp): 85-87° C.).

Synthesis of 2,5-dichloro-2,5-dimethylhexane:

The synthesis was accomplished as previously described [Mayr, H., et al., Chem. Ber. 124: 203, 1999]. 2,5-Dimethyl-2,5-hexanediol (73.1 grams, 0.500 mol) was stirred with 37% aqueous HCl (250 ml) for 1 hour. The initially homogeneous mixture precipitated to yield a crystalline product. The product was extracted with 600 ml of petroleum ether and dried with CaCl$_2$. Evaporation of the solvent yielded 81.9 grams (89%) of an NMR-spectroscopically pure solid, which was recrystallized from petroleum ether (mp: 68-68.5° C.) as 2,5-dichloro-2,5-dimethylhexane.

Synthesis of 6-bromo-1,2,3,4-tetrahydro-1,1,4,4-tetramethylnaphthalene:

A 200 ml round-bottomed flask equipped with a stir bar and a reflux condenser was charged with a solution of bromobenzene (109 mmol, 17 ml) and 2,5-dichloro-2,5-dimethyl hexane (10 grams, 54.6 mmol) in dichloromethane (30 ml). Aluminum chloride (1.45 grams, 10.9 mmol) was added to the solution slowly, until spontaneous reflux subsides. After stirring for 10-15 minutes at room temperature, the reaction was poured into ice water (30 ml) and the layers were separated. The aqueous layer was extracted with EtOAc (5×20 ml). The combined organic layer was washed with water and brine, dried over sodium sulfate, filtered, and concentrated, to yield a 6-bromo-1,2,3,4-tetrahydro-1,1,4,4-tetramethylnaphthalene product.

A mixture of 6-bromo-1,2,3,4-tetrahydro-1,1,4,4-tetramethylnaphthalene (30 grams, 110 mmol), potassium carbonate (56.1 grams, 41 mmol) and copper iodide (4.53 grams) in o-xylene (300 ml) was heated at 150° C. for 14 hours. After removal of the solvent, the residue was purified by silica gel column chromatography (EtOAc:n-hexane 1:100) to yield the product 2-nitro-1-amino-[1,2,3,4-tetrahydro-1,1,4,4-tetramethylnaphthalene]-benzene as red plates (n-hexane) (36.09 grams, 82% yield of title product, mp: 118'C].

A solution of 2-nitro-1-amino-[1,2,3,4-tetrahydro-1,1,4,4-tetramethylnaphthalene]-benzene (500 mg, 1.54 mmol) in DMF (10 ml) was added to a suspension of NaOH (60%, 92 mg, 2.31 mmol) in DMF (1 ml) and the mixture was stirred for 30 minutes, followed by addition of methyl iodide (0.5 ml) and additional stirring for 1 hour. After removal of the solvent, the residue was taken up in water, and was extracted with dichloromethane. The organic layer was washed with water and brine, and was dried over $MgSO_4$. Removal of the solvent under vacuum gave a crude product 2-nitro-1-methylamino-[1,2,3,4-tetrahydro-1,1,4,4-tetramethyl-naphthalene]benzene (543 mg).

2-Nitro-1-methylamino-[1,2,3,4-tetrahydro-1,1,4,4-tetramethyl -naphthalene]benzene (540 mg, 1.53 mmol) was dissolved in 20 ml of ethanol, and was hydrogenated over 10% ethyl alcohol (55 mg) for 1 hour. After filtration and removal of the solvent, the residue was chromatographed on silica gel (EtOAc:n-hexane 1:8) to give 2-amino-1-methylamino-[1,2,3,4-tetrahydro-1,1,4,4-tetramethyl-naphthalene]benzene as the product.

Terephthalic acid monomethyl ester chloride (381 mg, 1.91 mmol) was added to a solution of 2-amino-1-methylamino-[1,2,3,4-tetrahydro-1,1,4,4-tetramethyl-naphthalene]benzene (420 mg, 1.3 mmol) in benzene (10 ml) and pyridine (2 ml). The mixture was stirred for 4 hours, then poured into 2N hydrochloric acid, and extracted with EtOAc. The organic layer was dried and was then purified over silica-gel (EtOAc:n-hexane 1:8) to give the product 2-[amido-4-benzoic acid methyl-ester]-1-methyl-amino[1,2,3,4-tetrahydro-1,1,4,4-tetramethyl-naphthalene]-Benzene (631 mg).

A solution of 2-[amido-4-benzoic acid methyl-ester]-1-methyl-amino[1,2,3,4-tetrahydro-1,1,4,4-tetramethyl-naphthalene]-Benzene (630 mg, 1.30 mmol) in dichloromethane was added to polyphosphoric acid (6.0 grams) and the mixture was heated at 110° C. for 18 hours. After cooling, water was added to the reaction and the product was extracted with dichloromethane. The organic layer was washed with brine, dried over magnesium sulfate, and 10 evaporated. The residue was purified by silica-gel column chromatography (EtOAc: n-hexane 1:6) to yield the product 2-[amido-4-benzoic acid methyl ester]-1-methylamino[1,2,3,4-tetrahydrol,1,4,4-tetramethylnaphthalene]4-nitrobenzene (104 grams).

$KNO_3$ (73 mg, 0.72 mmol) was added to a solution of 2-[amido-4benzoic acid methyl ester]-1-methylamino[1,2,3,4-tetrahydrol, 1,4,4-tetramethylnaphthalene]4-nitrobenzene (200 mg, 0.44 mmol) in sulfuric acid (12 ml) at 0° C. After 2.5 hours, the mixture was poured into ice water and extracted with dichloromethane. The organic layer was washed successively with 1N $NaHCO_3$, water and brine, and dried over $MgSO_4$. After evaporation, the residue was purified by silica gel column chromatography (EtOAc:n-hexane 1:8) to give methyl 4-(5H-2,3-(2,5-dimethyl-2,5-hexano)-5-methyl-8-nitrodibenzo[b,e][1,4] diazepin-1-yl) benzoate (100 mg, 45.5%) and the product recovered (84 mg). This compound was hydrolyzed under basic conditions (2N NaOH/EtOH) as follows:

Synthesis of 4-(5H-2,3-(2,5-dimethyl-2,5-hexano)-5-methyl-8-nitrodibenzo[b,e][1,41 diazepin-11-yl) benzoic acid:

A solution of (5H-2,3-(2,5-dimethyl-2,5-hexano)-5-methyl-8-nitrobenzo[b,e][1,4]diazepin-11-yl]benzoic acid methyl ester (84 mg) in ethanol (4 ml) and 2N NaOH (2 ml) was stirred at room temperature for 2 hours. The mixture was poured into 2N hydrochloric acid, and extracted with dichloromethane. The organic layer was washed with brine, and dried over magnesium sulfate. After evaporation, the crude product was purified by silica gel column chromatography (dichloromethane:methanol 20:1, then 8:1) to give the product 4-(5H-2,3-(2,5-dimethyl-2,5-hexano)-5-methyl-8-nitrodibenzo[b,e] [1,4] diazepin-1]-yl) benzoic acid, or HX531.

RXR, RAR and RAR+RXR Antagonists Supplementation of Ex-Vivo Hematopoietic Stem/Progenitor Cell Cultures:

Cultures were prepared and maintained as described above. RXR, RAR, or RAR+RXR antagonists were added to some cultures at concentrations ranging from $10^{-4}$ M to $10^{-9}$ M (100 μM to $10^{-3}$ M] concentrations corresponding to diluting concentrations of 1550 μg/l to 0.155 μg/1]. The antagonist was added for a predetermined, limited time period, for up to three weeks or continuously during the entire culture period.

All other procedures including mononuclear cell fraction collection and purification, purification of $CD34^+$ cells from mononuclear cell fractions, ex-vivo expansion of $CD34^{+/-}$ populations, morphological assessment, surface antigen analysis, determination of CD34 and other hematopoietic marker expression and cell population calculations were carried out as described in the experimental methods section of Example 1 above.

Experimental Results

Comparative Effects of RAR, RXR and RAR+RXR Antagonists and a Combination of RAR and RXR Antagonists on the Ex Vivo Expansion of Stem and Progenitor Cells in Culture:

$CD34^+$ cell enriched cultures were initiated in the presence of a combination of 4 cytokines (TPO, FLT3, IL-6 and IL-3), with and without different concentrations of the following antagonists: (i) a retinoic acid receptor (RAR) antagonist AGN 194310, (ii) a retinoic X receptor (RXR) antagonist LGD 100754 and (iii) a combination of the RAR antagonist AGN 194310 and the RXR antagonist LGD 100754. Three and five weeks after the initial seeding, the percentage of cells bearing the $CD34^+$ marker (considered to be mostly committed progenitor cells), as well as the percentage of cells bearing the markers $CD34^+/CD38^-$ and $CD34^+Lin^-$ (considered to represent the stem and early progenitor compartment) were ascertained by FACS analysis.

The data obtained from cell population counts, CFU counts and FACS analyses are illustrated in FIGS. 12a-b and 13a-e. The results show that while the RXR antagonist has no activity and the RAR antagonist exerts moderate activity when supplemented to the culture media at a concentration of $10^{-7}$ M and along with the cytokine IL-3 (cell-differentiation accelerator), treatment with the combination of RAR and RXR antagonists resulted in substantially higher levels of CFU, $CD34^+$ cells, $CD34^+/38^-$ cells, and $CD34^+/Lin^-$ cells, as compared with the control (cytokines only), the RAR antagonist treatment, and the RXR antagonist treatment. Clearly, the combination of RAR and RXR antagonists exerts a synergistic effect on the ex vivo expansion of stem/progenitor cells.

In an additional experiment, $CD34^+$ cell enriched cultures were initiated in the presence of a combination of 4 cytokines (TPO, FLT3, IL-6 and IL-3), with and without the RAR+RXR antagonist HX-531 (i.e., antagonist to both retinoic acid and retinoic X receptors) ($10^{-6}$ M; MW=483). The levels of CFU and $CD34^+$ cells were determined 3, 7, 9 and 11 weeks after the initial seeding. The results of this experiment are summarized in Table 4 below.

TABLE 4

| Time after seeding | CONTROL (cytokines only) | | RAR + RXR ANTAGONIST HX-531 ($10^{-5}$M) | |
|---|---|---|---|---|
| (weeks) | CFU ($\times 10^3$) | $CD34^+$ ($\times 10^4$) | CFU ($\times 10^3$) | $CD34^+$ ($\times 10^4$) |
| 3 | 2256 | 181 | 1920 (120 mixed) | 167 |
| 5 | 1338 | 46 | 8542 | 1636 |
| 9 | 307 | 0 | 36557 | 4977 |
| 11 | 0 | 0 | 67338 | 4055 |

These results indicate that the RAR+RXR antagonist preferably enables marked proliferation, yet limited differentiation of the stem cell compartment, thus directly impact the high fold expansion of stem/progenitor cells during short- and long-term culture period.

Example 4

Synthesis of the Vitamin D Receptor (VDR) Antagonist 1 alpha, 25-(OH) 2D3-26,23-lactone:

Synthesis of the four diastereoisomers of 1 alpha, 25-(OH) 2D3-26,23-lactone can be accomplished as described in Ishizuka, S. et. al, Archives of Biochemistry and Biophysics 242: 82,1985, or according to the following procedure.

Synthesis of Methyl 4-Iodo-2-Methyl-Butyrate:

To a suspension of lithium in 2 ml ether (dry) under stream of nitrogen, a solution of phenyl bromide in 3 ml ether was added dropwise. The reaction mixture was heated until complete dissolution of the lithium was achieved. A solution of methylene iodide in ether was prepared under a stream of argon and was cooled to −78° C. The phenyl lithium solution was added dropwise to this solution by a syringe during 0.5 hour, and a solution of methyl (R)-(+)-3-bromo-2-methylpropionate in ether (5 ml) was then added thereto. The reaction mixture was stirred overnight at 25° C. DMSO (7 ml) was then added and the ether was evaporated. The reaction mixture was stirred overnight at 100° C.

Synthesis of (1 alpha, 3 Beta, 5E, 7E, 20R, 1'E)-1,3-bis-(tert-butyldimethylsilyloxy)-20-Methyl(2-Methyl,1'-Heptenylate)-9,10-secopregna-5,7,10,(19)-triene:

To a suspension of lithium metal in 2 ml of dry ether, a solution of phenyl bromide in 3 ml of dry ether was added dropwise, under nitrogen atmosphere. An exothermic reaction was observed during the dissolution of the lithium metal. The reaction mixture was heated until complete dissolution of the lithium metal was achieved.

Triphenylphosphine 99% (1.447 grams, 5.52 mmol) and DMSO were added to the reaction solution of methyl 4-iodo-2-methyl-butyrate described above and the resulting mixture was heated to 100° C. for 18 hours. The mixture was then cooled to −30° C. under nitrogen atmosphere, and the phenyl lithium solution in ether was added thereto.

This reaction mixture was stirred at 0° C. for 1 hour and thereafter a hexane solution of the aldehyde CLP-8-Beta,5E, 7E,20R,1'E)-1,3-bis-(tert-butyldimethylsilyloxy)-9,10-secopregna-5,7,10,(19)-triene-aldehyde- was added. The obtained mixture was stirred at 100° C. overnight. The ether and the hexane were thereafter distilled, the reaction mixture was cooled to 60° C. and 50 ml ethyl acetate in 75 ml water were added thereto. The Organic layer was separated, washed with 25 ml water and brine and dried over sodium sulfate. The organic solvent was evaporated under reduced pressure and the residue was dried under high vacuum and was purified on silica gel column (60 grams) with a mixture of hexane-EtOAc (98:2) as an eluent, to obtain 60 mg of the product (1 alpha,3 Beta,5E,7E,20R,1'E)-1,3-bis-(tert-butyldimethylsilyloxy)-20-(2-methyl, 1'heptenylate)-9,10-secopregna-5,7,10,(19)-triene.

Synthesis of (1 alpha, 3 beta, 5E, 7E, 20R, 1'E)-1,3-bis-(tert-butyldimethylsilyloxy)-20-(2-methyl-2-hydroxy-1'heptenoic acid)-9,10-secopregna-5,7,10,(19)-triene:

(1 alpha, 3 Beta, 5E, 7E, 20R, 1'E)-1,3-bis-(tert-butyldimethylsilyloxy)-20-(2-methyl-1'-heptenylate)-9,10-secopregna-5, 7, 10, (19)-triene (60 mg) was dissolved in 3 ml THF and the solution was cooled to −78° C. under a stream of argon. $LiN(iPr)_2$ was added to the reaction mixture, so as to obtain the lithium derivative, which was further reacted with oxygen for 1 hour at −78° C. Triphenylphosphine was then added and the reaction mixture was stirred for 30 minutes. The resulting reaction mixture was then evaporated under vacuum. A solution of KOH in methanol was added to the residue and the reaction mixture was heated to 60° C. for 2.5 hours and was thereafter diluted with 0.5 ml 1N HCl, and evaporated under vacuum. The residue was dissolved in chloroform and the product was purified on silica gel plate (20× 20), using a mixture of 97:3 hexane-ethyl acetate (2 times) as the eluent., to obtain 6.3 mg of the product as fraction 2 (Rf=0.81).

The obtained product was then treated with a solution of 15.2 mg iodine in 2 ml methylene chloride, in the presence of pyridine (12 mg) and the reaction mixture was evaporated under vacuum and thereafter under high vacuum. The residue was dissolved with THF and $n-Bu_3SnH$ (29.1 mg) was added thereto. The reaction mixture was stirred at room temperature for 4 hours and was thereafter evaporated under vacuum.

The residue was treated with catalytic amounts of HCl in methanol at 50° C. for 5 hours. The reaction mixture was evaporated under vacuum and the residue was purified on silica gel TLC plate (20×20) using a mixture of 95:5 chloroform-methanol as the eluent, to obtain 2.64 mg of the desired product 9,10-secocholesta-5,7,10(19)-trien-26-oic acid, 1,3, 23,25-tetrahydroxy-gamma-lactone or (23S, 25R)-1alpha, 25-DihydroxyvitaminD3-26,23-lactone, as fraction 1 (Rf=0.4); FAB-MS: Calc. 426.60, Found 426.88.

Example 5

Effect of Nicotinamide on Ex-Vivo Exansion of Hematopoietic Stem/Progenitor Cells Nicotinamide Supplementation of Ex-Vivo Hematopoietic Stem/Progenitor Cell Cultures:

Cultures were prepared and maintained as described above. Nicotinamide was added to cell cultures at concentrations of 1, 5 or 10 mM for up to three weeks culture period. All other procedures including mononuclear cell fraction collection and purification, purification of CD34+ cells from mononuclear cell fractions, ex-vivo expansion of stem/progenitor cell populations, morphological assessment, surface antigen analysis, determination of CD34, CD38, Lin and other hematopoietic marker expression and cell population calculations were carried out as described in the experimental methods section of Example 1 above.

Experimental Results

Figure 14:
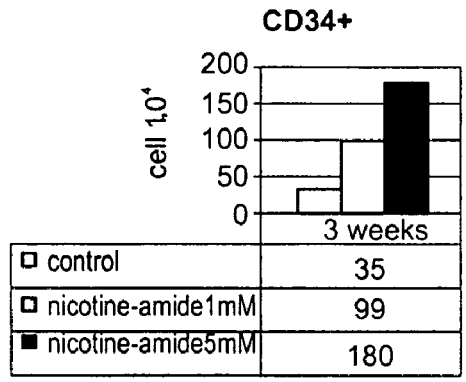
FIG. 14 is a bar graph presenting the density of CD34+ cells enumerated in 3 weeks culture. The cell culture was supplemented with SCF, TPO, FLt3, IL-6 and IL-3 cytokines, with or without nicotinamide at 1 mM and 5 mM concentrations. A marked increase in CD34+ cells density in the nicotinamide treated cultures is demonstrated.
Figure 15:
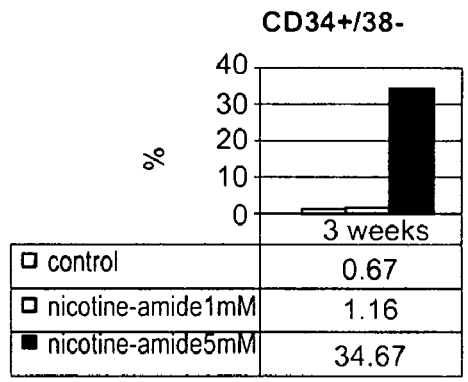
FIG. 15 is a bar graph presenting the data obtained by FACS analysis of CD34+/CD38− cells in 3 weeks culture. The cell culture was supplemented with SCF, TPO, FLt3, IL-6 and IL-3 cytokines, with or without nicotinamide at 1 mM and 5 mM concentrations. A marked increase in CD34+/CD38− cell density in the nicotinamide treated cultures is demonstrated.
Figure 16:
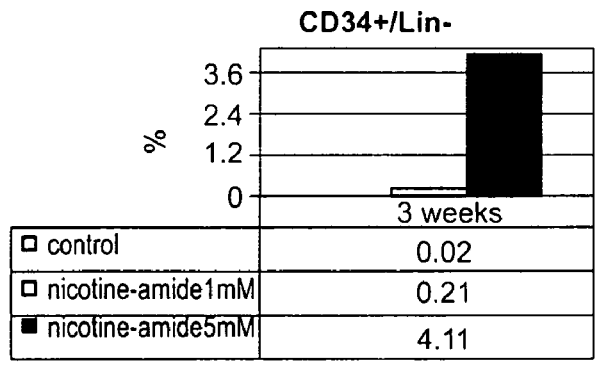
FIG. 16 is a bar graph presenting the data obtained by FACS analysis of CD34+/Lin− cells in 3 weeks culture. The cell culture was supplemented with SCF, TPO, FLt3, IL-6 and IL-3 cytokines, with or without nicotinamide at 1 mM and 5 mM concentrations. A marked increase in CD34+/Lin− cell density in the nicotinamide treated cultures is demonstrated.
Figure 17:
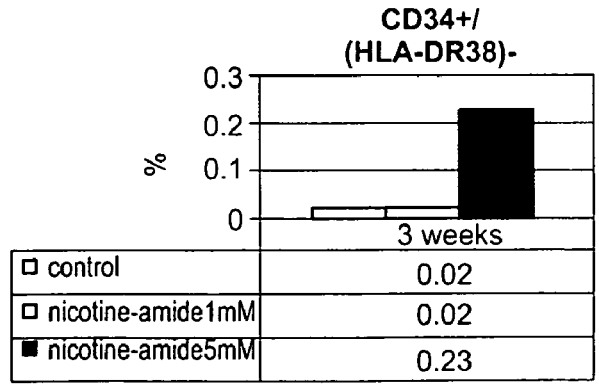
FIG. 17 is a bar graph presenting the data obtained by FACS analysis of CD34+/(HLA-DR38)− cells in 3 weeks culture. The cell culture was supplemented with SCF, TPO, FLt3, IL-6 and IL-3 cytokines, with or without nicotinamide at 1 mM and 5 mM concentrations. A marked increase in CD34+/(HLA-DR38)− cell density in the nicotinamide treated cultures is demonstrated.

Effects of Nicotinamide on the Ex-Vivo Expansion of Stem and Progenitor Hematopoietic Cells:

Hematopoietic CD34+ cell cultures were initiated in the presence of a combination of 5 cytokines, SCF, TPO, FLt3, IL-6 and IL-3, with or without different concentrations of nicotinamide. Following three weeks incubation period, the CD34+ cells were re-selected from culture by affinity re-purification method and were enumerated. The results, presented in FIG. 14, show that cultures supplemented with 1 and 5 mM nicotinamide yielded $99 \times 10^4$ and $180 \times 10^4$ CD34+ cells per ml, respectively, as compared with only $35 \times 10^4$ CD34+ cells per ml in the non-treated (cytokines only) control. In addition, the re-selected CD34+ cell fraction was FACS analyzed for stem/progenitor cell markers. The results, presented in FIGS. 15-17 and 18a-b, show substantial increases in the proportion of CD34+/CD38−, CD34+/Lin− and CD34+/(HLA-DR38−) cells in cultures treated with nicotinamide. FIG. 15 shows that cultures supplemented with 1 and 5 mM nicotinamide resulted in 1.7 and 51.7 fold increase, respectively, in CD34+/CD38− cells density, as compared with the untreated (cytokines only) control. FIG. 16 shows that cultures supplemented with 1 and 5 mM nicotinamide resulted in 10.5 and 205.5 fold increase, respectively, in CD34+/Lin−cells density, as compared with the untreated (cytokines only) control. FIG. 17 shows that cultures supplemented with 5 mM nicotinamide resulted in 11.5 fold increase in CD34+/(HLA-DR38−) cells density, as compared with the untreated (cytokines only) control. Hence, nicotinamide was found to be a very effective agent for promoting ex vivo expansion of stem and progenitor cells.

In an additional experiment, cultures were treated with 5 and 10 mM nicotinamide. Table 5 below presents the obtained results, which further demonstrate the powerful effect of nicotinamide on ex-vivo expansion of stem and early progenitor cells.

TABLE 5

| Treatment | % of CD34+/CD38− of total cells | % of CD34+/Lin− of total cells |
| --- | --- | --- |
| control | 1.69 | 0.02 |
| Nicotinamide (5 mM) | 9.69 | 4.11 |
| Nicotinamide (10 mM) | 34.67 | 16.58 |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent and patent application was specifically and individually indicated to be incorporated herein by reference. In addition, citation or identification of any reference in this application shall not be construed as an admission that such reference is available as prior art to the present invention.

REFERENCES CITED

Additional References Are Cited in the Text

1. Kastner P, Mark M, Chambon P. Nonsteroid nuclear receptors: what are genetic studies telling us about their role in real life? Cell. 1995; 83:859-86
2. Mangelsdorf D, Evans R. The RXR and orphan receptors. Cell. 1995; 83:841-850
3. Minucci S. and Pelicci P. G. Retinoid receptors in health and disease: co-regulators and the chromatin connection. Semin Cell Dev Biol. 1999; 10(2):215-25.
4. Brand N, Petkovich M, Krust A, Chambon P, de The H, Marchio A, Tiollais P, Dejean A. Identification of a second human retinoic acid receptor. Nature, 1988; 332: 850-53
5. Ishikawa T, Umesono K, Mangelsdorf D J, Aburatani H, Stanger B Z, Shibasaki Y, Imawari M, Evans R M, Takaku F. A functional retinoic acid receptor encoded by the gene on human chromosome 12. Mol. Endocrin. 1990; 4: 837-44
6. Mangelsdorf D J, Ong E S, Dyck J A, Evans R M. Nuclear receptor that identifies a novel retinoic acid response pathway. Nature. 1990; 345: 224-29
7. Mangelsdorf D J, Borgmeyer U, Heyman R A, Zhou J Y, Ong E S, Oro A E, Kakizuka A, Evans R M. Characterization of three RXR genes that mediate the action of 9-cis retinoic acid. Genes and Devel. 1992; 6: 329-44
8. Mangelsdorf D J, Umesono K, Kliewer S A, Borgrneyer U, Ong E S, Evans R M. A direct repeat in the cellular retinol-binding protein type II gene confers differential regulation by RXR and RAR. Cell. 1991; 66(3):555-61.
9. Heyman R A, Mangelsdorf D J, Dyck J A, Stein R B, Eichele G, Evans R M, Thaller C. 9-cis retinoic acid is a high affinity ligand for the retinoid X receptor. Cell. 1992; 68: 397406
10. Levin A A, Sturzenbecker L J, Kazmer S, Bosakowski T, Huselton C, Allenby G, Speck J, Kratzeisen C, Rosenberger M, Lovey A, et al. 9-cis retinoic acid stereoisomer binds and activates the nuclear receptor RXR alpha. Nature. 1992; 355: 359-61
11. Levin M. S., and Davis A. E. Retinoic acid increases cellular retinol-binding protein II mRNA and retinol uptake in the human intestinal Caco-2 cell line. J. Nutr. 1997; 127: 13-17
12. Suruga K, Mochizuki K, Suzuki R, Goda T, and Takase S. Regulation of cellular retinol-binding protein type II gene expression by arachidonic acid analogue and 9-cis retinoic acid in Caco-2 cells. Eur. J. Biochem. 1999; 262:70-78
13. Kliewer, SA., Umesono K, Noonan D J, Heyman R A, and Evans R M. Convergence of 9-cis retinoic acid and peroxisome proliferator signaling pathway through heterodimer formation of their receptors. Nature 1992; 358: 771-774.

14. Siegenthaler G. Extra-and intracellular transport of retinoids: a reappraisal. Horm Res. 1996; 45:122-127

15. Sherman M I, Gubler M L, Barkai U, Harper M I, Coppola G, Yuan J. Role of retinoids in differentiation and growth of embryonal carcinoma cells. Ciba Found Symp. 1985;113:42-60.

16. Herdick M, Steinmeyer A, Carlberg C. Carboxylic ester antagonists of 1alpha,25-dihydroxyvitamin D(3) show cell-specific actions. Chem Biol. 2000: 7:885-94.

17. Jimenez-Lara A M, Aranda A. Interaction of vitamin D and retinoid receptors on regulation of gene expression. Horm Res. 2000; 54:301-5

18. Evans R. The steroid and thyroid hormone receptor super family. Science. 1988;240:889-895.

19. Breitman T, Selonick S, Collins S. Induction of differentiation of the human promyelocytic leukemia cell line (HL-60) by retinoic acid. Proc Natl Acad Sci USA. 1980;77:2936-2940.

20. Purton L E, Bernstein I D, Collins S J. All-trans retinoic acid delays the differentiation of primitive hematopoietic precursors (lin c-kit+ Sca-1+) while enhancing the terminal maturation of committed granulocyte/monocyte progenitors. Blood. 1999;94:483-495.

21. Louise E. Purton, Irwin D. Bernstein, and Steven J. Collins, All-trans retinoic acid enhances the long-term repopulating activity of cultured hematopoietic stem cells. Blood. 2000; 95: 470-477

22. Muramatsu M, Hanazono Y, Ogasawara Y, Okada T, Mizukami H, Kume A, Mizoguchi H, Ozawa K. Reversible integration of the domain negative retinoid receptor gene for ex-vivo expansion of hematopoietic stem/progenitor cells. Biochem Biophys Res Commun 2001; 285:891-6

23. U.S. Pat. No. 5,830,760. creating novel hematopoietic cell lines by expressing altered retinoic acid receptors.

24. Kapil M., Teresa M., Taghi M., Michael A., Steven C., Maher A. Involvement of retinoic acid receptor mediated signaling pathway in induction of CD38 cell surface antigen, Blood. 1997; 89:3607-3614

25. Ueno H, Kizaki M, Matsushita H, Muto A, Yamato K, Nishihara T, Hida T, Yoshimura H, Koeffler H P, Ikeda Y. A novel retinoic acid receptor (RAR)-selective antagonist inhibits differentiation and apoptosis of HL-60 cells: implications of RAR alpha-mediated signals in myeloid leukemic cells. Leuk Res. 1998; 22:517-25

26. Johnson A T, Wang L, Standeven A M, Escobar M, Chandraratna R A. Synthesis and biological activity of high-affinity retinoic acid receptor antagonists. Bioorg Med Chem. 1999; 7(7):1321-38.

27. Endo Y. "Dicarba-closo-dodecaboranes as a pharmacophore. Retinidal antagonists and potential agonists". Chem Pharm Bull. 1999; 47(3):398404.

28. Drayson M T, Michell R H, Durham J, Brown G. Cell proliferation and CD11b expression are controlled independently during HL60 cell differentiation initiated by 1,25 alpha-dihydroxyvitamin D(3) or all-trans-retinoic acid. Exp Cell Res. 2001;266(1):126-34

29. Gudas, LJ, Sporn, MB, & Roberts, AB. Cellular biology and biochemistry of the retinoids. In: The retinoids: biology, chemistry and medicine. 1994:443 516.

30. Wolbach, SB & Howe, PR. Tissue changes following deprivation of fat-soluble A vitamin. J Exp Med 1925, 42:753 777.

31. De The, H, Marchino, A, Tiollais, P, & Dejean, A. Differential expression and ligand regulation of the retinoic acid receptor α and β genes. EMBO J. 1989, 8:429 433

32. De The, H, Vivanco Ruiz, M, Tiollais, P, Stunnenberg, H, & Dejean, A. Identification of retinoic responsive element in the retinoic acid receptor gene. Nature. 1990; 343:177 180.

33. Nervi, C, Vollberg, T M, George, M D, Zelent, A, Chambon, P, & Jetten, A M. Expression of nuclear retinoic acid receptors in normal tracheobronchial cells and in lung carcinoma cells. Exp Cell Res. 1991; 195:163 170.

34. Swisshelm, K, Ryan, K, Lee, X, Tsou, HC, Peacocke, M, and Sager, R. Down-regulation of retinoic acid receptor β in mammary carcinoma cell lines and its up-regulation in senescing normal mammary epithelial cells. Cell Growth Differ. 1994; 5:133 141

35. Caliaro, MJ, Marmouget, C, & Guichard, S. Response of four ovarian carcinoma cell lines to all-trans retinoic acid: relationship with induction of differentiation and retinoic acid receptor expression. Int J Cancer 1994, 56:743 748.

36. Comerci, JT, Hallam, S, Goldberg, GL, Runowcz, CD, Fields, A L, Wadler, S, & Gallagher, RE. Expression of retinoic acid receptor-β2 mRNA in normal cervical epithelium and cervical squamous cell carcinoma. Int J Oncology 1997, 11:983 988.

37. Xu, XC, Ro, JY, Lee, JS, Shin, DM, Hong, WK, and Lotan, R. Differential expression of nuclear retinoid receptors in normal, premalignant and malignant head and neck tissues. Cancer Res 1994; 54:3580 3587

38. Labrecque J., et al. Impaired granulocytic differentiation in vitro in hematopoietic cells lacking retinoic acid receptors alpha1 and gamma Blood 1998; 92: 607-615.

39. Douer D, Ramezani L, Parker J, Levine A M. All-trans-retinoic acid affects the growth, differentiation and apoptosis of normal human myeloid progenitors derived from purified CD34+ bone marrow cells. Leukemia. 2000; 14:874-881.

40. Morosetti R, Grignani F, Liberatore C, et al. Infrequent alterations of the RAR gene in acute myelogenous leukemias, retinoic acid-resistant acute promyelocytic leukemias, myelodysplastic syndromes and cell lines. Blood 1996; 87:4399-4403.

41. Purton L E, Bernstein I D, and Collins S J. All-trans retinoic acid enhances the long-term repopulating activity of cultured hematopoietic stem cells. Blood. 2000; 95(2): 470477.

42. Douer D, Ramezani L, Parker J, Levine A M. All-trans-retinoic acid affects the growth, differentiation and apoptosis of normal human myeloid progenitors derived from purified CD34+ bone marrow cells. Leukemia. 2000;14:874-881

43. Kamei Y, Kawada T, Mizukami J, Sugimoto E. The prevention of adipose differentiation of 3T3-L1 cells caused by retinoic acid is elicited through retinoic acid receptor alpha. Life Sci. 1994; 55(16):PL307-12

44. Van Epps D E, et al. Harvesting, characterization, and culture of CD34+ cells from human bone marrow, peripheral blood, and cord blood. Blood Cells 20:411, 1994.

45. Emerson S G. Ex-vivo expansion of hematopoietic precursors, progenitors, and stem cells: The next generation of cellular therapeutics. Blood 87:3082, 1996.

46. Brugger W, et al. Reconstitution of hematopoiesis after high-dose chematotherapy by autologous progenitor cells generated in-vivo. N Engl J Med 333:283, 1995.

47. Williams S F, et al. Selection and expansion of peripheral blood CD34+ cells in autologous stem cell transplantation for breast cancer. Blood 87:1687, 1996.

48. Zimmerman R M, et al. Large-scale selection of CD34+ peripheral blood progenitors and expansion of neutrophil precursors for clinical applications. J Heamatotherapy 5:247, 1996.

49. Koller M R, Emerson S G, Palsson B O. Large-scale expansion of human stem and progenitor cells from bone marrow mononuclear cells in continuous perfusion cultures. Blood 82:378, 1993.

50. Lebkowski J S, et al. Rapid isolation and serum-free expansion of human CD34+ cells. Blood Cells 20:404, 1994.

51. Sandstrom C E, et al. Effects of CD34+ cell selection and perfusion on ex-vivo expansion of peripheral blood mononuclear cells. Blood 86:958, 1995.

52. Palmiter R D. Regulation of metallothionein genes by heavy metals appears to be mediated by a zinc-sensitive inhibitor that interacts with a constitutively active transcription factor, MTF-1. Proc Natl Acad Sci USA 91(4): 1219-1223, 1994.

53. Freedman A R, et al. Generation of T lymphocytes from bone marrow CD34+ cells in-vitro. Nature Medicine 2: 46, 1996.

54. Heslop H E, et al. Long term restoration of immunity against Epstein-Barr virus infection by adoptive transfer of gene-modified virus-specific T lymphocytes. Nature Medicine 2: 551, 1996.

55. Protti M P, et al. Particulate naturally processed peptides prime a cytotoxic response against human melanoma in-vitro. Cancer Res 56: 1210, 1996.

56. Rosenberg S A, et al. Prospective randomized trial of high-dose interleukin-2 alone or in conjunction with lymphokine-activated killer cells for the treatment of patients with advanced cancer. J Natl Cancer Inst 85: 622, 1993.

57. Bernhard H, et al. Generation of immunostimulatory dendritic cells from human CD34+ hematopoietic progenitor cells of the bone marrow and peripheral blood. Cancer Res 10: 99, 1995.

58. Fisch P, et al. Generation of antigen-presenting cells for soluble protein antigens ex-vivo from peripheral blood CD34+ hematopoietic progenitor cells in cancer patients. Eur J Immunol 26: 595, 1996.

59. Siena S, et al. Massive ex-vivo generation of functional dendritic cells from mobilized CD34+ blood progenitors for anticancer therapy. Expt Hematol 23:1463, 1996.

60. Repair of myelin disease: Strategies and progress in animal models. Molecular Medicine Today. December 1997. pp. 554-561

61. Schechtez A N et al. Sickle cell anemia. In: Molecular basis of blood diseases. Stamatoyannaopoulos G, Nienhuis A W, Leder P and Majerus P W Eds. pp. 179-218, Sounders Philadelphia.

62. Alter B P. Fetal erythropoiesis in stress hemopoiesis. Experimental Hematology 7: 200, 1979.

63. Blau C A et al. Fetal hemoglobin in acute and chronic stage of erythroid expansion. Blood 81: 227, 1993.

64. Lala D S, Mukherjee R, Schulman I G, Koch S S, Dardashti L J, Nadzan A M, Croston G E, Evans R M, Heyman R A. Activation of specific RXR heterodimers by an antagonist of RXR homodimers. Nature. 1996; 383:450-3.

65. Kochhar D M, Jiang H, Penner J D, Johnson A T, Chandraratna R A. The use of a retinoid receptor antagonist in a new model to study vitamin A-dependent developmental events. Int. J. Dev. Biol. 1998;42(4):601-8

66. Li M, Chiba H, Warot X, Messaddeq N, Gerard C, Chambon P, Metzger D. RXR-alpha ablation in skin keratinocytes results in alopecia and epidermal alterations. Development. 2001;128(5):675-88.

What is claimed is:

1. A method of expanding a population of CD34+ hematopoietic stem cells ex-vivo, while at the same time, inhibiting differentiation of the stem cells ex-vivo, the method comprising:
(a) culturing said CD34+ hematopoietic stem cells ex-vivo under conditions allowing for cell proliferation, said conditions which comprise providing nutrients, serum and a combination of cytokines including each of stem cell factor, thrombopoietin, FLt3 ligand, and IL-6 and optionally IL-3 and,
(b) in the same culture medium providing nicotinamide in an amount between 1.0 mM to 10 mM,
wherein culturing said cells for a culture period of three weeks results in expanding the population of CD34+ hematopoietic stem cells while inhibiting differentiation of said CD34+ hematopoietic stem cells ex-vivo to produce an expanded CD34+ hematopoietic stem cell population with an increased proportion of CD34+/Lin− and CD34+/CD38− cells in the expanded culture as compared to CD34+ cells cultured in the presence of cytokines and nutrients without exogenously added nicotinamide.

2. The method of claim 1, wherein said population of stem cells are selected from the group consisting of: embryonic stem cells and adult stem cells.

3. The method of claim 1, wherein said stem cells are derived from a source selected from the group consisting of: bone marrow, peripheral blood and neonatal umbilical cord blood.

4. The method of claim 1, wherein said expanded hematopoietic cells are further characterized by an absence, or significantly diminished expression of cell surface antigens CD3, CD61, CD19, CD33, CD14, CD15 or CD4.

5. The method of claim 1, wherein said combination of cytokines further comprise at least one cytokine selected from the group consisting of: interleukin-1, interleukin-2 interleukin-10, interleukin-12 and tumor necrosis factor-α.

6. The method of claim 1, which method further comprises providing late acting cytokines.

7. The method of claim 6, wherein said late acting cytokines are selected from the group consisting of: granulocyte colony stimulating factor, granulocyte/macrophage colony stimulating factor, erythropoietin, FGF, EGF, NGF, VEGF, LIF, Hepatocyte growth factor and macrophage colony stimulating factor.

8. The method of claim 1, wherein said culturing said cells in the presence of said exogenously added nicotinamide is for a period of up to three weeks.

9. The method of claim 1, wherein said cells are cultured in the presence of 1.0 mM of exogenously added nicotinamide.

10. The method of claim 1, wherein said cells are cultured in the presence of 5.0 mM of exogenously added nicotinamide.

11. The method of claim 1, wherein said cells are cultured in the presence of 10.0 mM of exogenously added nicotinamide.

* * * * *

UNITED STATES PATENT AND TRADEMARK OFFICE
CERTIFICATE OF CORRECTION

PATENT NO. : 7,955,852 B2  Page 1 of 1
APPLICATION NO. : 10/774843
DATED : June 7, 2011
INVENTOR(S) : Peled et al.

It is certified that error appears in the above-identified patent and that said Letters Patent is hereby corrected as shown below:

On the Title Page:

Please insert the following section after the section entitled "Related U.S. Application Data":

-- Foreign Application Priority Data

Nov. 17, 2002      (IL).........................................152904 --

Signed and Sealed this
Sixteenth Day of August, 2011

David J. Kappos
*Director of the United States Patent and Trademark Office*